United States Patent
Jansen et al.

(10) Patent No.: US 7,297,797 B2
(45) Date of Patent: Nov. 20, 2007

(54) PYRROLINES

(75) Inventors: Johannes Rudolf Jansen, Monheim (DE); Udo Kraatz, Leverkusen (DE); Hubertus Stakemeier, Bergisch Gladbach (DE); Thomas Seitz, Langenfeld (DE); Fritz Maurer, Lauffen (DE); Martin Füsslein, Düsseldorf (DE); Bernd Alig, Königswinter (DE); Christian Funke, Leichlingen (DE); Werner Hallenbach, Monheim (DE); Jörg Konze, Köln (DE); Udo Beckmann, Köln (DE); Ulrich Görgens, Ratingen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/528,259

(22) PCT Filed: Sep. 8, 2003

(86) PCT No.: PCT/EP03/09938

§ 371 (c)(1),
(2), (4) Date: Dec. 12, 2005

(87) PCT Pub. No.: WO2004/031176

PCT Pub. Date: Apr. 15, 2004

(65) Prior Publication Data

US 2006/0142343 A1    Jun. 29, 2006

(30) Foreign Application Priority Data

Sep. 24, 2002 (DE) .............................. 102 43 939

(51) Int. Cl.
- *C07D 413/14* (2006.01)
- *C07D 413/10* (2006.01)
- *C07D 411/14* (2006.01)
- *C07D 411/10* (2006.01)
- *C07D 409/14* (2006.01)
- *C07D 405/14* (2006.01)
- *C07D 401/14* (2006.01)

(52) U.S. Cl. ............................... 546/269.4; 546/268.7; 546/272.7; 546/272.4; 546/275.4; 546/280.4; 546/283.7; 546/282.4; 548/122; 548/123; 548/124; 548/125; 548/146; 548/206; 548/215; 548/240; 548/255; 548/400; 548/262.2; 548/300.1

(58) Field of Classification Search ............ 546/269.4, 546/268.7, 272.7, 272.4, 275.4, 280.4, 283.7, 546/282.4; 548/122, 123, 124, 125, 146, 548/206, 215, 240, 255, 400, 262.2, 300.1
See application file for complete search history.

(56) References Cited

U.S. PATENT DOCUMENTS

| 6,599,924 | B1 | 7/2003 | Plant et al. | 514/343 |
| 2003/0220386 | A1 | 11/2003 | Plant et al. | 514/408 |
| 2004/0059129 | A1 | 3/2004 | Plant et al. | 548/405 |
| 2004/0077881 | A1 | 4/2004 | Plant et al. | 548/577 |

FOREIGN PATENT DOCUMENTS

| CA | 2430683 A1 * | 6/2002 |
| WO | 94/29268 | 12/1994 |
| WO | 98/22438 | 5/1998 |
| WO | 99/59967 | 11/1999 |
| WO | 99/59968 | 11/1999 |
| WO | 02/24646 | 3/2002 |
| WO | 02/46151 | 6/2002 |
| WO | 02/064588 | 8/2002 |
| WO | 02/076978 | 10/2002 |
| WO | 03/067986 | 8/2003 |

OTHER PUBLICATIONS

Chem. Ind, 37, (month unavailable) 1985, pp. 730-732, Harry R. Ungerer, "Schiffsfarben—eine Spezialität der seenanhen Lackindustrie".

* cited by examiner

Primary Examiner—Kamal A. Saeed
Assistant Examiner—Michael Barker
(74) Attorney, Agent, or Firm—Richard EL Henderson

(57) ABSTRACT

The invention relates to novel $\Delta^1$-pyrrolines of the formula (I)

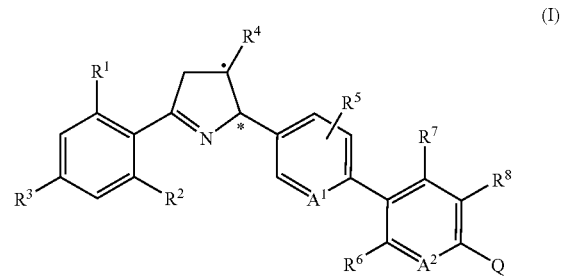

in which $R^1$, $R^2$, $R^3$, $R^4$, $A^1$, $A^2$, $R^5$, $R^6$, $R^7$, $R^8$, $R^9$ and Q are as defined in the disclosure, to a process for preparing these compounds and to their use for controlling pests.

12 Claims, No Drawings

PYRROLINES

The present patent application has been filed under 35 U.S.C. 371 as a national stage application of PCT/EP2003/009938, filed Sep. 8, 2003, which was published in German as International Patent Publication WO 2004/031176 on Apr. 15, 2004, and is entitled to the right of priority of German Patent Application 102 43 939.7, filed Sep. 24, 2002.

The present invention relates to novel $\Delta^1$-pyrrolines, to a plurality of processes for their preparation and to their use as active compounds, in particular their use as pesticides.

It is already known that numerous $\Delta^1$-pyrrolines have insecticidal properties (cf. WO 02/064588, WO 02/064561, WO 02/46151, WO 02/24646, WO 02/24644, WO 02/24643, WO 00/21958, WO 99/59968, WO 99/59967 and WO 98/22438). The activity of these compounds is good; however, it is sometimes unsatisfactory.

This invention now provides novel $\Delta^1$-pyrrolines of the formula (I)

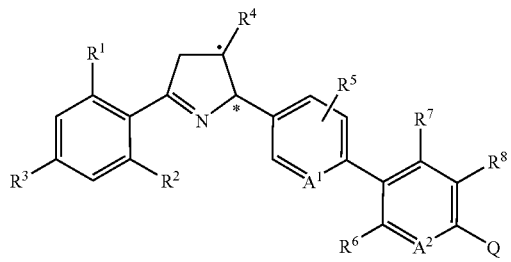

in which $R^1$ represents halogen, $C_1$-$C_4$-alkyl or $C_1$-$C_4$-haloalkyl, $R^2$ represents hydrogen, halogen, $C_1$-$C_4$-alkyl or $C_1$-$C_4$-haloalkyl, $R^3$ represents hydrogen, halogen or methyl, $R^4$ represents hydrogen, $C_1$-$C_6$-alkyl, ($C_1$-$C_6$-alkoxy)carbonyl, ($C_3$-$C_6$-cycloalkyl)-oxycarbonyl, ($C_1$-$C_6$-haloalkoxy)carbonyl, represents aryl which is optionally mono- or polysubstituted by identical or different substituents from the group consisting of halogen, cyano, nitro, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy and $C_1$-$C_4$-haloalkylthio, $A^1$ represents N or CH, $A^2$ represents N or $CR^9$, $R^5$ represents hydrogen, halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkyl, $C_1$-$C_6$-haloalkoxy, $C_1$-$C_6$-haloalkylthio, $C_1$-$C_6$-haloalkylsulphinyl or $C_1$-$C_6$-haloalkylsulphonyl, $R^6$, $R^7$, $R^8$ and $R^9$ independently of one another represent hydrogen, halogen, cyano, formyl, nitro, tri($C_1$-$C_6$-alkyl)silyl, $C_1$-$C_6$-alkyl, $C_1$-$C_6$-alkoxy, $C_1$-$C_6$-alkylthio, $C_1$-$C_6$-alkyl-sulphinyl, $C_1$-$C_6$-alkylsulphonyl, $C_2$-$C_6$-alkenyl, $C_2$-$C_6$-alkenyloxy, ($C_1$-$C_6$-alkyl)carbonyl, ($C_1$-$C_6$-alkoxy)carbonyl, $C_1$-$C_6$-haloalkyl, $C_1$-$C_6$-haloalkoxy, $C_1$-$C_6$-halo-alkylthio, $C_1$-$C_6$-haloalkylsulphinyl, $C_1$-$C_6$-haloalkylsulphonyl, $C_2$-$C_6$-haloalkenyl, $C_2$-$C_6$-haloalkenyloxy, ($C_1$-$C_6$-haloalkyl)carbonyl, ($C_1$-$C_6$-haloalkoxy)carbonyl, pentafluorothio, —C($R^{10}$)=N—OR$^{11}$, —SO$_2$NR$^{12}$R$^{13}$, —(CH$_2$)$_p$NR$^{12}$R$^{13}$, —(CH$_2$)$_p$N(R$^{12}$)COR$^{13}$, —(CH$_2$)$_p$N(R$^{12}$)SO$_2$R$^{13}$, —OSO$_2$R$^{12}$ or —OSO$_2$NR$^{12}$R$^{13}$, $R^{10}$ represents hydrogen, $C_1$-$C_6$-alkyl, $C_2$-$C_6$-alkenyl, $C_1$-$C_6$-haloalkyl, $C_2$-$C_6$-haloalkenyl or $C_3$-$C_6$-cycloalkyl, $R^{11}$ represents hydrogen, $C_1$-$C_6$-alkyl, $C_2$-$C_6$-alkenyl, $C_1$-$C_6$-haloalkyl, $C_2$-$C_6$-haloalkenyl, $C_3$-$C_6$-cycloalkyl-$C_1$-$C_4$-alkyl or aryl-$C_1$-$C_4$-alkyl which is optionally mono- or polysubstituted by identical or different radicals $R^5$, $R^{12}$ and $R^{13}$ independently of one another represent hydrogen, $C_1$-$C_6$-alkyl, $C_1$-$C_6$-haloalkyl, represent $C_3$-$C_6$-cycloalkyl which is optionally mono- or polysubstituted by identical or different substituents from the group consisting of halogen and $C_1$-$C_6$-alkyl, represents $C_3$-$C_6$-cycloalkyl-$C_1$-$C_4$-alkyl or represents aryl-$C_1$-$C_4$-alkyl which is optionally mono- or polysubstituted by identical or different radicals $R^5$, $R^{12}$ and $R^{13}$ furthermore together represent $C_2$-$C_6$-alkylene, ($C_1$-$C_3$-alkoxy)-$C_1$-$C_3$-alkylene or ($C_1$-$C_3$-alkylthio)-$C_1$-$C_3$-alkylene, each of which is optionally mono- or polysubstituted by identical or different substituents from the group consisting of halogen and $C_1$-$C_6$-alkyl, p represents 0, 1 or 2, Q represents a completely unsaturated 5-membered heterocycle which has 1 to 3 identical or different heteroatoms from the group consisting of nitrogen, oxygen and sulphur and which is mono- or polysubstituted by identical or different radicals from the list $W^1$, and $W^1$ represents halogen, cyano, $C_1$-$C_{16}$-alkyl, $C_1$-$C_{16}$-alkoxy, $C_1$-$C_{16}$-alkylthio, $C_1$-$C_{16}$-alkylsulphinyl, $C_1$-$C_{16}$-alkylsulphonyl, $C_1$-$C_{16}$-haloalkyl, $C_1$-$C_{16}$-haloalkoxy, $C_1$-$C_{16}$-haloalkylthio, $C_1$-$C_{16}$-haloalkylsulphinyl, $C_1$-$C_{16}$-haloalkylsulphonyl, $C_3$-$C_{12}$-cyclo-alkyl or represents aryl or aryl-$C_1$-$C_4$-alkyl, each of which is optionally mono- or polysubstituted by identical or different substituents from the group consisting of halogen, cyano, formyl, nitro, tri($C_1$-$C_6$-alkyl)silyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_2$-$C_6$-alkenyl, $C_2$-$C_6$-alkenyloxy, ($C_1$-$C_6$-alkyl)carbonyl, ($C_1$-$C_6$-alkoxy)carbonyl, $C_1$-$C_6$-haloalkyl, $C_1$-$C_6$-haloalkoxy, $C_1$-$C_6$-haloalkylthio, $C_1$-$C_6$-haloalkylsulphinyl, $C_1$-$C_6$-haloalkylsulphonyl, $C_2$-$C_6$-haloalkenyl, $C_2$-$C_6$-haloalkenyloxy, —C($R^{10}$)=N—OR$^{11}$, —SO$_2$NR$^{12}$R$^{13}$, —(CH$_2$)$_p$NR$^{12}$R$^{13}$, —(CH$_2$)$_p$N(R$^{12}$)COR$^{13}$, —(CH$_2$)$_p$N(R$^{12}$)SO$_2$R$^{13}$, —OSO$_2$R$^{12}$ or —OSO$_2$NR$^{12}$R$^{13}$.

In the formula (I), * denotes a stereogenic centre. If $R^4$ does not represent hydrogen, • denotes a further stereogenic centre, where the substituents at the two centres may be in a cis- or trans-position to one another. The same nomenclature applies to all other formulae of this description.

Depending on the type and number of substituents, the compounds of the formula (I) may, if appropriate, be present as geometrical and/or optical isomers or regioisomers or isomer mixtures thereof of varying composition. What is claimed by the invention are both the pure isomers and the isomer mixtures.

Furthermore, it has been found that $\Delta^1$-pyrrolines of the formula (I) can be prepared by A) reacting $\Delta^1$-pyrrolines of the formula (II)

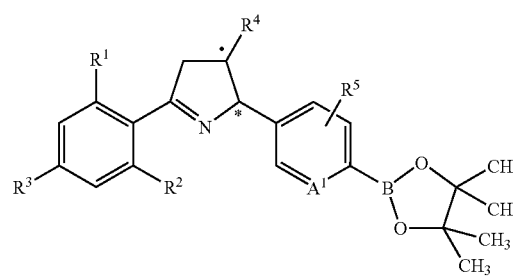

in which $R^1$, $R^2$, $R^3$, $R^4$, $A^1$ and $R^5$ are as defined above, with benzene derivatives of the formula (III)

$$\text{(III)}$$

[Structure: benzene ring with substituents $X^1$, $R^7$, $R^8$, $R^6$, $A^2$, Q]

in which $A^2$, $R^6$, $R^7$, $R^8$ and Q are as defined above and $X^1$ represents bromine, iodine or —OSO$_2$CF$_3$, in the presence of a catalyst and in the presence of a diluent.

Finally, it has been found that the compounds of the formula (I) according to the invention have very good insecticidal properties and can be used both in crop protection and in the protection of materials for controlling unwanted pests, such as insects, arachnids and mites.

The formula (I) provides a general definition of the compounds according to the invention. Preferred substituents and ranges of the radicals given in the formulae mentioned above and below are illustrated below.

$R^1$ preferably represents fluorine, chlorine, bromine, $C_1$-$C_4$-alkyl or $C_1$-$C_4$-haloalkyl having 1 to 9 fluorine, chlorine and/or bromine atoms.

$R^1$ particularly preferably represents fluorine, chlorine, bromine, methyl, ethyl, n-propyl, isopropyl, n-butyl, isobutyl, sec-butyl, tert-butyl or $C_1$-$C_4$-haloalkyl having 1 to 9 fluorine, chlorine and/or bromine atoms.

$R^1$ very particularly preferably represents fluorine, chlorine, bromine, methyl, ethyl, isopropyl, tert-butyl or trifluoromethyl.

$R^1$ especially preferably represents fluorine, chlorine or methyl.

$R^2$ preferably represents hydrogen, fluorine, chlorine, bromine, $C_1$-$C_4$-alkyl or $C_1$-$C_4$-haloalkyl having 1 to 9 fluorine, chlorine and/or bromine atoms.

$R^2$ particularly preferably represents hydrogen, fluorine, chlorine, bromine, methyl, ethyl, n-propyl, isopropyl, n-butyl, isobutyl, sec-butyl, tert-butyl or trifluoromethyl.

$R^2$ very particularly preferably represents hydrogen, fluorine, chlorine, methyl, ethyl, isopropyl or tert-butyl.

$R^2$ especially preferably represents hydrogen, fluorine, chlorine or methyl.

$R^3$ preferably represents hydrogen, fluorine, chlorine, bromine or methyl.

$R^3$ particularly preferably represents hydrogen, fluorine, chlorine or methyl.

$R^3$ very particularly preferably represents hydrogen, fluorine or chlorine.

$R^3$ especially preferably represents hydrogen or fluorine.

$R^4$ preferably represents hydrogen, $C_1$-$C_4$-alkyl, ($C_1$-$C_6$-alkoxy)carbonyl, ($C_3$-$C_6$-cyclo-alkyl)oxycarbonyl, ($C_1$-$C_4$-haloalkoxy)carbonyl having 1 to 9 fluorine and/or chlorine atoms, represents phenyl which is optionally mono- to tetrasubstituted by identical or different substituents from the group consisting of fluorine, chlorine, bromine, iodine, cyano, nitro, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy and $C_1$-$C_4$-haloalkylthio having in each case 1 to 9 fluorine, chlorine and/or bromine atoms.

$R^4$ particularly preferably represents hydrogen, methyl, ethyl, n-propyl, isopropyl, n-butyl, isobutyl, sec-butyl, tert-butyl, methoxycarbonyl, ethoxycarbonyl, n-propoxycarbonyl, isopropoxycarbonyl, n-butoxycarbonyl, isobutoxycarbonyl, sec-but-oxycarbonyl, tert-butoxycarbonyl, n-pentoxycarbonyl, neopentoxycarbonyl, sec-isoamyloxycarbonyl, pentan-3-yloxycarbonyl, n-hexyloxycarbonyl, cyclopentyloxy-carbonyl, cyclohexyloxycarbonyl, trifluoromethoxycarbonyl, trifluoroethoxy-carbonyl, represents phenyl which is in each case mono- or disubstituted by identical or different substituents from the group consisting of fluorine, chlorine, bromine, iodine, cyano, nitro, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy and $C_1$-$C_4$-haloalkylthio.

$R^4$ very particularly preferably represents methyl, ethyl, isopropyl, tert-butyl, methoxy-carbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentoxycarbonyl, neopentoxycarbonyl, sec-isoamyloxycarbonyl, pentan-3-yloxycarbonyl, n-hexyloxycarbonyl, cyclopentyloxycarbonyl, cyclohexyloxycarbonyl, represents phenyl which is optionally monosubstituted by fluorine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, methylthio, ethylthio, n-propylthio, isopropylthio, n-butylthio, isobutylthio, sec-butylthio, tert-butylthio, trifluoromethyl or trifluoromethoxy.

$R^4$ especially preferably represents hydrogen, methyl, ethyl, methoxycarbonyl, ethoxycarbonyl, 4-fluorophenyl or 4-chlorophenyl.

$A^1$ preferably represents N.

$A^1$ preferably represents CH.

$A^2$ preferably represents N.

$A^2$ preferably represents $CR^9$.

$A^2$ particularly preferably represents CH.

$R^5$ preferably represents hydrogen, fluorine, chlorine, bromine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl; $C_1$-$C_4$-haloalkoxy, $C_1$-$C_4$-haloalkylthio, $C_1$-$C_4$-haloalkylsulphinyl or $C_1$-$C_4$-haloalkylsulphonyl having in each case 1 to 9 fluorine, chlorine and/or bromine atoms.

$R^5$ particularly preferably represents hydrogen, fluorine, chlorine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, methylthio, ethylthio, n-propylthio, isopropylthio, n-butylthio, isobutylthio, sec-butylthio, tert-butylthio, methylsulphinyl, ethylsulphinyl, n-propylsulphinyl, isopropylsulphinyl, n-butylsulphinyl, isobutylsulphinyl, sec-butylsulphinyl, tert-butylsulphinyl, methyl-sulphonyl, ethylsulphonyl, n-propylsulphonyl, isopropylsulphonyl, n-butylsulphonyl, isobutylsulphonyl, sec-butylsulphonyl, tert-butylsulphonyl, tri-fluoromethyl, trifluoroethyl, trifluoromethoxy, trifluoroethoxy, trifluoromethylthio, trifluoroethylthio, trifluoromethylsulphinyl, trifluoroethylsulphinyl, tri-fluoromethylsulphonyl or trifluoroethylsulphonyl.

$R^5$ very particularly preferably represents hydrogen, fluorine, chlorine, methyl, ethyl, isopropyl, tert-butyl, methoxy, ethoxy, isopropoxy, tert-butoxy, methylthio, ethylthio, isopropylthio, tert-butylthio, methylsulphonyl, trifluoromethyl, trifluoro-methoxy, trifluoromethylthio or trifluoromethylsulphonyl.

$R^5$ especially preferably represents hydrogen, fluorine, chlorine, methyl, ethyl, methoxy or ethoxy.

$R^6$, $R^7$, $R^8$ and $R^9$ independently of one another preferably represent hydrogen, fluorine, chlorine, bromine, cyano, formyl, nitro, tri($C_1$-$C_4$-alkyl)silyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl; $C_1$-$C_4$-haloalkyl, $C_1$-$C_4$-haloalkoxy, $C_1$-$C_4$-haloalkylthio, $C_1$-$C_4$-haloalkylsulphinyl or $C_1$-$C_4$-haloalkyl-sulphonyl having in each case 1 to 9 fluorine, chlorine and/or bromine atoms; $C_2$-$C_4$-haloalkenyl or $C_2$-$C_4$-haloalkenyloxy having in each case 1 to 7 fluorine, chlorine and/or bromine atoms, ($C_1$-$C_4$-haloalkyl)carbonyl or ($C_1$-$C_4$-haloalkoxy)carbonyl, having in each case 1 to 9 fluorine, chlorine and/or bromine atoms, pentafluorothio, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$ or —OSO$_2$N$R^{12}R^{13}$, $R^6$, $R^7$, $R^8$ and $R^9$ independently of one another particularly preferably represent hydrogen, fluorine, chlorine, cyano, formyl, trimethylsilyl, dimethyl-tert-butylsilyl, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, methylthio, ethylthio, n-propylthio, isopropylthio, n-butylthio, isobutylthio, sec-butylthio, tert-butylthio, methylsulphinyl, ethylsulphinyl, n-propylsulphinyl, isopropylsulphinyl, n-butylsulphinyl, isobutylsulphinyl, sec-butylsulphinyl, tert-butylsulphinyl, methyl-sulphonyl, ethylsulphonyl, n-propylsulphonyl, isopropylsulphonyl, n-butyl-sulphonyl, isobutylsulphonyl, sec-butylsulphonyl, tert-butylsulphonyl, vinyl, allyl, vinyloxy, allyloxy, methylcarbonyl, ethylcarbonyl, methoxycarbonyl, ethoxy-carbonyl, tert-butoxycarbonyl; trifluoromethyl, trifluoroethyl, trifluoromethoxy, tri-fluoroethoxy, 1,1,2,2-tetrafluoroethoxy, trifluoromethylthio, trifluoroethylthio, tri-fluoromethylsulphinyl, trifluoroethylsulphinyl, trifluoromethylsulphonyl, tri-fluoroethylsulphonyl, 2,2-difluorovinyl, 2,2-dichlorovinyl, trifluorovinyloxy, trifluoromethylcarbonyl, trifluoroethylcarbonyl, trifluoromethoxycarbonyl, trifluoro-ethoxycarbonyl, pentafluorothio, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$ or —OSO$_2$NR$^{13}$.

$R^6$, $R^7$, $R^8$ and $R^9$ independently of one another very particularly preferably represent hydrogen, fluorine, chlorine, methyl, ethyl, isopropyl, tert-butyl, methoxy, ethoxy, isopropoxy, tert-butoxy, methylthio, ethylthio, isopropylthio, tert-butylthio, methyl-sulphinyl, ethylsulphinyl, isopropylsulphinyl, tert-butylsulphinyl, methylsulphonyl, ethylsulphonyl, isopropylsulphonyl, tert-butylsulphonyl, vinyl, allyl, methylcarbonyl, methoxycarbonyl, trifluoromethyl, trifluoromethoxy, trifluoro-methylthio, dimethylaminosulphonyl, trifluoromethylcarbonyl, trifluoromethoxycarbonyl, dimethylamino, diethylamino, d diiso-n-propylamino, —N(Me)COMe, —N(Me)COEt, —N(Me)COPr, —N(Me)CO(tert-Bu), 2-pyrrolidon-5-yl, 2-piperidon-6-yl, —N(Me)SO$_2$Me, —N(Me)SO$_2$Et, —N(Me)SO$_2$CF$_3$, —N(Et)SO$_2$CF$_3$, —N(Me)SO$_2$(CF$_2$)$_3$CF$_3$ or —OSO$_2$NMe$_2$.

$R^6$, $R^7$, $R^8$ and $R^9$ independently of one another especially preferably represent hydrogen, fluorine, chlorine, methyl, methoxy, methylthio, trifluoromethyl, trifluoromethoxy, trifluoromethylthio, —SO$_2$NMe$_2$.

$R^6$, $R^7$, $R^8$ and $R^9$ independently of one another most preferably represent hydrogen.

$R^{10}$ preferably represents hydrogen, $C_1$-$C_4$-alkyl, $C_2$-$C_4$-alkenyl, $C_1$-$C_4$-haloalkyl having 1 to 9 fluorine, chlorine and/or bromine atoms, $C_2$-$C_4$-haloalkenyl having 1 to 7 fluorine, chlorine and/or bromine atoms, cyclopropyl, cyclopentyl or cyclohexyl.

$R^{10}$ particularly preferably represents hydrogen, methyl, ethyl or cyclopropyl.

$R^{10}$ very particularly preferably represents hydrogen, methyl or ethyl.

$R^{11}$ preferably represents hydrogen, $C_1$-$C_4$-alkyl, $C_2$-$C_4$-alkenyl, $C_1$-$C_4$-haloalkyl having 1 to 9 fluorine, chlorine and/or bromine atoms, $C_2$-$C_4$-haloalkenyl having 1 to 7 fluorine, chlorine and/or bromine atoms, $C_3$-$C_6$-cycloalkyl-$C_1$-$C_2$-alkyl or benzyl or phenylethyl, each of which is optionally mono- to tetrasubstituted by identical or different radicals $R^5$.

$R^{11}$ particularly preferably represents hydrogen, methyl, ethyl, cyclopropylmethyl or benzyl which is in each case optionally mono- to trisubstituted by identical or different radicals $R^5$.

$R^{11}$ very particularly preferably represents hydrogen, methyl or ethyl.

$R^{12}$ and $R^{13}$ independently of one another preferably represent hydrogen, $C_1$-$C_4$-alkyl, $C_1$-$C_4$-haloalkyl having 1 to 9 fluorine, chlorine and/or bromine atoms, $C_3$-$C_6$-cycloalkyl, $C_3$-$C_6$-cycloalkyl-$C_1$-$C_2$-alkyl or benzyl or phenylethyl, each of which is optionally mono- to tetrasubstituted by identical or different radicals $R^5$.

$R^{12}$ and $R^{13}$ furthermore together preferably represent $C_3$-$C_5$-alkylene, —(CH$_2$)$_2$—O—(CH$_2$)$_2$— or —(CH$_2$)$_2$—S—(CH$_2$)$_2$—.

$R^{12}$ and $R^{13}$ independently of one another particularly preferably represent hydrogen, methyl, ethyl, n-propyl, isopropyl, tert-butyl, trifluoromethyl, cyclopropylmethyl or benzyl which is in each case optionally mono- to trisubstituted by identical or different radicals $R^5$.

$R^{12}$ and $R^{13}$ furthermore together particularly preferably represent propylene, butylene, pentylene, —(CH$_2$)$_2$—O—(CH$_2$)$_2$— or —(CH$_2$)$_2$—S—(CH$_2$)$_2$—.

p preferably represents 0 or 1.

p particularly preferably represents 0.

Q preferably represents a completely unsaturated 5-membered heterocycle which has 1 to 3 identical or different heteroatoms from the group consisting of nitrogen, oxygen and sulphur and which is mono- or polysubstituted by identical or different radicals from the list $W^1$, and $W^1$ preferably represents fluorine, chlorine, bromine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_1$-$C_{12}$-haloalkoxy, $C_1$-$C_{12}$-haloalkylthio, $C_1$-$C_{12}$-haloalkylsulphinyl, $C_1$-$C_{12}$-haloalkylsulphonyl, $C_3$-$C_{12}$-cycloalkyl or represents phenyl or aryl-$C_1$-$C_2$-alkyl, each of which is optionally mono- or polysubstituted by identical or different substituents from the group consisting of fluorine, chlorine, bromine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$ or —OSO$_2$N$R^{12}R^{13}$.

Q particularly preferably represents a completely unsaturated 5-membered heterocycle from the group consisting of
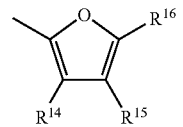 Q1
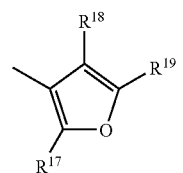 Q2
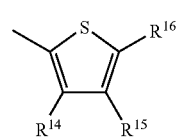 Q3
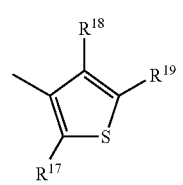 Q4
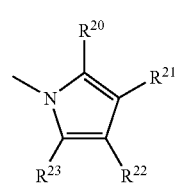 Q5
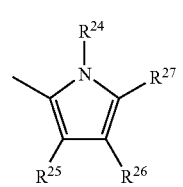 Q6
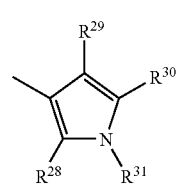 Q7
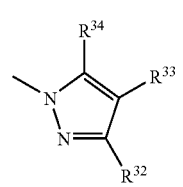 Q8
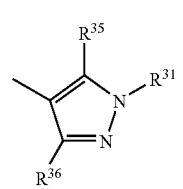 Q9
-continued
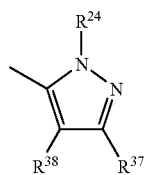 Q10
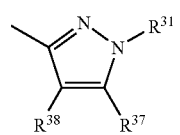 Q11
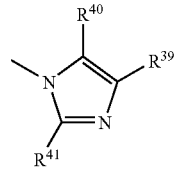 Q12
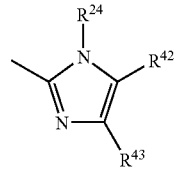 Q13
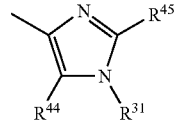 Q14
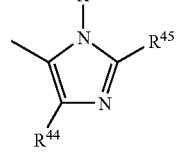 Q15
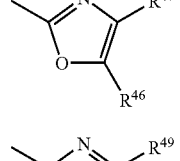 Q16
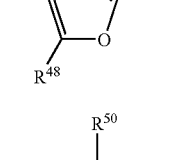 Q17
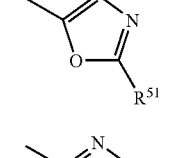 Q18
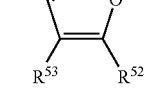 Q19

-continued

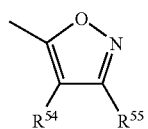 Q20

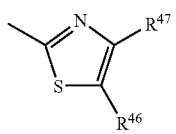 Q21

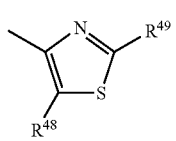 Q22

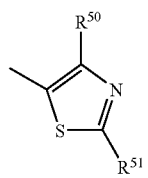 Q23

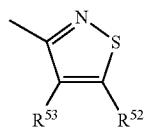 Q24

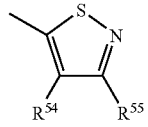 Q25

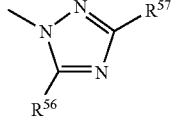 Q26

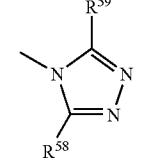 Q27

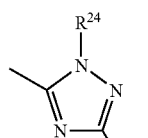 Q28

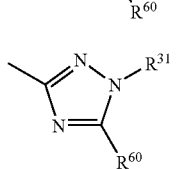 Q29

-continued

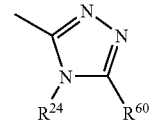 Q30

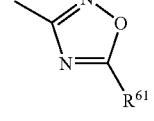 Q31

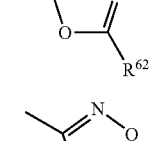 Q32

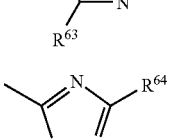 Q33

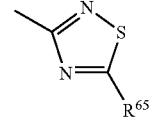 Q34

Q35

Q36

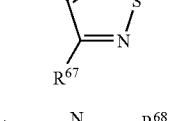 Q37

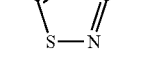 Q38 in which $R^{14}$ and $R^{15}$ independently of one another represent hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, $R^{16}$ represents hydrogen, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ areas defined above, with the proviso that $R^{14}$, $R^{15}$, $R^{16}$ do not simultaneously represent hydrogen, $R^{17}$ and $R^{19}$ independently of one another represent hydrogen, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-halo-alkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, $R^{18}$ represents hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, with the proviso that $R^{17}$, $R^{18}$, $R^{19}$ do not simultaneously represent hydrogen, $R^{20}$ and $R^{23}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, $R^{21}$ and $R^{22}$ independently of one another represent hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, with the proviso that $R^{20}$, $R^{21}$, $R^{22}$, $R^{23}$ do not simultaneously represent hydrogen, $R^{24}$ represents hydrogen, $C_1$-$C_6$-alkyl or $C_3$-$C_6$-cycloalkyl, $R^{25}$ and $R^{26}$ independently of one another represent hydrogen, chlorine, cyano, $C_1$-$C_{12}$-alkyl, $C_1$-$C_{12}$-alkoxy, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pN^{12}R^{13}$, $-(CH_2)_pN(R^{12})$ $COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, $R^{27}$ represents hydrogen, $C_1-C_{12}$-alkyl, $C_1-C_{12}$-alkoxy, $C_1-C_{12}$-haloalkyl, $C_3-C_{12}$-cyclo-alkyl or represents phenyl or benzyl, each of which is optionally mono- to tetrasubstituted by identical or different substituents from the group consisting of fluorine, chlorine, cyano, formyl, nitro, trimethylsilyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $C_2-C_4$-alkenyl, $C_2-C_4$-alkenyloxy, $(C_1-C_4$-alkyl)carbonyl, $(C_1-C_4$-alkoxy)carbonyl, $C_1-C_4$-haloalkyl, $C_1-C_4$-haloalkoxy, $C_1-C_4$-haloalkylthio, $C_1-C_4$-haloalkylsulphinyl, $C_1-C_4$-haloalkylsulphonyl having in each case 1 to 9 fluorine, chlorine and/or bromine atoms, $C_2-C_4$-haloalkenyl, $C_2-C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, with the proviso that $R^{24}$, $R^{25}$, $R^{26}$, $R^{27}$ do not simultaneously represent hydrogen, $R^{28}$ and $R^{30}$ independently of one another represent hydrogen, $C_1-C_{12}$-alkyl, $C_1-C_{12}$-alkoxy, $C_1-C_{12}$-haloalkyl, $C_3-C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $C_2-C_4$-alkenyl, $C_2-C_4$-alkenyloxy, $(C_1-C_4$-alkyl)carbonyl, $(C_1-C_4$-alkoxy)carbonyl, $C_1-C_4$-haloalkyl, $C_1-C_4$-haloalkoxy, $C_1-C_4$-haloalkylthio, $C_1-C_4$-haloalkylsulphinyl, $C_1-C_4$-haloalkylsulphonyl having in each case 1 to 9 fluorine, chlorine and/or bromine atoms, $C_2-C_4$-haloalkenyl, $C_2-C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, $R^{29}$ represents hydrogen, chlorine, cyano, $C_1-C_{12}$-alkyl, $C_1-C_{12}$-alkoxy, $C_1-C_{12}$-haloalkyl, $C_3-C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $C_2-C_4$-alkenyl, $C_2-C_4$-alkenyloxy, $(C_1-C_4$-alkyl)carbonyl, $(C_1-C_4$-alkoxy)carbonyl, $C_1-C_4$-haloalkyl, $C_1-C_4$-haloalkoxy, $C_1-C_4$-haloalkylthio, $C_1-C_4$-haloalkylsulphinyl, $C_1-C_4$-haloalkylsulphonyl having in each case 1 to 9 fluorine, chlorine and/or bromine atoms, $C_2-C_4$-haloalkenyl, $C_2-C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as above, $R^{31}$ represents hydrogen, $C_1-C_6$-alkyl, $C_3-C_6$-cycloalkyl, or represents phenyl or benzyl, each of which is optionally mono- to tetrasubstituted by identical or different substituents from the group consisting of fluorine, chlorine, cyano, formyl, nitro, trimethylsilyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $C_2-C_4$-alkenyl, $C_2-C_4$-alkenyloxy, $(C_1-C_4$-alkyl)carbonyl, $(C_1-C_4$-alkoxy)carbonyl, $C_1-C_4$-haloalkyl, $C_1-C_4$-haloalkoxy, $C_1-C_4$-haloalkylthio, $C_1-C_4$-haloalkylsulphinyl, $C_1-C_4$-haloalkylsulphonyl having in each case 1 to 9 fluorine, chlorine and/or bromine atoms, $C_2-C_4$-haloalkenyl, $C_2-C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, with the proviso that $R^{28}$, $R^{29}$, $R^{30}$, $R^{31}$ do not simultaneously represent hydrogen, $R^{32}$ and $R^{34}$ independently of one another represent hydrogen, $C_1-C_{12}$-alkyl, $C_1-C_{12}$-alkoxy, $C_1-C_{12}$-alkylthio, $C_1-C_{12}$-alkylsulphinyl, $C_1-C_{12}$-alkylsulphonyl, $C_1-C_{12}$-haloalkyl, $C_3-C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $C_2-C_4$-alkenyl, $C_2-C_4$-alkenyloxy, $(C_1-C_4$-alkyl)carbonyl, $(C_1-C_4$-alkoxy)carbonyl, $C_1-C_4$-haloalkyl, $C_1-C_4$-haloalkoxy, $C_1-C_4$-haloalkylthio, $C_1-C_4$-haloalkylsulphinyl, $C_1-C_4$-haloalkylsulphonyl having in each case 1 to 9 fluorine, chlorine and/or bromine atoms, $C_2-C_4$-haloalkenyl, $C_2-C_4$-haloalkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, $R^{33}$ represents hydrogen, chlorine, cyano, $C_1-C_{12}$-alkyl, $C_1-C_{12}$-alkoxy, $C_1-C_{12}$-alkylthio, $C_1-C_{12}$-alkylsulphinyl, $C_1-C_{12}$-alkylsulphonyl, $C_1-C_{12}$-haloalkyl, $C_3-C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $C_2-C_4$-alkenyl, $C_2-C_4$-alkenyloxy, $(C_1-C_4$-alkyl)carbonyl, $(C_1-C_4$-alkoxy)carbonyl, $C_1-C_4$-haloalkyl, $C_1-C_4$-haloalkoxy, $C_1-C_4$-haloalkylthio, $C_1-C_4$-haloalkylsulphinyl, $C_1-C_4$-haloalkylsulphonyl having in each case 1 to 9 fluorine, chlorine and/or bromine atoms, $C_2-C_4$-haloalkenyl, $C_2-C_4$-halo-alkenyloxy having in each case 1 to 7 fluorine, chlorine and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$ or $-OSO_2NR^{12}R^{13}$, where $R^{10}$ to $R^{13}$ are as defined above, with the proviso that $R^{32}$, $R^{33}$, $R^{34}$ do not simultaneously represent hydrogen, $R^{35}$ and $R^{36}$ independently of one another represent hydrogen, $C_1-C_{12}$-alkyl, $C_1-C_{12}$-alkoxy, $C_1-C_{12}$-alkylthio, $C_1-C_{12}$-alkylsulphinyl, $C_1-C_{12}$-alkylsulphonyl, $C_1-C_{12}$-haloalkyl, $C_3-C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $C_2-C_4$-alkenyl, $C_2-C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{31}$, $R^{35}$, $R^{36}$ do not simultaneously represent hydrogen, $R^{37}$ represents hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, $R^{38}$ represents hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —C($R^{10}$)=N—$OR^{11}$, —$SO_2NR^{12}R^{13}$, —$(CH_2)NR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{24}$, $R^{37}$, $R^{38}$ or $R^{31}$, $R^{37}$, $R^{38}$ do not simultaneously represent hydrogen, $R^{39}$, $R^{40}$ and $R^{41}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-halo-alkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{39}$, $R^{40}$, $R^{41}$ do not simultaneously represent hydrogen, $R^{42}$ and $R^{43}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_2$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{24}$, $R^{42}$, $R^{43}$ do not simultaneously represent hydrogen, $R^{44}$ and $R^{45}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{24}$, $R^{44}$, $R^{45}$ or $R^{31}$, $R^{44}$, $R^{45}$ do not simultaneously represent hydrogen, $R^{46}$ and $R^{47}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkyls ulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{46}$, $R^{47}$ do not simultaneously represent hydrogen, $R^{48}$ and $R^{49}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{48}$, $R^{49}$ do not simultaneously represent hydrogen, $R^{50}$ and $R^{51}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{50}$, $R^{51}$ do not simultaneously represent hydrogen, $R^{52}$ represents hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR_{13}$, —$(CH_2)_pN(R^{12})SO_2R^{13}$, —$OSO_2R^{12}$ or —$OSO_2NR^{12}R^{13}$, where $R^{10}$ to $R^{13}$ aee as defined above, $R^{53}$ represents hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{52}$, $R^{53}$ do not simultaneously represent hydrogen, $R^{54}$ represents hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are $R^{55}$ represents hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C^{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{54}$, $R^{55}$ do not simultaneously represent hydrogen, $R^{56}$ and $R^{57}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —$C(R^{10})$=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{56}$, $R^{57}$ do not simultaneously represent hydrogen, $R^{58}$ and $R^{59}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represent phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —$C(R^{10})$=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{58}$, $R^{59}$ do not simultaneously represent hydrogen, $R^{60}$ represents hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —$C(R^{10})$=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, with the proviso that $R^{24}$ and $R^{60}$ or $R^{31}$ and $R^{60}$ do not simultaneously represent hydrogen, $R^{61}$ represents $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —$C(R^{10})$=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, $R^{62}$ represents cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-halo-alkenyloxy having in each case 1 to 7 fluorine, chlorine and/or bromine atoms, —$C(R^{10})$=N—$OR^{11}$, —$SO_2NR^{12}R^{13}$, —$(CH_2)NR^{12}R^{13}$, —$(CH_2)_p(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, $R^{63}$ represents $C_1$-$C_{12}$-alkyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —$C(R^{10})$=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, $R^{64}$ represents $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, $R^{65}$ represents $C_1$-$C_{12}$-alkyl, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, $R^{66}$ represents $C_1$-$C_{12}$-alkyl, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, $R^{67}$ represents $C_1$-$C_{12}$-alkyl, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above, $R^{68}$ represents $C_1$-$C_{12}$-alkyl, $C_1$-$C_{12}$-alkoxy, $C_1$-$C_{12}$-haloalkyl, $C_3$-$C_{12}$-cycloalkyl or represents phenyl or benzyl, each of which is optionally mono- to tetrasubstituted by identical or different substituents from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine and/or bromine atoms, $C_2$-$C_4$-haloalkenyl, $C_2$-$C_4$-haloalkenyloxy having in each case 1 to 7 fluorine, chlorine and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ or —$OSO_2NR^{12}R^{13}$, where $R^{10}$ to $R^{13}$ are as defined above.

Q very particularly preferably represents a completely unsaturated 5-membered hetero-cycle from the group consisting of

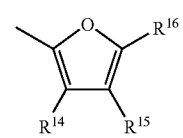

Q1

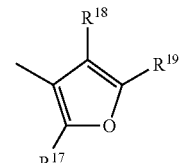

Q2

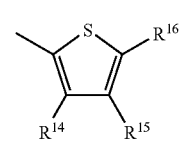

Q3

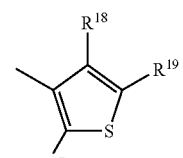

Q4

Q furthermore very particularly preferably represents a completely unsaturated 5-membered heterocycle from the group consisting of

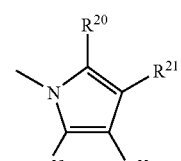

Q5

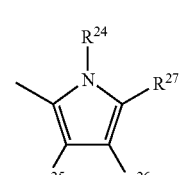

Q6

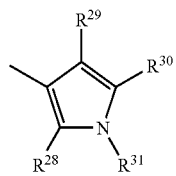  Q7

Q furthermore very particularly preferably represents a completely unsaturated 5-membered heterocycle from the group consisting of

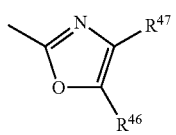  Q16

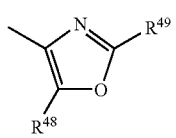  Q17

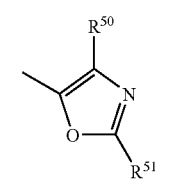  Q18

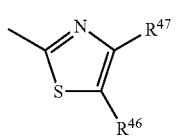  Q21

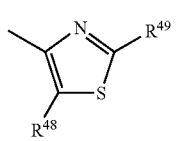  Q22

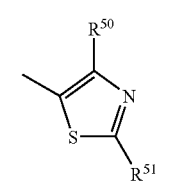  Q23

Q furthermore very particularly preferably represents a completely unsaturated 5-membered heterocycle from the group consisting of

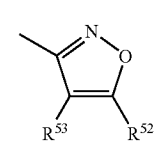  Q19

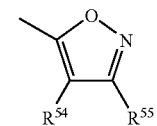  Q20

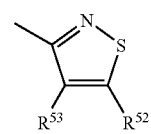  Q24

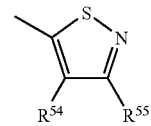  Q25

Q furthermore very particularly preferably represents a completely unsaturated 5-membered heterocycle from the group consisting of

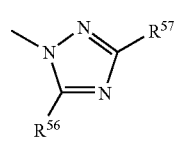  Q26

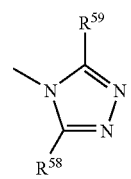  Q27

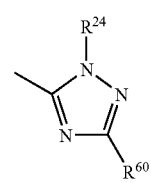  Q28

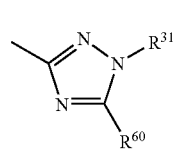  Q29

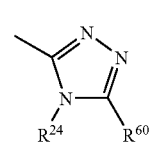  Q30

Q furthermore very particularly preferably represents a completely unsaturated 5-membered heterocycle from the group consisting of

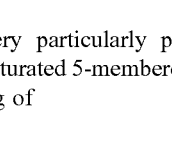  Q31

-continued

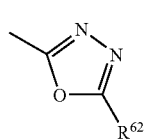
Q32

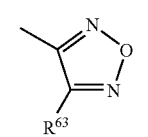
Q33

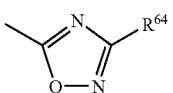
Q34

Q furthermore very particularly preferably represents a completely unsaturated 5-membered heterocycle from the group consisting of

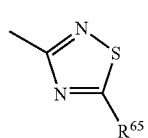
Q35

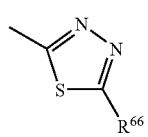
Q36

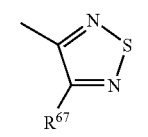
Q37

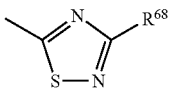
Q38

Q especially preferably represents a completely unsaturated 5-membered heterocycle from the group consisting of

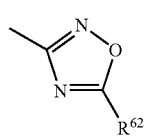
Q31

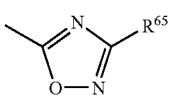
Q34

Q furthermore especially preferably represents a completely unsaturated 5-membered heterocycle from the group consisting of

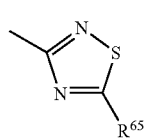
Q35

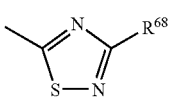
Q38

$R^{14}$ and $R^{15}$ independently of one another preferably represent hydrogen, chlorine, cyano, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkyl-sulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$R$^{13}$, or —OSO$_2$NR$^{12}$R$^{13}$, where $R^{10}$ to $R^{13}$ are as defined above.

$R^{14}$ and $R^{15}$ independently of one another particularly preferably represent hydrogen, chlorine, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methyl-thio, ethylthio, n-propylthio, isopropylthio, n-butylthio, tert-butylthio, trifluoro-methyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{14}$ and $R^{15}$ independently of one another very particularly preferably represent hydrogen, chlorine, cyano, methyl, ethyl, isopropyl, tert-butyl, neopentyl, methoxy, ethoxy, isopropoxy, tert-butoxy, methylthio, ethylthio, isopropylthio, tert-butylthio, tri-fluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{16}$ preferably represents hydrogen, cyano, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$R$^{13}$, or —OSO$_2$NR$^{12}$R$^{13}$, where $R^{10}$ to $R^{13}$ are as defined above.

$R^{16}$ particularly preferably represents hydrogen, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{16}$ very particularly preferably represents hydrogen, cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{11}$ and $R^{19}$ independently of one another preferably represent hydrogen, cyano, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —(CH$_2$)$_p$N($R^{12}$)SO$_2$R$^{13}$, or —OSO$_2$NR$^{12}$R$^{13}$, where $R^{10}$ to $R^{13}$ are as defined above.

$R^{17}$ and $R^{19}$ independently of one another particularly preferably represent hydrogen, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{17}$ and $R^{19}$ independently of one another very particularly preferably represent hydrogen, cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{18}$ preferably represents hydrogen, chlorine, cyano, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —(CH$_2$)$_p$N($R^{12}$)SO$_2$R$^{13}$, or —OSO$_2$NR$^{12}$R$^{13}$, where $R^{10}$ to $R^{13}$ are as defined above.

$R^{18}$ particularly preferably represents hydrogen, chlorine, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{18}$ very particularly preferably represents hydrogen, chlorine, cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{20}$ and $R^{23}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —(CH$_2$)$_p$N($R^{12}$)SO$_2$R$^{13}$, or —OSO$_2$NR$^{12}$R$^{13}$, where $R^{10}$ to $R^{13}$ are as defined above.

$R^{20}$ and $R^{23}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{20}$ and $R^{23}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{21}$ and $R^{22}$ independently of one another preferably represent hydrogen, chlorine, cyano, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkyl-sulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$R^{13}$, or —OSO$_2$NR$^{12}$R$^{13}$, where $R^{10}$ to $R^{13}$ are as defined above.

$R^{21}$ and $R^{22}$ independently of one another particularly preferably represent hydrogen, chlorine, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methyl-thio, ethylthio, n-propylthio, isopropylthio, n-butylthio, tert-butylthio, trifluoro-methyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{21}$ and $R^{22}$ independently of one another very particularly preferably represent hydrogen, chlorine, cyano, methyl, ethyl, isopropyl, tert-butyl, neopentyl, methoxy, ethoxy, isopropoxy, tert-butoxy, methylthio, ethylthio, isopropylthio, tert-butylthio, tri-fluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{24}$ preferably represents hydrogen, methyl, ethyl, n-propyl, isopropyl, n-butyl, isobutyl, sec-butyl, tert-butyl or cyclopropyl.

$R^{24}$ particularly preferably represents hydrogen, methyl, ethyl, n-propyl, isopropyl, n-butyl, tert-butyl or cyclopropyl.

$R^{24}$ very particularly preferably represents hydrogen, methyl or cyclopropyl.

$R^{25}$ and $R^{26}$ independently of one another preferably represent hydrogen, chlorine, cyano, $C_1$-$C_5$-alkyl, $C_1$-$C_5$-alkoxy, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$R^{13}$, or —OSO$_2$NR$^{12}$R$^{13}$, where $R^{10}$ to $R^{13}$ are as defined above.

$R^{25}$ and $R^{26}$ independently of one another particularly preferably represent hydrogen, chlorine, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, trifluoro-methyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{25}$ and $R^{26}$ independently of one another very particularly preferably represent hydrogen, chlorine, cyano, methyl, ethyl, isopropyl, tert-butyl, neopentyl, methoxy, ethoxy, isopropoxy, tert-butoxy, trifluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{27}$ preferably represents hydrogen, $C_1$-$C_5$-alkyl, $C_1$-$C_5$-alkoxy, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$R^{13}$, or —OSO$_2$NR$^{12}$R$^{13}$, where $R^{10}$ to $R^{13}$ are as defined above.

$R^{27}$ particularly preferably represents hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{27}$ very particularly preferably represents hydrogen, methyl, ethyl, isopropyl, tert-butyl, neopentyl, methoxy, ethoxy, isopropoxy, tert-butoxy, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{28}$ and $R^{30}$ independently of one another preferably represent hydrogen, $C_1$-$C_5$-alkyl, $C_1$-$C_5$-alkoxy, $C_1$-$C_5$-haloalkyl having 1 to 9 fluorine, chlorine and/or bromine atoms, $C_3$-$C_6$-cycloalkyl or
represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$R^{13}$, or —OSO$_2$N$R^{12}$R^{13}$, where $R^{10}$ to $R^{13}$ are as defined above.

$R^{28}$ and $R^{30}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or
represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{28}$ and $R^{30}$ independently of one another very particularly preferably represent hydrogen, methyl, ethyl, isopropyl, tert-butyl, neopentyl, methoxy, ethoxy, isopropoxy, tert-butoxy, trifluoromethyl or
represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{29}$ preferably represents hydrogen, chlorine, cyano, $C_1$-$C_5$-alkyl, $C_1$-$C_5$-alkoxy, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$R^{13}$, or —OSO$_2$N$R^{12}$R^{13}$, where $R^{10}$ to $R^{13}$ are as defined above.

$R^{29}$ particularly preferably represents hydrogen, chlorine, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, trifluoromethyl, cyclopropyl or
represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{29}$ very particularly preferably represents hydrogen, chlorine, cyano, methyl, ethyl, isopropyl, tert-butyl, neopentyl, methoxy, ethoxy, isopropoxy, tert-butoxy, trifluoromethyl or
represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{31}$ preferably represents hydrogen, methyl, ethyl, n-propyl, isopropyl, n-butyl, isobutyl, sec-butyl, tert-butyl or cyclopropyl or
represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$R^{13}$, or —OSO$_2$N$R^{12}$R^{13}$, where $R^{10}$ to $R^{13}$ are as defined above.

$R^{31}$ particularly preferably represents hydrogen, methyl, ethyl, n-propyl, isopropyl, n-butyl, tert-butyl or cyclopropyl or
represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{31}$ very particularly preferably represents hydrogen, methyl or cyclopropyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{32}$ and $R^{34}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —(CH$_2$)$_p$N($R^{12}$)SO$_2R^{13}$, or —OSO$_2$NR$^{12}R^{13}$, where $R^{10}$ to $R^{13}$ are as defined above.

$R^{32}$ and $R^{34}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{32}$ and $R^{34}$ independently of one another very particularly preferably represent hydrogen, chlorine, cyano, methyl, ethyl, isopropyl, tert-butyl, neopentyl, methoxy, ethoxy, isopropoxy, tert-butoxy, methylthio, ethylthio, isopropylthio, tert-butylthio, tri-fluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{33}$ preferably represents hydrogen, chlorine, cyano, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —(CH$_2$)$_p$N($R^{12}$)SO$_2R^{13}$, or —OSO$_2$NR$^{12}R^{13}$, where $R^{10}$ to $R^{13}$ are as defined above.

$R^{33}$ particularly preferably represents hydrogen, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{33}$ very particularly preferably represents hydrogen, cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{35}$ and $R^{36}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —(CH$_2$)$_p$N($R^{12}$)SO$_2R^{13}$, or —OSO$_2$NR$^{12}R^{13}$, where $R^{10}$ to $R^{13}$ are as defined above.

$R^{35}$ and $R^{36}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{35}$ and $R^{36}$ independently of one another very particularly preferably represent hydrogen, chlorine, cyano, methyl, ethyl, isopropyl, tert-butyl, neopentyl, methoxy, ethoxy, isopropoxy, tert-butoxy, methylthio, ethylthio, isopropylthio, tert-butylthio, tri-fluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{37}$ preferably represents hydrogen, $C_1$-$C_5$-alkyl, $C_{-C5}$-alkoxy, $C_1$-$C_5$-alkylthio, $C_1$-$C_5$-alkylsulphinyl, $C_1$-$C_5$- alkylsulphonyl, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_pN(R^{12})SO_2R^{13}$, or —$OSO_2NR^{12}R^{13}$, where $R^{10}$ to $R^{13}$ are as defined above.

$R^{37}$ particularly preferably represents hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{37}$ very particularly preferably represents hydrogen, chlorine, cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{38}$ preferably represents hydrogen, chlorine, cyano, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_pN(R^{12})SO_2R^{13}$, or —$OSO_2NR^{12}R^{13}$, where $R^{10}$ to $R^{13}$ are as defined above.

$R^{38}$ particularly preferably represents hydrogen, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{38}$ very particularly preferably represents hydrogen, cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{39}$, $R^{40}$ and $R^{41}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_pN(R^{12})SO_2R^{13}$, or —$OSO_2NR^{12}R^{13}$, where $R^{10}$ to $R^{13}$ are as defined above.

$R^{39}$, $R^{40}$ and $R^{41}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{39}$, $R^{40}$ and $R^{41}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, tri-fluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{42}$ and $R^{43}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_pN(R^{12})SO_2R^{13}$, or —$OSO_2NR^{12}R^{13}$, where $R^{10}$ to $R^{13}$ are as defined above.

$R^{42}$ and $R^{43}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{42}$ and $R^{43}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{44}$ and $R^{45}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_pN(R^{12})SO_2R^{13}$, or —$OSO_2NR^{12}R^{13}$, where $R^{10}$ to $R^{13}$ are as defined above.

$R^{44}$ and $R^{45}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{44}$ and $R^{45}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{46}$ and $R^{47}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_pN(R^{12})SO_2R^{13}$, or —$OSO_2NR^{12}R^{13}$, where $R^{10}$ to $R^{13}$ are as defined above.

$R^{46}$ and $R^{47}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{46}$ and $R^{47}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{48}$ and $R^{49}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_p$N($R^{12}$)$SO_2R^{13}$, or —$OSO_2NR^{12}R^{13}$, where $R^{10}$ to $R^{13}$ are as defined above.

$R^{48}$ and $R^{49}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{48}$ and $R^{49}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or
represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{50}$ and $R^{51}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or
represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_p$N($R^{12}$)$SO_2R^{13}$, or —$OSO_2NR^{12}R^{13}$, where $R^{10}$ to $R^{13}$ are as defined above.

$R^{50}$ and $R^{51}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or
represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{50}$ and $R^{51}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or
represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{52}$ preferably represents hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or
represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—$OR^{11}$, —$(CH_2)_p$N($R^{12}$)$SO_2R^{13}$, or —$OSO_2NR^{12}R^{13}$, where $R^{10}$ to $R^{13}$ are as defined above.

$R^{52}$ particularly preferably represents hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or
represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—$OCH_3$, —C($CH_3$)=N—$OCH_3$, —C(H)=N—$OC_2H_5$, —C($CH_3$)=N—$OC_2H_5$, —N(H)$SO_2CH_3$, —N($CH_3$)$SO_2CH_3$, —N(H)$SO_2CF_3$, —N($CH_3$)$SO_2CF_3$, —$OSO_2N(CH_3)_2$ or —$OSO_2N(H)CH_3$.

$R^{52}$ very particularly preferably represents hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or
represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{53}$ preferably represents hydrogen, chlorine, cyano, $C_1$-$C_5$-alkyl, $C_1$-$C_5$-alkoxy, $C_1$-$C^5$-alkylthio, $C_1$-$C_5$-alkylsulphinyl, $C_1$-$C_5$-alkylsulphonyl, $C_1$-$C^5$-haloalkyl having 1 to 9 fluorine, chlorine and/or bromine atoms, $C_3$-$C_6$Cycloalkyl or
represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$$R^{13}$, or —OSO$_2$N$R^{12}$$R^{13}$, where $R^{10}$ to $R^{13}$ are as defined above.

$R^{53}$ particularly preferably represents hydrogen, chlorine, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{53}$ very particularly preferably represents hydrogen, chlorine, cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{54}$ independently of one another preferably represents hydrogen, chlorine, cyano, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkyl-sulphonyl, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$$R^{13}$, or —OSO$_2$N$R^{12}$$R^{13}$, where $R^{10}$ to $R^{13}$ are as defined above.

$R^{54}$ particularly preferably represents hydrogen, chlorine, cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{54}$ very particularly preferably represents hydrogen, chlorine, cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{55}$ preferably represents hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$$R^{13}$, or —OSO$_2$N$R^{12}$$R^{13}$, where $R^{10}$ to $R^{13}$ are as defined above.

$R^{55}$ particularly preferably represents hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{55}$ very particularly preferably represents hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{56}$ and $R^{57}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —$(CH_2)_pN(R^{12})SO_2R^{13}$, or —$OSO_2NR^{12}R^{13}$, where $R^{10}$ to $R^{13}$ are as defined above.

$R^{56}$ and $R^{57}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —$C(H)$=$N$—$OCH_3$, —$C(CH_3)$=$N$—$OCH_3$, —$C(H)$=$N$—$OC_2H_5$, —$C(CH_3)$=$N$—$OC_2H_5$, —$N(H)SO_2CH_3$, —$N(CH_3)SO_2CH_3$, —$N(H)SO_2CF_3$, —$N(CH_3)SO_2CF_3$, —$OSO_2N(CH_3)_2$ or —$OSO_2N(H)CH_3$.

$R^{56}$ and $R^{57}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{58}$ and $R^{59}$ independently of one another preferably represent hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represent phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —$C(R^{10})$=$N$—$OR^{11}$, —$(CH_2)_pN(R^{12})SO_2R^{13}$, or —$OSO_2NR^{12}R^{13}$, where $R^{10}$ to $R^{13}$ are as defined above.

$R^{58}$ and $R^{59}$ independently of one another particularly preferably represent hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represent phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —$C(H)$=$N$—$OCH_3$, —$C(CH_3)$=$N$—$OCH_3$, —$C(H)$=$N$—$OC_2H_5$, —$C(CH_3)$=$N$—$OC_2H_5$, —$N(H)SO_2CH_3$, —$N(CH_3)SO_2CH_3$, —$N(H)SO_2CF_3$, —$N(CH_3)SO_2CF_3$, —$OSO_2N(CH_3)_2$ or —$OSO_2N(H)CH_3$.

$R^{58}$ and $R^{59}$ independently of one another very particularly preferably represent hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represent phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{60}$ preferably represents hydrogen, $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$-cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —$C(R^{10})$=$N$—$OR^{11}$, —$(CH_2)_pN(R^{12})SO_2R^{13}$, or —$OSO_2NR^{12}R^{13}$, where $R^{10}$ to $R^{13}$ are as defined above.

$R^{60}$ particularly preferably represents hydrogen, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —$C(H)$=$N$—$OCH_3$, —$C(CH_3)$=$N$—$OCH_3$, —$C(H)$=$N$—$OC_2H_5$, —$C(CH_3)$=$N$—$OC_2H_5$, —$N(H)SO_2CH_3$, —$N(CH_3)SO_2CH_3$, —$N(H)SO_2CF_3$, —$N(CH_3)SO_2CF_3$, —$OSO_2N(CH_3)_2$ or —$OSO_2N(H)CH_3$.

$R^{60}$ very particularly preferably represents hydrogen, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{61}$ preferably represents $C_1$-$C_5$-alkyl, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-haloalkyl having 1 to 9 fluorine, chlorine and/or bromine atoms, $C_3$-$C_6$Cycloalkyl or represents phenyl or benzyl, each of which is optionally mono- to tetrasubstituted by identical or different substituents from the group consisting of chlorine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —$C(R^{10})$=$N$—$OR^{11}$, —$(CH_2)_pN(R^{12})SO_2R^{13}$, or —$OSO_2NR^{12}R^{13}$, where $R^{10}$ to $R^{13}$ are as defined above.

$R^{61}$ particularly preferably represents methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{61}$ very particularly preferably represents methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{62}$ preferably represents cyano, C$_1$-C$_5$-alkyl, C$_1$-C$_5$-alkoxy, C$_1$-C$_5$-alkylthio, C$_1$-C$_5$-alkylsulphinyl, C$_1$-C$_5$-alkylsulphonyl, C$_1$-C$_5$-haloalkyl having 1 to 9 fluorine, chlorine and/or bromine atoms, C$_3$-C$_6$-cycloalkyl or represents phenyl or benzyl, each of which is optionally mono- to tetrasubstituted by identical or different substituents from the group consisting of chlorine, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, methylcarbonyl, ethylcarbonyl, methoxycarbonyl, ethoxycarbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkyl-sulphonyl having in each case 1 to 9 fluorine, chlorine and/or bromine atoms, —C(R$^{10}$)=N—OR$^{11}$, —(CH$_2$)$_p$N(R$^{12}$)SO$_2$R$^{13}$, or —OSO$_2$NR$^{12}$R$^{13}$, where R$^{10}$ to R$^{13}$ are as defined above.

$R^{62}$ particularly preferably represents cyano, methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{62}$ very particularly preferably represents cyano, methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{63}$ preferably represents C$_1$-C$_5$-alkyl, C$_1$-C$_5$-haloalkyl having 1 to 9 fluorine, chlorine and/or bromine atoms, C$_3$-C$_6$Cycloalkyl or represents phenyl or benzyl, each of which is optionally mono- to tetrasubstituted by identical or different substituents from the group consisting of chlorine, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, methylcarbonyl, ethylcarbonyl, methoxycarbonyl, ethoxycarbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkyl-sulphonyl having in each case 1 to 9 fluorine, chlorine and/or bromine atoms, —C(R$^{10}$)=N—OR$^{11}$, —(CH$_2$)$_p$N(R$^{12}$)SO$_2$R$^{13}$, or —OSO$_2$NR$^{12}$R$^{13}$, where R$^{10}$ to R$^{13}$ are as defined above.

$R^{63}$ particularly preferably represents methyl, ethyl, n-propyl, isopropyl, n-butyl, tert-butyl, n-pentyl, neopentyl, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{63}$ very particularly preferably represents methyl, ethyl, isopropyl, tert-butyl, neopentyl, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

$R^{64}$ preferably represents C$_1$-C$_5$-alkyl, C$_1$-C$_5$-alkoxy, C$_1$-C$_5$-alkylthio, C$_1$-C$_5$-alkylsulphinyl, C$_1$-C$_5$-alkylsulphonyl, C$_1$-C$_5$-haloalkyl having 1 to 9 fluorine, chlorine and/or bromine atoms, C$_3$-C$_6$-cycloalkyl or represents phenyl or benzyl, each of which is optionally mono- to tetrasubstituted by identical or different substituents from the group consisting of chlorine, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, methylcarbonyl, ethylcarbonyl, methoxycarbonyl, ethoxycarbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkyl-sulphonyl having in each case 1 to 9 fluorine, chlorine and/or bromine atoms, —C(R$^{10}$)=N—OR$^{11}$, —(CH$_2$)$_p$N(R$^{12}$)SO$_2$R$^{13}$, or —OSO$_2$NR$^{12}$R$^{13}$, where R$^{10}$ to R$^{13}$ are as defined above.

$R^{64}$ particularly preferably represents methyl, ethyl, n-propyl, isopropyl, n-butyl, tert-butyl, n-pentyl, neopentyl, methoxy, ethoxy, n-propoxy, isopropoxy, n-butoxy, tert-butoxy, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

R$^{64}$ very particularly preferably represents methyl, ethyl, isopropyl, tert-butyl, neopentyl, methoxy, ethoxy, isopropoxy, tert-butoxy, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

R$^{65}$ preferably represents C$_1$-C$_5$-alkyl, C$_1$-C$_5$-alkylthio, C$_1$-C$_5$-alkylsulphinyl, C$_1$-C$_5$-alkylsulphonyl, C$_1$-C$_5$-haloalkyl having 1 to 9 fluorine, chlorine and/or bromine atoms, C$_3$-C$_6$-cycloalkyl or represents phenyl or benzyl, each of which is optionally mono- to tetrasubstituted by identical or different substituents from the group consisting of chlorine, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, methylcarbonyl, ethylcarbonyl, methoxycarbonyl, ethoxycarbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkyl-sulphonyl having in each case 1 to 9 fluorine, chlorine and/or bromine atoms, —C(R$^{10}$)=N—OR$^{11}$, —(CH$_2$)$_p$N(R$^{12}$)SO$_2$R$^{13}$, or —OSO$_2$NR$^{12}$R$^{13}$, where R$^{10}$ to R$^{13}$ are as defined above.

R$^{65}$ particularly preferably represents methyl, ethyl, n-propyl, isopropyl, n-butyl, tert-butyl, n-pentyl, neopentyl, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

R$^{65}$ very particularly preferably represents methyl, ethyl, isopropyl, tert-butyl, neopentyl, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

R$^{66}$ preferably represents C$_1$-C$_5$-alkyl, C$_1$-C$_5$-alkylthio, C$_1$-C$_5$-alkylsulphinyl, C$_1$-C$_5$-alkylsulphonyl, C$_1$-C$_5$-haloalkyl having 1 to 9 fluorine, chlorine and/or bromine atoms, C$_3$-C$_6$-cycloalkyl or represents phenyl or benzyl, each of which is optionally mono- to tetrasubstituted by identical or different substituents from the group consisting of chlorine, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, methylcarbonyl, ethylcarbonyl, methoxycarbonyl, ethoxycarbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkyl-sulphonyl having in each case 1 to 9 fluorine, chlorine and/or bromine atoms, —C(R$^{10}$)=N—OR$^{11}$, —(CH$_2$)$_p$N(R$^{12}$)SO$_2$R$^{13}$, or —OSO$_2$NR$^{12}$R$^{13}$, where R$^{10}$ to R$^{13}$ are as defined above.

R$^{66}$ particularly preferably represents methyl, ethyl, n-propyl, isopropyl, n-butyl, tert-butyl, n-pentyl, neopentyl, methylthio, ethylthio, n-propylthio, isopropylthio, n-butylthio, tert-butylthio, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

R$^{66}$ very particularly preferably represents methyl, ethyl, isopropyl, tert-butyl, neopentyl, methylthio, ethylthio, isopropylthio, tert-butylthio, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

R$^{67}$ preferably represents C$_1$-C$_5$-alkyl, C$_1$-C$_5$-haloalkyl having 1 to 9 fluorine, chlorine and/or bromine atoms, C$_3$-C$_6$Cycloalkyl or represents phenyl or benzyl, each of which is optionally mono- to tetrasubstituted by identical or different substituents from the group consisting of chlorine, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, methylcarbonyl, ethylcarbonyl, methoxycarbonyl, ethoxycarbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkyl-sulphonyl having in each case 1 to 9 fluorine, chlorine and/or bromine atoms, —C(R$^{10}$)=N—OR$^{11}$, —(CH$_2$)$_p$N(R$^{12}$)SO$_2$R$^{13}$, or —OSO$_2$NR$^{12}$R$^{13}$, where R$^{10}$ to R$^{13}$ are as defined above.

R$^{67}$ particularly preferably represents methyl, ethyl, n-propyl, isopropyl, n-butyl, tert-butyl, n-pentyl, neopentyl, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

R$^{67}$ very particularly preferably represents methyl, ethyl, isopropyl, tert-butyl, neopentyl, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

R$^{68}$ preferably represents C$_1$-C$_5$-alkyl, C$_1$-C$_5$-alkoxy, C$_1$-C$_5$-haloalkyl having 1 to 9 fluorine, chlorine and/or bromine atoms, C$_3$-C$_6$-cycloalkyl or represents phenyl or benzyl, each of which is optionally mono- to tetrasubstituted by identical or different substituents from the group consisting of chlorine, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, methylcarbonyl, ethylcarbonyl, methoxycarbonyl, ethoxycarbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkyl-sulphonyl having in each case 1 to 9 fluorine, chlorine and/or bromine atoms, —C($R^{10}$)=N—O$R^{11}$, —(CH$_2$)$_p$N($R^{12}$)SO$_2$$R^{13}$, or —OSO$_2$NR$^{12}$R$^{13}$, where $R^{10}$ to $R^{13}$ are as defined above.

$R^{68}$ particularly preferably represents methyl, ethyl, n-propyl, isopropyl, n-butyl, tert-butyl, n-pentyl, neopentyl, methoxy, ethoxy, n-propoxy, isopropoxy, n-butoxy, tert-butoxy, trifluoromethyl, cyclopropyl or represents phenyl or benzyl, each of which is optionally mono- to tetrasubstituted by identical or different substituents from the group consisting of fluorine, chlorine, methyl, ethyl, n-propyl, isopropyl, n-butyl, tert-butyl, methoxy, ethoxy, n-propoxy, isopropoxy, n-butoxy, tert-butoxy, methylthio, ethylthio, n-propylthio, isopropylthio, n-butylthio, tert-butylthio, —C(H)=N—OCH$_3$, —C(CH$_3$)=N—OCH$_3$, —C(H)=N—OC$_2$H$_5$, —C(CH$_3$)=N—OC$_2$H$_5$, —N(H)SO$_2$CH$_3$, —N(CH$_3$)SO$_2$CH$_3$, —N(H)SO$_2$CF$_3$, —N(CH$_3$)SO$_2$CF$_3$, —OSO$_2$N(CH$_3$)$_2$ or —OSO$_2$N(H)CH$_3$.

$R^{68}$ very particularly preferably represents methyl, ethyl, isopropyl, tert-butyl, neopentyl, methoxy, ethoxy, isopropoxy, tert-butoxy, trifluoromethyl or represents phenyl or benzyl, each of which is optionally mono- or disubstituted by identical or different substituents from the group consisting of fluorine, chlorine, methyl, ethyl, isopropyl, tert-butyl, methoxy, ethoxy, isopropoxy, tert-butoxy.

In each case, the radical definitions $R^{14}$ to $R^{68}$ have to be chosen such that the heterocycles Q1 to Q38 are at least monosubstituted, that is the possible substitution positions may not simultaneously represent hydrogen. The corresponding measures are explicitly stated in the general part; however, they are not repeated in the presentation of the preferred definitions.

Preference is furthermore given to compounds of the formula (I) in which $R^1$ represents fluorine, $R^2$ represents fluorine and $R^3$ represents hydrogen.

Preference is furthermore given to compounds of the formula (I) in which $R^1$ represents fluorine, $R^2$ represents chlorine and $R^3$ represents hydrogen.

Preference is furthermore given to compounds of the formula (I) in which $R^1$ represents fluorine, $R^2$ represents hydrogen and $R^3$ represents hydrogen.

Preference is furthermore given to compounds of the formula (I) in which $R^1$ represents chlorine, $R^2$ represents hydrogen and $R^3$ represents hydrogen.

Preference is furthermore given to compounds of the formula (I) in which $R^1$ represents methyl, $R^2$ represents hydrogen and $R^3$ represents hydrogen.

Preference is furthermore given to compounds of the formula (I) in which $R^1$ represents chlorine, $R^2$ represents hydrogen and $R^3$ represents fluorine.

Preference is furthermore given to compounds of the formula (I) in which $A^1$ represents N.

Preference is furthermore given to compounds of the formula (I) in which $A^1$ represents CH.

Preference is furthermore given to compounds of the formula (I) in which $A^2$ represents N.

Preference is furthermore given to compounds of the formula (I) in which $A^2$ represents $CR^9$.

Preference is furthermore given to compounds of the formula (I) in which $A^2$ represents CH.

Preference is furthermore given to compounds of the formula (I) in which $A^1$ represents N and $A^2$ represents N.

Preference is furthermore given to compounds of the formula (I) in which $A^1$ represents N and $A^2$ represents $CR^9$.

Preference is furthermore given to compounds of the formula (I) in which $A^1$ represents N and $A^2$ represents CH.

Preference is furthermore given to compounds of the formula (I) in which $A^1$ represents CH and $A^2$ represents N.

Preference is furthermore given to compounds of the formula (I) in which $A^1$ represents CH and $A^2$ represents $CR^9$.

Preference is furthermore given to compounds of the formula (I) in which $A^1$ represents CH and $A^2$ represents CH.

Preference is furthermore given to compounds of the formula (I) in which

Q represents an unsaturated aromatic 5-membered heterocycle from the group consisting of

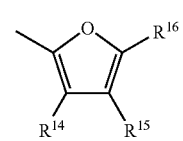

Q1

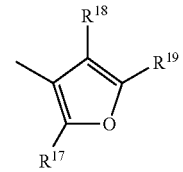

Q2

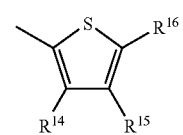

Q3

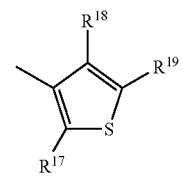

Q4

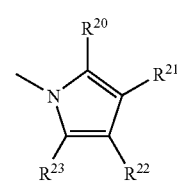

Q5

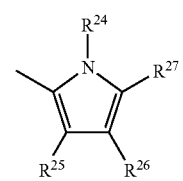

Q6

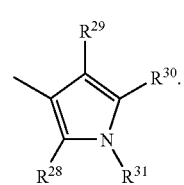

Q7

Preference is furthermore given to compounds of the formula (I) in which

Q represents an unsaturated aromatic 5-membered heterocycle from the group consisting of

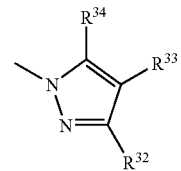
Q8

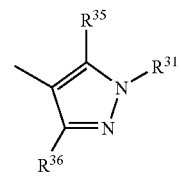
Q9

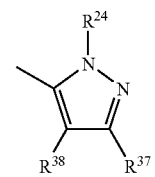
Q10

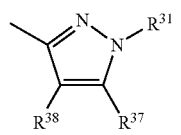
Q11

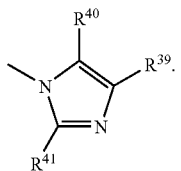
Q12

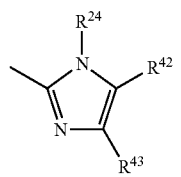
Q13

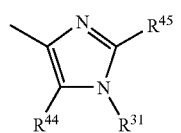
Q14

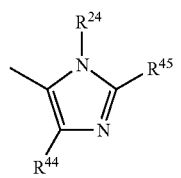
Q15

Preference is furthermore given to compounds of the formula (I) in which

Q represents an unsaturated aromatic 5-membered heterocycle from the group consisting of

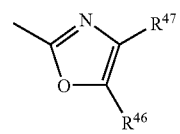
Q16

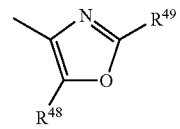
Q17

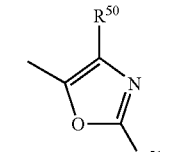
Q18

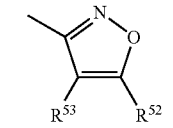
Q19

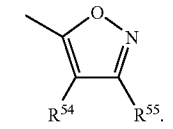
Q20

Preference is furthermore given to compounds of the formula (I) in which

Q represents an unsaturated aromatic 5-membered heterocycle from the group consisting of

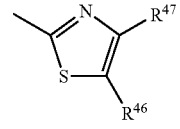
Q21

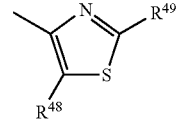
Q22

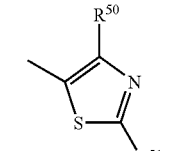
Q23

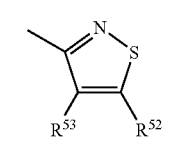
Q24

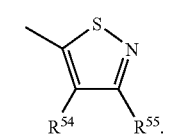
Q25

Preference is furthermore given to compounds of the formula (I) in which

Q represents an unsaturated aromatic 5-membered heterocycle from the group consisting of

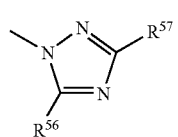
Q26

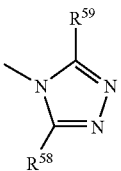
Q27

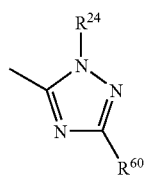
Q28

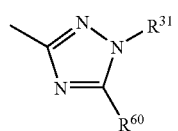
Q29

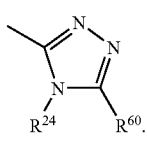
Q30.

Preference is furthermore given to compounds of the formula (I) in which

Q represents an unsaturated aromatic 5-membered heterocycle from the group consisting of

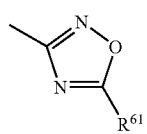
Q31

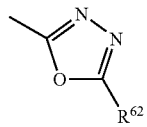
Q32

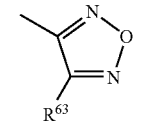
Q33

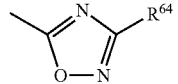
Q34

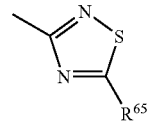
Q35

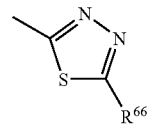
Q36

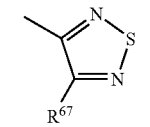
Q37

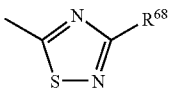
Q38.

Preference is furthermore given to compounds of the formula (I) in which $A^1$ and $A^2$ each represent CH and Q represents an unsaturated aromatic 5-membered heterocycle from the group consisting of

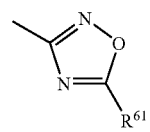
Q31

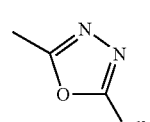
Q32

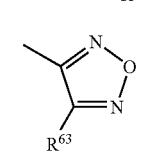
Q33

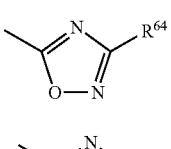
Q34

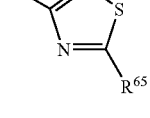
Q35

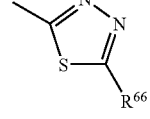
Q36

Preference is furthermore given to compounds of the formula (I) in which

R⁴ represents hydrogen, methoxycarbonyl or ethoxycarbonyl,

A¹ and A² each represent CH and

Q represents an unsaturated aromatic 5-membered heterocycle from the group consisiting of

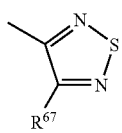
Q31

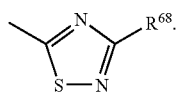
Q32

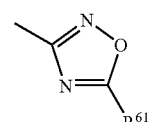
Q31

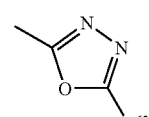
Q32

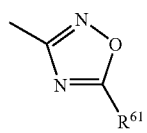
Q33

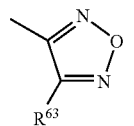
Q33

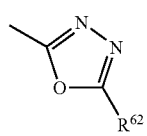
Q34

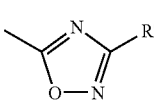
Q34

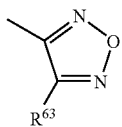
Q35

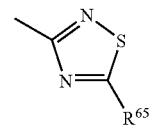
Q35

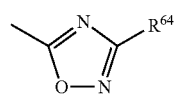
Q36

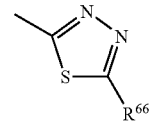
Q36

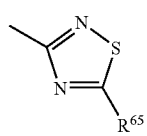
Q37

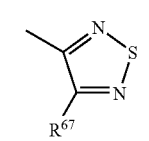
Q37

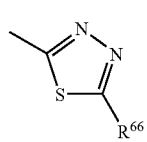
Q38

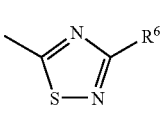
Q38 and $R^{62}$, $R^{63}$, $R^{64}$, $R^{65}$ independently of one another represent methyl, tert-butyl or trifluoro-metyl.

Preference is furthermore given to compounds of the formula (I) in which

R¹ represents fluorine, chlorine or methyl,

R² represents hydrogen or fluorine,

R³ represents hdrogen or fluorine,

R⁴ represents hdrogen, methoxycarbonyl or ethoxycarbonyl,

A¹ and A² each represent CH and

-continued

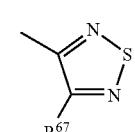
Q37

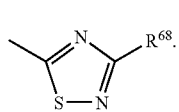
Q38

Preference is furthermore given to compounds of the formula (I) in which

R⁴ represents hydrogen, methoxycarbonyl or ethoxycarbonyl,

A¹ and A² each represent CH and

Q represents an unsaturated aromatic 5-membered heterocycle from the group consisting of Q represents an unsaturated aromatic 5-membered heterocycle from the group consisting of

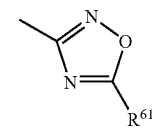 Q31

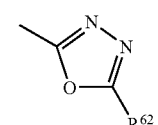 Q32

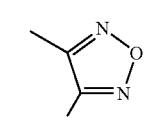 Q33

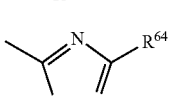 Q34

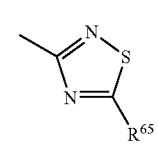 Q35

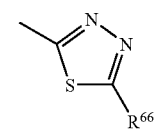 Q36

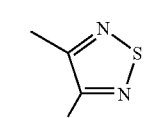 Q37

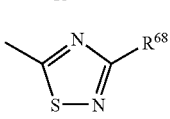 Q38 and $R^{62}$, $R^{63}$, $R^{64}$, $R^{65}$ independently of one another represent methyl, tert-butyl or trifluoro-methyl.

Preference is furthermore given to compounds of the formula (I-a):

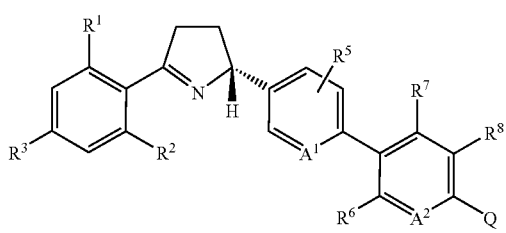
(I-a)

in which $R^1$, $R^2$, $R^3$, $A^1$, $A^2$, $R^5$, $R^6$, $R^7$, $R^8$ and Q are as defined above and the carbon atom in the 2-position of the 2H-pyrrole ring has the R configuration.

Preference is furthermore given to compounds of the formulae (I-b) and (I-c):

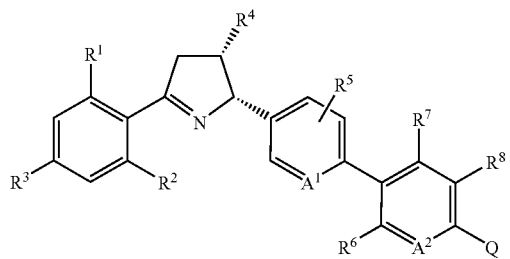
(I-b)

(I-c)

in which $R^1$, $R^2$, $R^3$, $A^1$, $A^2$, $R^5$, $R^6$, $R^7$, $R^8$ and Q are as defined above, $R^4$ does not represent hydrogen and the two substituents in the 2- and 3-positions of the 2H-pyrrole ring are in each case cis to one another.

Preference is furthermore given to compounds of the formulae (I-d) and (I-e):

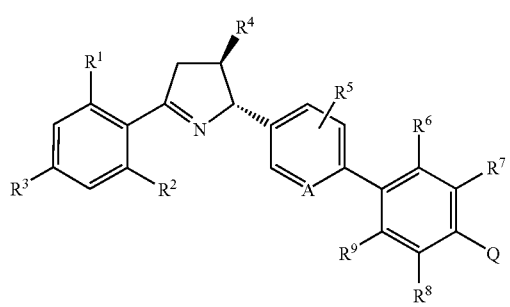
(I-d)

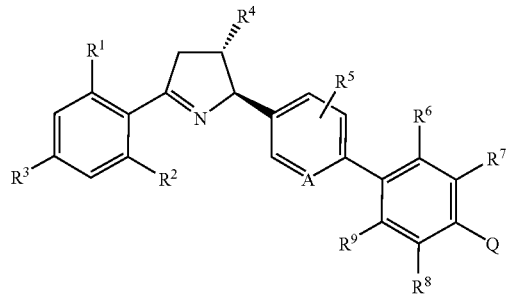
(I-e)

in which $R^1$, $R^2$, $R^3$, $A^1$, $A^2$, $R^5$, $R^6$, $R^7$, $R^8$ and Q are as defined above, $R^4$ does not represent hydrogen and the two substituents in the 2- and 3-positions of the 2H-pyrrole ring are in each case trans to one another.

Compounds of the formula (I-a) are obtained by customary methods for resolving racemates, such as, for example, by chromatography of the corresponding racemates on a chiral stationary phase. In this manner, it is possible to resolve both the racemic end products or racemic intermediates into the two enantiomers.

Saturated hydrocarbon radicals, such as alkyl, can in each case be straight-chain or branched as far as this is possible—including in combination with heteroatoms, such as, for example, in alkoxy.

Halogen-substituted radicals, for example haloalkyl, are mono- or polysubstituted, up to the maximum number of substituents possible. In the case of polyhalogenation, the halogen atoms can be identical or different. Here, halogen represents fluorine, chlorine, bromine or iodine, in particular fluorine, chlorine or bromine.

Preference, particular preference and very particular preference is given to compounds carrying the substituents mentioned under preferred, particularly preferred and very particularly preferred, respectively.

Saturated or unsaturated hydrocarbon radicals, such as alkyl or alkenyl, can in each case be straight-chain or branched as far as this is possible—including in combination with heteroatoms, such as, for example, in alkoxy.

Optionally substituted radicals may be mono- or polysubstituted, where in the case of polysubstitution the substituents may be identical or different.

However, the general or preferred radical definitions or illustrations given above can also be combined with one another as desired, i.e. between the respective ranges and preferred ranges. They apply to the end products and, correspondingly, to the precursors and intermediates.

Using 5-(2,6-difluorophenyl)-2-[2-fluoro-4-(4,4,5,5-tetramethyl-1,3,2-dioxaborolan-2-yl)phenyl]-3,4-dihydro-2H-pyrrole and 5-(4-bromophenyl)-3-tert-butyl-1,2,4-oxadiazole as starting materials and a catalyst, the course of the process (A) according to the invention can be illustrated by the formula scheme below.

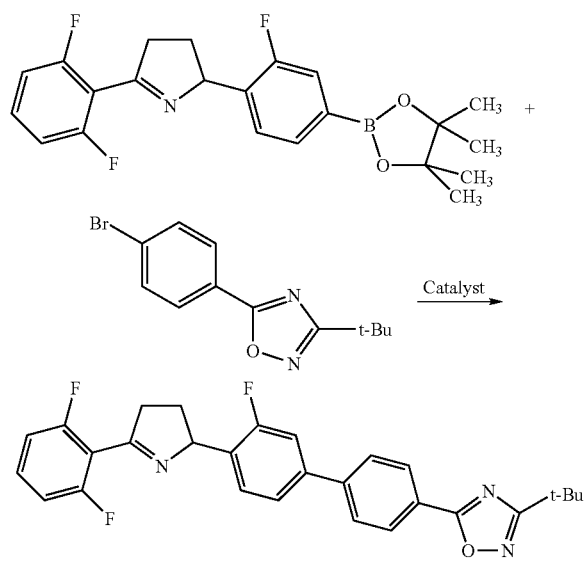

The formula (II) provides a general definition of the $\Delta^1$-pyrrolines required as starting materials for carrying out the process (A) according to the invention. In this formula, $R^1$, $R^2$, $R^3$, $R^4$, $A^1$ and $R^5$ preferably, particularly preferably, very particularly preferably and especially preferably have those meanings which have already been mentioned in connection with the description of the compounds of the formula (I) according to the invention as being preferred, particularly preferred, etc., for these radicals.

$\Delta^1$-Pyrrolines of the formula (II) are known and/or can be prepared by known processes (cf. WO 98/22438, for $R^4$=hydrogen see also WO 02/46151, for $R^4$=alkyl and optionally substituted aryl see also DE-A 102 05 862, for $R^4$=alkoxycarbonyl, (cycloalkyl)oxycarbonyl, (haloalkoxy) carbonyl see also WO 02/24646, see also the Preparation Examples).

The formula (IE) provides a general definition of the benzene derivatives required as starting materials for carrying out the process (A) according to the invention. In this formula, $A^2$, $R^6$, $R^7$, $R^8$ and Q preferably, particularly preferably, very particularly preferably and especially preferably have those meanings which have already been mentioned in connection with the description of the compounds of the formula (I) according to the invention as being preferred, particularly preferably, etc., for these radicals.

Some benzene derivatives of the formula (III) are known, and/or they can be prepared analogously to known compounds (cf. for Q1: Helv. Chim. Acta 1989, 72, 447-456, J. Heterocycl. Chem. 1998, 35, 1313-1316, Pharm. Chem. J. (Engl.), 1971, 5, 401, Chem. Heterocycl. Compd. (Engl.) 1984, 20, 1319-1321, JCS Chem. Commun. 1981, 21, 1106-1107, JCS Chem. Commun. 1992, 4, 348-349, J. Am. Chem. Soc. 1941, 63, 3189-3191, Bull. Chem. Soc. Jpn. 1998, 71, 475-482; for Q2: J. Chem. Soc. 1904, 85, 1483, J. Heterocycl. Chem. 2001, 38, 1197-1202, Chem. Pharm. Bull. 1985, 33, 937-943, Tetrahedron Lett. 1992, 3911-3914, Helv. Chim. Acta 1993, 76, 521-534, Tetrahedron Lett. 1994, 3609-3612, JCS Chem. Commun. 1982, 18, 1055-1056, J. Org. Chem. 1984, 49, 3819-3824, Synthesis 1999, 1, 61-63; for Q3: J. Org. Chem. 1970, 35, 1729, Egypt. J. Chem. 1999, 42, 491-498, J. Prakt. Chem. 1985, 327, 463-470, JCS Perkin Trans. 1 1987, 1457-1464, JCS Perkin Trans. 1 1992, 2203-2214, Phosphorus Sulfur 1977, 3, 377, J. Org. Chem. 2001, 66, 7283-7286, J. Am. Chem. Soc. 1954, 76, 4450-4452, Synth. Commun. 1995, 25, 2449-2456, Liebigs Ann. Chem. 1988, 465-470, J. Heterocycl. Chem. 1994, 31, 1005-1010; for Q4: Bull. Chem. Soc. Jpn. 1994, 67, 2187-2194, Liebigs Ann. Chem. 1992, 387-394, C. R. Hebd. Seances Acad. Sci. , 1953, 237, 397, Tetrahedron Lett. 1995, 1925-1928, Synthesis 1993, 10, 959-960, J. Prakt. Chem. 1983, 325, 457-462, Bioorg. Med. Chem. Lett. 1997, 7, 3101-3106, Tetrahedron Lett. 1989, 3093-3096, Bull. Soc. Chim. Fr. 1956, 1147-1150; for Q5: J. Heterocycl. Chem. 1993, 30, 617-622, JCS Chem. Commun. 1990, 20, 1393-1394, J. Heterocycl. Chem. 1992, 29, 1401-1403, J. Indian Chem. Soc. 1987, 64, 713-715, Acta Chem. Scand. 1998, 52, 399-406, JCS Perkin Trans. 1 1991, 3245-3251, Tetrahedron 1995, 51, 12373-12382, Chem. Heterocycl. Compd. (Engl.) 1991, 27, 918-920, Eur. J. Med. Chem. Chim. Ther. 1992, 27, 717-722; for Q6: J. Heterocycl. Chem. 1982, 19, 977-979, Tetrahedron 1990, 46, 3515-3526, Liebigs Ann. Chem. 1989, 1145-1146, J. Heterocycl. Chem. 1995, 32, 985-990, Farmaco Ed. Sci. 1988, 43, 677-692, J. Med. Chem. 1990, 33, 21-31, Heterocycles 1993, 36, 2541-2548, J. Org. Chem. 1984, 49, 62-74, Synth. Commun. 1986, 16, 357-364, Bioorg. Med. Chem. Lett. 1998, 8, 2689-2694; for Q7: Bull. Chem. Soc. Jpn. 1995, 68, 1, 341-349, Bull. Soc. Chim. Fr.

1980, 2, 11-12, 552-558, J. Indian Chem. Soc. 1987, 64, 713-715, J. Chem. Res. Miniprint 1995, 8, 1901-1912, Tetrahedron 2001, 57, 22, 4767-4774, J. Org. Chem. 1997, 62, 3, 715-720, Tetrahedron 1994, 50, 26, 7849-7856, J. Org. Chem. 1986, 51, 16, 3125-3133, JCS Perkin Trans. 1 1997, 1851-1854, J. Am. Chem. Soc. 1967, 89, 3077; for Q8: Justus Liebigs Ann. Chem. 1911,385, 100, J. Chem. Soc. C 1971, 2147-2150, J. Gen. Chem. USSR (Engl.), 1977, 47, 81-86, Biochem. J. 1936, 30, 407, J. Am. Chem. Soc. 1993, 115, 7645-7652, Chem. Ber. 1960, 93, 1208,1211, J. Gen. Chem. USSR (Engl.) 1961, 31, 1390, Chem. Ber. 1968, 101, 839, Arch. Pharm. Ber. Dtsch. Pharm. Ges. 1967, 300, 704-708, Tetrahedron 1999, 55, 14451-14458, Chem. Ber. 1978, 111, 780-790, J. Org. Chem. 1966, 31, 1538-1541, Farmaco Ed. Sci. 1971, 26, 276-286, J. Chem. Soc. 1963, 1332, 1333, Justus Liebigs Ann. Chem. 1904, 331, 206, Justus Liebigs Ann. Chem. 1902, 320, 26, Justus Liebigs Ann. Chem. 1904, 331, 224, Justus Liebigs Ann. Chem. 1904, 331, 234, Justus Liebigs Ann. Chem. 1908, 361, 270, Synth. Commun. 1996, 26, 4289-4297, C. R. Hebd. Seances Acad. Sci. Ser. C 1968, 266, 290-292, Bull. Soc. Chim. Belg. 1977, 86, 949-952, J. Heterocycl. Chem. 1974, 11, 135-137, J. Chem. Soc. C 1970, 445-448, Heterocycles 1993, 35, 909-914, J. Org. Chem. 1969, 34, 1474-1477, J. Am. Chem. Soc. 1941, 63, 1677, Helv. Chim. Acta, 1927, 10, 305, Heterocycles 1992, 33, 813-818, J. Org. Chem. 1962, 27, 4293-4300, J. Gen. Chem. USSR (Engl.) 1961, 31, 159, J. Am. Chem. Soc. 1961, 83, 2937, Can. J. Chem. 1963, 41, 2086-2092, Bull. Soc. Chim. Fr. 1975, 1371-1373; for Q9: J. Am. Chem. Soc. 1950, 72, 3843, 3844, Gazz. Chim. Ital. 1957, 87, 720, 724, Chem. Ber. 1960, 93, 1433-1446, Bull. Soc. Chim. Fr. 1966, 2832-2845, J. Org. Chem. 1961, 26, 4441-4455, J. Org. Chem. 1973, 38, 2949-2953, J. Org. Chem. 1973, 38, 2945-2948, Bull. Soc. Chim. Fr. 1966, 2381-2384, Tetrahedron Lett. 1973, 1199, Chem. Heterocycl. Compd. (Engl.) 1979, 15, 501-506, Tetrahedron Lett. 1988, 6001-6004, J. Org. Chem. 1965, 30, 1892-1895, J. Org. Chem. 1969, 34, 3639, Justus Liebigs Ann. Chem. 1968, 719, 145, J. Heterocycl. Chem. 1972, 9, 1219-1223, J. Heterocycl. Chem. 1988, 25, 1307-1310, Tetrahedron 1990, 46, 577-586, Heterocycles 1996, 43, 1597-1600, J. Prakt. Chem. 1986, 328, 321-326, C. R. Hebd. Seances Acad. Sci. Ser. C 1968, 266, 290-292, Chem. Ber. 1959, 92, 2593-2599, DE-A 2643640, J. Chem. Res. Synop. 1995, 5, 198-199, J. Heterocycl. Chem. 1994, 31, 1377-1380, Chem. Pharm. Bull. 1984, 32, 4402-4409, Bioorg. Med. Chem. Lett. 1997, 7, 2121-2124, J. Org. Chem. 1997, 62, 8325-8334, J. Heterocycl. Chem. 1993, 30, 365-371, Helv. Chim. Acta 1927, 10, 305, Heterocycles 1992, 33, 813-818, Arch. Pharm. Ber. Dtsch. Pharm. Ges. 1967, 300, 704-708, J. Org. Chem. 1962, 27, 4293-4300, J. Am. Chem. Soc. 1961, 83, 2937, Can. J. Chem. 1963, 41, 2086-2092, Bull. Soc. Chim. Fr. 1975, 1371-1373; for Q10: J. Prakt. Chem. 1935, 143, 259, 273, Angew. Chem. 1978, 90, 731-732, DE-A 1809386, J. Am. Chem. Soc. 1949, 71, 2671-2674, Bull. Soc. Chim. Fr. 1969, 1687, Tetrahedron Lett. 1998, 3287-3290, Syn. Lett. 1999, 3, 299-302, Justus Liebigs Ann. Chem. 1927, 458, 209, Chem. Ber. 1978, 111, 791-794, Bull. Soc. Chim. Jpn. 2000, 73, 1861-1864, DE-A 2524048, J. Med. Chem. 1997, 40, 1347-1365, J. Heterocycl. Chem. 1973, 10, 669-670, Bull. Soc. Chim. Belg. 1977, 86, 949-952, Acta Chem. Scand. 1970, 24, 3109-3115, J. Heterocycl. Chem. 1986, 23, 1363-1366, Justus Liebigs Ann. Chem. 1908, 358, 169, J. Heterocycl. Chem. 1990, 27, 487-495, Chem. Lett. 1988, 5, 819-822, Chem. Pharm. Bull. 1984, 32, 4402-4409, J. Org. Chem. 1961, 26, 948, Can. J. Chem. 1979, 57, 1186-1200; for Q11: Justus Liebigs Ann. Chem. 1932, 492, 283-291; for Q12: J. Chem. Soc. 1947, 96-100, J. Am. Chem. Soc. 1993, 115, 7645-7652, Tetrahedron Lett. 1999, 2657-2660, Bull. Soc. Chim. Fr. 1986, 1, 129-132, Chem. Heterocycl. Compd. (Engl.) 1979, 15, 544-548, Tetrahedron 1996, 52, 7939-7946, Monatsh. Chem. 1996, 127, 313-318, Tetrahedron Lett. 1989, 4435-4438, Synthesis 1987, 12, 1136-1138, Can. J. Chem. 1979, 57, 813-821, U.S. Pat. No. 3,644,392, J. Med. Chem. 1985, 28, 1405-1413, JCS Perkin Trans. 1 1994, 239-244, J. fluorineine Chem. 1995, 74, 279-282, J. Med. Chem. 1989, 32, 575-583, J. Org. Chem. 1977, 42, 1153-1159, J. Prakt. Chem. 1991, 333, 355-360, J. Indian Chem. Soc. 1981, 58, 624-625, Tetrahedron 2001, 57, 3413-3418, Chem. Pharm. Bull. 1982, 30, 1722-1730; for Q13: J. Chem. Soc. 1948, 1969, J. Heterocycl. Chem. 1983, 20, 1277-1281, Chem. Lett. 1983, 341-342, Arch. Pharm. (Weinheim Ger.) 1976, 309, 391-394, DE-A 2533211, Arch. Pharm. (Weinheim Ger.) 1974, 307, 972-975, J. Chem. Soc. 1957, 4225-4227, Chem. Pharm. Bull. 1988, 36, 1669-1675, Synthesis 1995, 4, 449-452, J. Org. Chem. 1997, 62, 3480-3487, J. Heterocycl. Chem; 1977, 14, 889-891, U.S. Pat. No. 4,110,456, J. Med. Chem. 1975, 18, 895-896, DE-A 2061489, DE-A 2061515, U.S. Pat. No. 4,125,530, Chem. Pharm. Bull. 1986, 34, 3111-3120, Tetrahedron 1997, 53, 7237-7254, Bull. Chem. Soc. Jpn. 1998, 71, 467-474, J. Org. Chem. 2002, 67, 2699-2701, J. Med. Chem. 1999, 42, 3572-3587, Pharmazie 1992, 47, 623-626; for Q14: J. Pharm. Pharmacol. 1964, 16, 400-402, GB 1046248, Synthesis 2001, 14, 2075-2077, J. Org. Chem. 2000, 65, 1516-1524, CH 566996, JCS Perkin Trans. 1 1985, 2333-2336, J. Med. Chem. 1977, 20, 563-566, Bull. Chem. Soc. Jpn. 1978, 51, 1846-1855, J. Heterocycl. Chem. 1990, 27, 487-495, J. Org. Chem. 1988, 53, 129-135, J. Org. Chem. 1982, 47, 2867-2872, Chem. Ber. 1959, 92, 550-560, Chem. Ber. 1959, 92, 329-335, Angew. Chem. 1959, 71, 753-769, Tetrahedron 1997, 53, 11355-11368; for Q15: J. Heterocycl. Chem. 1983, 20, 1277-1281, Monatsh. Chem. 1968, 99, 2059-2071, Tetrahedron Lett. 1971, 2205, J. Org. Chem. 1978, 43, 2289, Justus Liebigs Ann. Chem. 1954, 585, 68, 79, Angew. Chem. 1959, 71, 753-757, Chem. Ber. 1962, 95, 2049-2053, Chem. Ber. 1960, 93, 723-736, Bull. Soc. Chim. Belg. 1976, 85, 573-575, J. Prakt. Chem. 1991, 333, 355-360, Justus Liebigs Ann. Chem. 1971, 744, 51-64, Tetrahedron Lett. 1968, 1809, J. Med. Chem. 1985, 28, 1188-1194, J. Heterocycl. Chem. 1990, 27, 487-495, Bioorg. Med. Chem. Lett. 1999, 9, 1023-1028, Justus Liebigs Ann. Chem. 1975, 160-194, Chem. Ber. 1959, 92, 329-335, Heterocycles 1993, 35, 433-440, Biosci. Biotechnol. Biochem. 1992, 56, 161-162, J. Med. Chem. 1996, 39, 596-604, Heterocycles 1997, 44, 67-70, Bull. Chem. Soc. Jpn. 1998, 71, 467-474, Recl. Trav. Chim. Pays-Bas 1979, 98, 258-262, J. Org. Chem. 1977, 42, 1153-1159; for Q16, Q17 and Q18: Helv. Chim. Acta 1977, 60, 284-297, JCS Perkin Trans. 1 1994, 147-152, J. Org. Chem. USSR (Engl.) 1978, 14, 1697-1701, Tetrahedron 1969, 25, 771-782, J. Org. Chem. 1966,31, 3612-3615, Tetrahedron Lett. 1992, 7769-7770, Org. Prep. Proced. Int. 1992, 24, 127-134, Synthesis 1998, 9, 1298-1304; for Q19 and Q20: Chem. Heterocycl. Compd. (Engl.) 1973, 9, 1199-1201, J. Chem. Soc. C 1971, 2644-2647, Gazz. Chim. Ital. 1938, 68, 625, 635, Gazz. Chim. Ital. 1961, 91, 1005-1022, JCS Perkin Trans. 1 1977, 2154-2157, Chem. Abstr. 1959, 53, 5185, Gazz. Chim. Ital. 1968, 98, 331-343, JCS Perkin Trans. 1 1975, 2115-2117, Gazz. Chim. Ital. 1959, 89, 1784-1793, Tetrahedron 1961, 12, 41-50, Can. J. Chem. 1970, 48, 1371-1376, Tetrahedron Lett. 1989, 3987-3990, J. Am. Chem. Soc. 1945, 67, 132, J. Am. Chem. Soc. 1931, 53, 1133-1136; for Q21: Acta Chem. Scand. 1992, 46, 372-383, J. Org. Chem. USSR (Engl.) 1985, 21, 191-196, J. Gen. Chem. USSR (Engl.) 1963, 33, 3590-3592, Tetrahedron 1997, 53, 9657-9668, Tetrahedron Lett. 1978, 5003-5006, Chem. Heterocycl. Compd. (Engl.) 1970, 6, 322-323, J. Med. Chem. 1991, 34, 2158-2165, Eur. J. Org. Chem. 1999, 11, 3117-3126, J. Heterocycl. Chem. 1994, 31, 1545-1552, Synthesis 1984, 3, 250-252, J. Am. Chem. Soc. 1949, 71, 367, J. Med. Chem. 1974, 17, 1177-1181; for Q22: J. Indian Chem. Soc. 1975, 52, 766-767, Heterocycles 1990, 31, 1115-1127, Justus Liebigs Ann. Chem. 1976, 395-399, Tetrahedron Lett. 1981, 3305-3308, J. Am. Chem. Soc. 1934, 56, 970, Bioorg. Med. Chem. Lett. 1999, 9, 1167-1170, JCS Perkin Trans. 1 1981, 2340-2343, Chem. Ber. 1956, 89, 107-113, Helv. Chim. Acta 1978, 61, 3143-3148, J. Chem. Soc. 1947, 1656-1658, Bull. Soc. Chim. Fr. 1963, 2498-2503, Helv. Chim. Acta 1950, 33, 1353, 1360, Gazz. Chim. Ital. 1975, 105, 1265-1271, Collect. Czech. Chem. Commun. 1993, 58, 1898-1904; for Q23: C. R. Hebd. Seances Acad. Sci. Ser. C 1967, 264, 336-339, J. Chem. Soc. 1952, 4099-4102, J. Indian Chem. Soc. 1970, 47, 323-330, Bull. Soc. Chim. Fr. 1967, 4523-4533, JCS Perkin Trans. 1 1993, 351-356, Helv. Chim. Acta 1978, 61, 3143-3148, Bull. Soc. Chim. Fr. 1967, 4523-4533, Bull. Soc. Chim. Fr. 1966, 2857-2861; for Q24 and Q25: Heterocycles 1994, 37, 859-868, J. Heterocycl. Chem. 1987, 24, 243-245, Chem. Pharm. Bull. 1968, 16, 148-159, J. Heterocycl. Chem. 1970, 7, 871-873, Tetrahedron 1969, 25, 389-395, J. Amer. Chem. Soc. 1985, 107, 2721-2730, Aust. J. Chem. 1989, 42, 1291-1306, Synthesis 1987, 4, 349-353, Chem. Lett. 1984, 1691-1692; for Q26: J. Heterocycl. Chem. 1973, 10, 611-622, Monatsh. Chem. 1926, 47, 798, Gazz. Chim. Ital. 1923, 53, 641, Gazz. Chim. Ital. 1924, 54, 213, Monatsh. Chem. 1927, 48, 396, J. Prakt. Chem. 1903, 67, 492, J. Heterocycl. Chem. 1983, 20, 1693-1695, Eur. J. Med. Chem. Chim. Ther. 1990, 25, 95-101, J. Heterocycl. Chem. 1983, 20, 1533-1537, Russ. J. Org. Chem. 2001, 37, 1621-1628; for Q27: Indian J. Chem. 1971, 9, 642-646, J. Indian Chem. Soc. 1974, 51, 613, Farmacia (Bucharest), 1971, 19, 199, 202, J. Heterocycl. Chem. 1984, 21, 1225-1229, J. Indian Chem. Soc. 1984, 61, 530-533, Indian J. Chem. Sect. B20 1981, 11, 1017-1018, Diss. Pharm. Pharmacol. 1970, 22, 217, Chem. Heterocycl. Compd. (Engl.) 1968, 4, 275, Indian J. Chem. 1973, 11, 321-324; for Q28: Heterocycles 1993, 36, 455-472, Arch. Pharm. (Weinheim Ger.) 1990, 323, 225-227, Arch. Pharm. (Weinheim Ger.) 1990, 323, 221-223, Eur. J. Med. Chem. Chim. Ther. 1990, 25, 95-101, Monatsh. Chem. 1988, 119, 349-354, DE-A 2265212, Heterocycles 1992, 34, 315-320, J. Heterocycl. Chem. 1983, 20, 1693-1695, Synthesis 1983, 6, 483-486, Chem. Ber. 1979, 112, 1635-1649, Molecules 2001, 6, 969-978, Chem. Pharm. Bull. 1975, 23, 955, 959, Bioorg. Med. Chem. Lett. 2001, 11, 3165-3168; for Q29: J. Org. Chem. USSR (Engl.) 1988, 24, 1794-1800, Justus Liebigs Ann. Chem. 1951, 574, 85-97, J. Med. Chem. 1994, 37, 125-132, DE-A 2265212, Synthesis 1983, 6, 483-486; for Q30: Eur. J. Med. Chem. Chim. Ther. 1985, 20, 257-266, J. Med. Chem. 1994, 37, 125-132, J. Med. Chem. 1971, 14, 260-262, J. Indian Chem. Soc. 1984, 61, 530-533, J. Heterocycl. Chem. 1984, 21, 1225-1229; for Q31: J. Chem. Soc. 1954, 4251, J. Heterocycl. Chem. 1983, 20, 1609-1612, Collect. Czech. Chem. Commun. 1985, 50, 2722-2729, DE-A 2426878, DE-A 2050346; for Q32: J. Phys. Chem. B105 2001, 37, 8845-8860, Chem. Heterocycl. Compd. (Engl.) 1997, 33, 712-717, Bull. Soc. Chim. Fr., 1966, 153-159, Agric. Biol. Chem. 1973, 37, 1465-1466, Justus Liebigs Ann. Chem. 1965, 686, 145-153; for Q33: Gazz. Chim. Ital. 1932, 62, 432-434, Indian J. Chem. Sect. B27 1988, 1-12, 793-796; for Q34: Ann. Chim. (Rome) 1957, 47, 376-384, J. Org. Chem. 1979, 44, 4160-4164, Chem. Pharm. Bull. 1992, 40, 2399-2409, Justus Liebigs Ann. Chem. 1968, 716, 156-159; for Q35: DE-A 2050346, DE-A 2242187, J. Org. Chem. 1974, 39, 962-964; for Q36: CH 426848, GB 899842, Chem. Pharm. Bull. 1991, 39, 2837-2841, Tetrahedron 1976, 32, 1031-1035; for Q37: Heterocycles 1996, 43, 2435-2442, J. Organomet. Chem. 1979, 166, 25-30, J. Heterocycl. Chem. 1980, 17, 1681-1685; for Q38: J. Org. Chem. 1974, 39, 962-964, J. Org. Chem. 1980, 45, 3750-3753, J. Chem. Soc. 1960, 3234-3239).

The process (A) according to the invention is preferably carried out using a palladium catalyst which in turn can be used with or without addition of further ligands. The catalyst used is preferably $PdCl_2(dppf)$ [dppf=1,1'-bis(diphenylphosphino)ferrocene], $Pd(PPh_3)_4$, $PdC_2(PPh_3)_2$, $PdCl_2(CH_3CN)_2$, $Pd_2(dba)_3$ [dba=dibenzylideneacetone] or $Pd(OAc)_2$, particularly preferably $Pd(OAc)_2$.

Suitable ligands are triarylphosphines, trialkylphosphines or arsines. Preference is given to using dppf, $PPh_3$, P(tert-Bu)$_3$, $Pcy_3$ or $AsPh_3$, particularly preferably dppf.

Suitable diluents for carrying out the process (A) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholan. Particular preference is given to using acetone, dimethoxyethane, dioxane, tetrahydrofuran, dimethylformamide, dimethylacetamide, dimethyl sulphoxide, ethanol, toluene or, if appropriate, mixtures of these diluents with water.

Suitable bases for carrying out the process (A) according to the invention are all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, alkali metal fluorides, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to carry out the reaction without added acid binder, or to employ an excess of amine component so that it simultaneously acts as acid binder. Particular preference is given to using barium hydroxide, sodium hydroxide, potassium hydroxide, tripotassium phosphate, caesium carbonate, potassium carbonate, sodium carbonate, potassium acetate, triethylamine, potassium tert-butoxide, caesium fluoride or potassium fluoride.

When carrying out the process (A) according to the invention, the reaction temperatures can be varied within a relatively wide range. In general, the process is carried out at temperatures between 0° C. and 140° C., preferably between 20° C. and 120° C., particularly preferably between 60° C. and 100° C.

When carrying out the process (A) according to the invention, in general 1 mol or else a slight excess of a compound of the formula (III) and 0.1 to 50 mol % of a catalyst are employed per mole of compound of the formula (II). However, it is also possible to use the reaction components in other ratios. Work-up is carried out by customary methods. In general, the reaction mixture is diluted with water and extracted with an organic diluent. The organic phase is washed, dried, filtered and concentrated. The residue is, if appropriate, freed of any impurities that may still be present using customary methods, such as chromatography or recrystallization.

All processes according to the invention are generally carried out under atmospheric pressure. However, in each case it is also possible to operate under elevated or reduced pressure.

The active compounds are suitable for protecting plants and plant organs, for increasing the harvest yields, for improving the quality of the harvested material and for controlling animal pests, in particular insects, arachnids and nematodes, which are encountered in agriculture, in forests, in gardens and leisure facilities, in the protection of stored products and of materials, and in the hygiene sector, and have good plant tolerance and favourable toxicity to warm-blooded animals and are tolerated well by the environment. They may be preferably employed as plant protection agents. They are active against normally sensitive and resistance species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomnma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hernitarsonemus* spp., *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The compounds of the formula (I) according to the invention have in particular excellent activity against caterpillars, beetle larvae, spider mites, aphids and leaf-mining flies.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As Solid Carriers there are Suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable mixing components are, for example, the following compounds:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromucon-azole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin;

kresoxim-methyl; mancozeb; maneb; meferimzone; mepanipyrim; mepronil; metalaxyl; metalaxyl-M; met-conazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tri-cyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulphonyl)amino]butanemide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofenprox, bromophosethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, ciscypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1 R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimnine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permnethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphosethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, suiprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*,

WL-108477, WL40027,

YI-5201, YI-5301, YI-5302,

XMC, xylylcarb,

ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, fertilizers, growth regulators, safeners and/or semiochemicals is also possible.

When used as insecticides, the active cormpounds according to the invention can furthermore be present in their commercially available formulations and in the use forms, prepared from these formulations, as a mixture with synergistic agents. Synergistic agents are compounds, which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the vicinity of the plant, on the surface of parts of plants or in plant tissues.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and worms by toxins formed in the plants, in particular those formed in the plants by the genetic material from Bacillus thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexius, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against the development stages of ticks, such as, for example, *Amblyomma hebraeum,* and against parasitic flies, such as, for example, *Lucilia cuprina* and against fleas, such as, for example, *Ctenocephalides felis.*

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without a limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutes;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypennethrin, deltamethrin, permethrin, imidacloprid, NI-25, flufenoxuron, hexaflumuron, transfluthrin, thiacloprid, methoxyfenozide, triflumuron, clothianidin, spinosad, tefluthrin, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operational costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn; fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole; molluscicides such as fentin acetate, metaldehyde, methiocarb, niclosamid, thiodicarb and trimethacarb; or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)pyridine, 2,4,5,6-tetrachloroisophthalonitrile, tetramethylthiuram disulphide and 2,4,6-trichlorophenylmaleiimide.

The antifouling compositions used comprise the active compound according to the invention of the compositions according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders. Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller driven evaporators, energy-free, or passive, evaporation systems, moth papers, moth bags and moth gels, as granules or dusts, in baits for spreading or in bait stations.

The preparation and use of the substances according to the invention are illustrated by the examples below.

PREPARATION EXAMPLES

Example 1

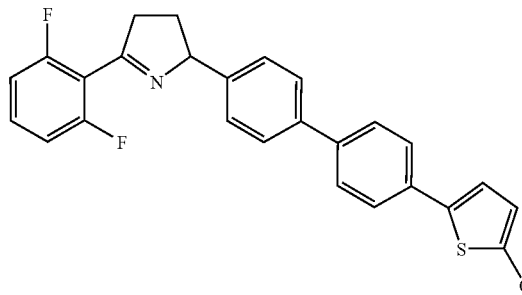

Under argon, 0.7 g (2.47 mmol) of 2-(4-bromophenyl)-5-ethoxythiophene and 0.95 g (2.47 mmol) of 5-(2,6-difluorophenyl)-2-[4-(4,4,5,5-tetramethyl-1,3,2-dioxaborolan-2-yl)phenyl]-3,4-dihydro-2H-pyrrole are initially charged in 30 ml of absolute tetrahydrofuran. After addition of 2.63 g (9.89 mmol) of tripotassium phosphate trihydrate, 11 mg (0.05 mmol) of palladium(II) acetate and 37 mg (0.124 mmol) of 2-(di-tert-butylphosphino)biphenyl, the mixture is heated under reflux for 5 h, identical amounts of palladium (II) acetate and 2-(di-tert-butylphosphino)biphenyl are added and this mixture is then heated under reflux for another 10 h. After cooling, the reaction mixture is poured into water and the product is extracted with dichloromethane. The organic phase is dried and concentrated under reduced pressure. This gives 1.05 g of a resin-like crude product which is chromatographed on silica gel using the system cyclohexane/ethyl acetate (2:1).

This gives 0.22 g (19.4% of theory) of 5-(2,6-difluorophenyl)-2-[4'-(5-ethoxy-2-thienyl)-1,1'-biphenyl-4-yl]-3,4-dihydro-2H-pyrrole as light-yellow crystals of melting point 128° C.-134° C., of log P (pH 2.3)=4.88 and log P (pH 7.5)=5.84.

Example 2

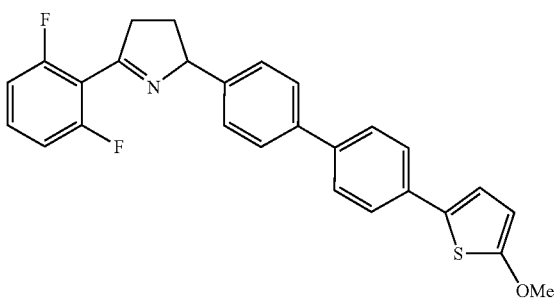

Analogously to Example 1, starting from 2-(4-bromophenyl)-5-methoxythiophene, 5-(2,6-difluorophenyl)-2-[4'-(5-methoxy-2-thienyl)-1,1'-biphenyl-4-yl]-3,4-dihydro-2H-pyrrole of melting point 138° C.-142° C. and log P (pH 2.3)=4.35 is obtained.

Example 3

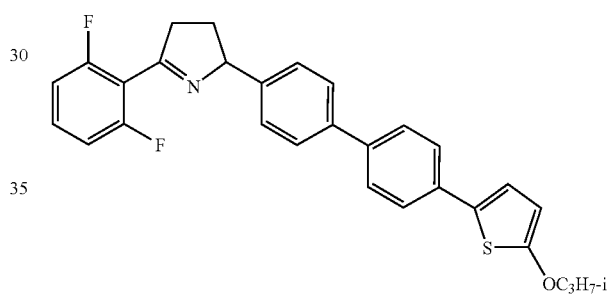

Analogously to Example 1, starting from 2-(4-bromophenyl)-5-isopropoxythiophene, 5-(2,6-difluorophenyl)-2-[4'-(5-isopropoxy-2-thienyl)-1,1'-biphenyl-4-yl]-3,4-dihydro-2H-pyrrole of melting point 131° C.-134° C. and log P (pH 2.3)=5.20 is obtained.

Example 4

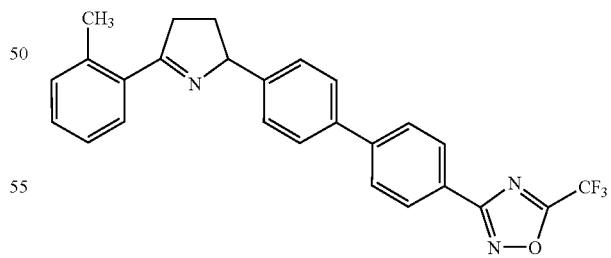

Under an atmosphere of argon, 3-(4-bromophenyl)-5-trifluoromethyl-1,2,4-oxadiazole (0.29 g, 1.0 mmol), 5-(2-methylphenyl)-2-[4-(4,4,5,5-tetramethyl-1,3,2-dioxaborolan-2-yl)phenyl]-3,4-dihydro-2H-pyrrole (II-1) (0.3 g, 0.83 mmol), dissolved in 12 ml of dimethoxyethane, 1,1'-bis (diphenylphosphino)ferrocenepalladium(II) chloride (0.018 g, 0.025 mmol) and sodium carbonate solution (1.25 ml, 2 M) are added successively to a reaction vessel which is then closed. The reaction mixture is stirred at 80° C. for 16 h.

After the reaction has ended, the mixture is cooled to room temperature. 1 g of Isolute RHM-N (Separtis) is added and the mixture is concentrated. The residue is purified by cartridge chromatography (gradient cyclohexane/ethyl acetate 95:5→3:2).

This gives 0.085 g (19.2% of theory) of 3-{4'-[5-(2-methylphenyl)-3,4-dihydro-2H-pyrrol-2-yl]-1,1'-biphenyl-4-yl}-5-(trifluoromethyl)-1,2,4-oxadiazole of log P (pH 2.3) =3.32.

Example 5

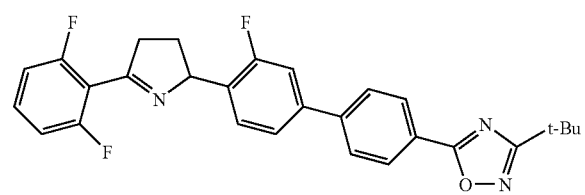

5-(4-Bromophenyl)-3-tert-butyl-1,2,4-oxadiazole (0.31 g, 1.1 mmol), 1,1'-bis(diphenylphosphino)ferrocenepalladium (II) chloride (0.022 g, 0.03 mmol) and 1.5 ml of an aqueous 2 M sodium carbonate solution are added successively to a solution of 5-(2,6-difluorophenyl)-2-[2-fluoro-4-(4,4,5,5-tetramethyl-1,3,2-dioxaborolan-2-yl)phenyl]-3,4-dihydro-2H-pyrrole (II-2) (0.40 g, 1 mmol) in 30 ml of dimethoxyethane. This mixture is allowed to react at 80° C. for 16 h. For work-up, the reaction mixture is allowed to cool, and water/ethyl acetate are added. The organic phase is separated off, dried over sodium sulphate, filtered and concentrated. The crude product is purified by silica gel column chromatography (gradient methylene chloride/ethyl acetate 100:0→95:5).

This gives 0.3 g (60.3% of theory) of 3-tert-butyl-5-{4'-[5-(2,6-difluorophenyl)-3,4-dihydro-2H-pyrrol-2-yl]-3'-fluoro-1,1'-biphenyl-4-yl}-1,2,4-oxadiazole of log P (pH 2.3)=5.79 and log P (pH 7.5)=6.06.

Example 6

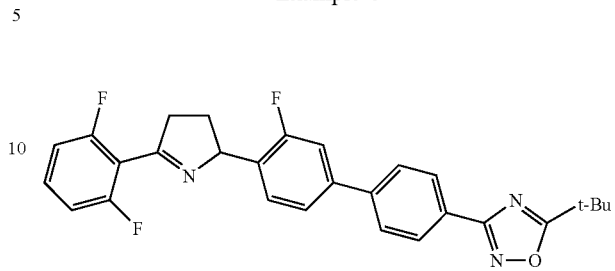

3-(4-Bromophenyl)-5-tert-butyl-1,2,4-oxadiazole (0.46 g, 1.65 mmol), 1,1'-bis(diphenylphosphino)ferrocenepalladium(II) chloride (0.033 g, 0.045 mmol) and 2.25 ml of an aqueous 2 M sodium carbonate solution are added successively to a solution of 5-(2,6-difluorophenyl)-2-[2-fluoro-4-(4,4,5,5-tetramethyl-1,3,2-dioxaborolan-2-yl)phenyl]-3,4-dihydro-2H-pyrrole (II-2) (0.60 g, 1.5 mmol) in 30 ml of dimethoxyethane. This mixture is allowed to react at 80° C. for 16 h. For work-up, the reaction mixture is allowed to cool, and water/ethyl acetate are added. The organic phase is separated off, dried over sodium sulphate, filtered and concentrated. The crude product is purified by silica gel column chromatography (gradient methylene chloride/ethyl acetate 100:0→95:5).

This gives 0.51 g (69.9% of theory) of 5-tert-butyl-3-{4'-[5-(2,6-difluorophenyl)-3,4-dihydro-2H-pyrrol-2-yl]-3'-fluoro-1,1'-biphenyl-4-yl}-1,2,4-oxadiazole of log P (pH 2.3)=5.65 and log P (pH 7.5)=5.97.

The following compounds of the formula (I-f) are obtained analogously to Examples 1 to 6, given above, and the general description.

TABLE 1

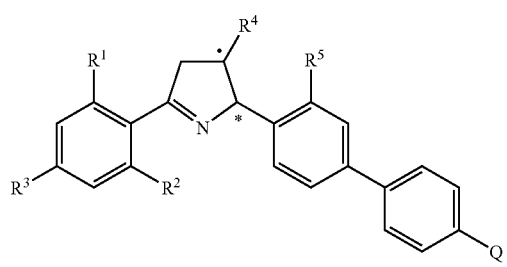

(I-f)

| No. | R¹ | R² | R³ | R⁴ | R⁵ | Q | *, • | logP | m.p./° C. |
|---|---|---|---|---|---|---|---|---|---|
| 7 | F | F | H | H | F | ![oxadiazole-CF3] | | 5.43[a)]<br>5.72[b)] | |
| 8 | F | F | H | CO₂Et | H | ![oxadiazole-CF3] | cis, racemate | 5.18[a)] | |

TABLE 1-continued (I-f)

| No. | R¹ | R² | R³ | R⁴ | R⁵ | Q | *, • | logP | m.p./° C. |
|---|---|---|---|---|---|---|---|---|---|
| 9 | F | F | H | CO₂Et | H | (3-methyl-5-t-Bu-1,2,4-oxadiazol-yl) | cis, racemate | 5.29[a] | |
| 10 | F | F | H | CO₂Et | H | (5-methyl-3-t-Bu-1,2,4-oxadiazol-yl) | cis, racemate | 5.39[a] | |
| 11 | CH₃ | H | H | H | H | (3-methyl-5-t-Bu-1,2,4-oxadiazol-yl) | | 3.99[a] | |
| 12 | CH₃ | H | H | H | H | (5-methyl-3-t-Bu-1,2,4-oxadiazol-yl) | | 4.18[a] | |
| 13 | F | F | H | C₂H₅ | H | (5-methyl-2-OC₃H₇-i-thienyl) | | 6.00[a]<br>6.80[b] | |
| 14 | CH₃ | H | H | H | F | (3-methyl-5-CF₃-1,2,4-oxadiazol-yl) | | 5.08[a] | |
| 15 | CH₃ | H | H | H | F | (3-methyl-5-t-Bu-1,2,4-oxadiazol-yl) | | 5.25[a] | |
| 16 | CH₃ | H | H | H | F | (5-methyl-3-t-Bu-1,2,4-oxadiazol-yl) | | 5.48[a] | |
| 17 | CH₃ | H | H | H | F | (5-methyl-2-OMe-thienyl) | | 4.82[a] | |
| 18 | F | F | H | H | H | (1-methyl-4-CN-pyrazolyl) | | 3.02[a]<br>4.03[b] | |
| 19 | F | F | H | H | H | (2-methyl-5-C(CH₃)₃-oxazolyl) | | 4.56[a]<br>5.62[b] | |

TABLE 1-continued (I-f)

| No. | R¹ | R² | R³ | R⁴ | R⁵ | Q | *, • | logP | m.p./° C. |
|---|---|---|---|---|---|---|---|---|---|
| 20 | F | F | H | H | H | 2-methyl-5-methoxy-thiazole | | 3.58[a)]<br>4.86[b)] | |
| 21 | F | F | H | H | H | 5-methyl-2-tert-butyl-oxazole | | 4.20[a)]<br>5.36[b)] | 52 |
| 22 | F | F | H | H | H | 2,4-dimethyl-thiazole | | 3.35[a)]<br>4.68[b)] | 151 |
| 23 | F | F | H | H | H | 2-methyl-4-tert-butyl-oxazole | | 5.04[a)]<br>6.09[b)] | 107 |
| 24 | F | F | H | H | H | 4-methyl-2-tert-butyl-thiazole | | 5.52[a)]<br>6.52[b)] | 112 |
| 25 | F | F | H | H | H | 4-methyl-2-isopropyl-thiazole | | 4.71[a)]<br>5.87[b)] | 118 |
| 26 | F | F | H | H | H | 4-methyl-2-(4-chlorobenzyl)-thiazole | | 5.21[a)]<br>6.11[b)] | 172 |
| 27 | F | F | H | H | H | 4-methyl-2-n-butyl-thiazole | | 5.16[a)] | 83–84 |
| 28 | F | F | H | H | H | 4-methyl-2-methoxy-thiazole | | | |
| 29 | F | F | H | H | H | 4-methyl-2-isopropoxy-thiazole | | | |

TABLE 1-continued

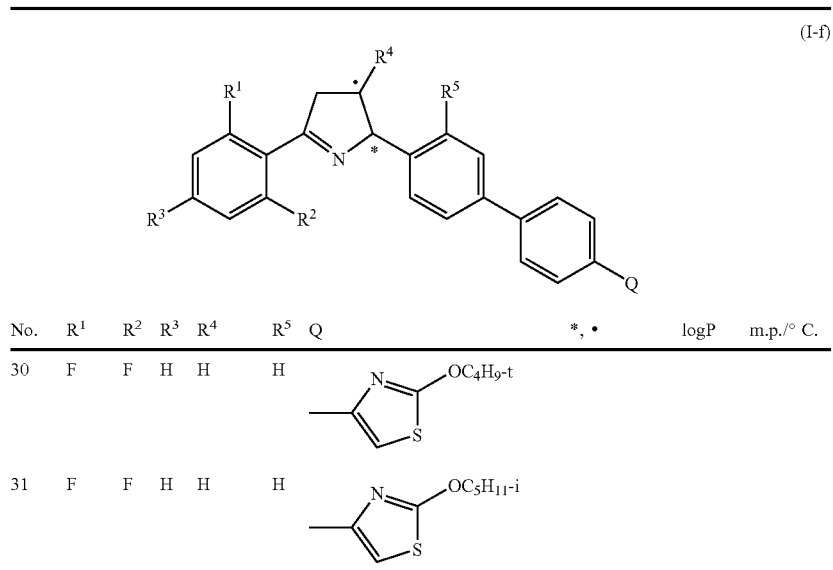

(I-f)

| No. | R¹ | R² | R³ | R⁴ | R⁵ | Q | *, • | logP | m.p./° C. |
|---|---|---|---|---|---|---|---|---|---|
| 30 | F | F | H | H | H | ![thiazole]  N-thiazole-OC₄H₉-t | | | |
| 31 | F | F | H | H | H | ![thiazole] N-thiazole-OC₅H₁₁-i | | | |

Preparation of Starting Materials of the Formula (II)

Example (II-1)

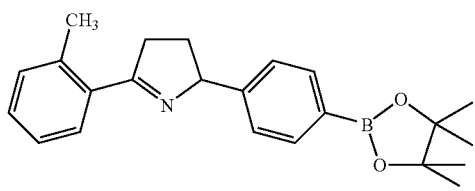

Step 1

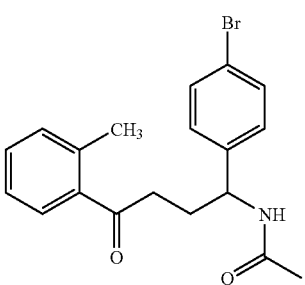

At 0° C., 150 ml of acetonitrile are added dropwise over a period of 45 min to 62.2 g (0.61 mol) of sulphuric acid, and the mixture is stirred for another 30 min. At about −5° C., a solution of [2-(4-bromophenyl)cyclopropyl](2-methylphenyl)methanone (48 g, 0.15 mol) in 300 ml of acetonitrile is then added dropwise over a period of 45 min, and the mixture is stirred for 16 h whilst warming to room temperature. The reaction mixture is stirred into ammonia (150 ml)/ice water (800 ml) and extracted three times with in each case 400 ml of ethyl acetate. The organic phase is separated off, dried over sodium sulphate, filtered and concentrated. The crude product is purified by flash chromatography (gradient methylene chloride/ethyl acetate 10:0→1:1).

This gives 17.2 g (33.3% of theory) of N-[1-(4-bromophenyl)-4-(2-methylphenyl)-4-oxobutyl]acetamide of log P (pH 2.3)=3.33.

Step 2

24 g (235 mmol) of sulphuric acid are added dropwise to a solution of N-[1-(4-bromophenyl)-4-(2-methylphenyl)-4-oxobutyl]acetamide (17.6 g, 47.0 mmol) in 100 ml of ethanol. The reaction mixture is then stirred under reflux. After cooling to room temperature, the reaction mixture is stirred into aqueous sodium hydroxide solution (45% strength, 100 ml)/ice water (500 ml) and extracted three times with in each case 400 ml of ethyl acetate. The organic phase is separated off, dried over sodium sulphate, filtered and concentrated. The crude product is purified by silica gel flash chromatography (methylene chloride/ethyl acetate 10:1).

This gives 10.6 g (68.7% of theory) of 2-(4-bromophenyl)-5-(2-methylphenyl)-3,4-dihydro-2H-pyrrole of log P (pH 2.3)=1.82 and log P (pH 7.5)=4.48.

Step 3

40 ml of dioxane are added to a mixture of 2-(4-bromophenyl)-5-(2-methylphenyl)-3,4-dihydro-2H-pyrrole (3.14 g, 10 mmol), 4,4,4',4',5,5,5',5'-octamethyl-2,2'-bis-1,3,2-dioxaborolane (2.79 g, 11 mmol), potassium acetate (2.94 g, 30 mmol), 1,1'-bis(diphenylphosphino)ferrocenepalladium(II) chloride (0.22 g, 0.3 mmol) and 1,1'-bis(diphenylphosphino)ferrocene (0.17 g, 0.3 mmol), and the mixture is allowed to react at 100° C. for 16 h. For work-up, 100 ml of water are added to the reaction mixture, which is then extracted twice with in each case 100 ml of ethyl acetate. The organic phase is separated off, dried over sodium sulphate, filtered and concentrated. The residue is dissolved in 30 ml of dichloromethane and purified by silica gel flash chromatography (gradient methylene chloride/ethyl acetate 10:0→9:1).

This gives 2.3 g (62.4% of theory) of 5-(2-methylphenyl)-2-[4-(4,4,5,5-tetramethyl-1,3,2-dioxaborolan-2-yl)phenyl]-3,4-dihydro-2H-pyrrole of log P (pH 2.3)=2.25 and log P (pH 7.5)=4.98.

Example (II-2)

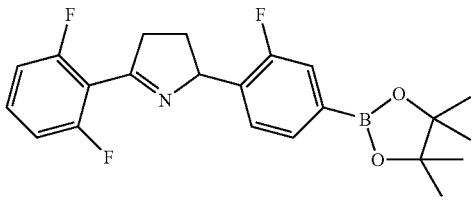

Step 1

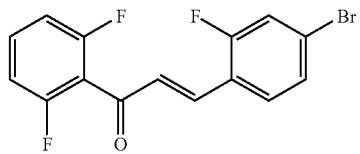

2-Fluoro-4-bromobenzaldehyde (20.3 g, 100 mmol) and 2,6-difluoroacetophenone (15.6 g, 100 mmol) are dissolved in methanol/water. With stirring, 30 ml of a 10% strength aqueous sodium hydroxide solution are slowly added dropwise. The solid that precipitates is filtered off with suction, washed with methanol/water and dried.

This gives 30.5 g (95.6% of theory) of (2E)-3-(4-bromo-2-fluorophenyl)-1-(2,6-difluoro-phenyl)-2-propen-1-one of log P (pH 2.3)=4.18.

Step 2

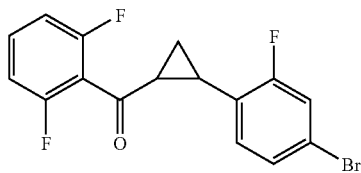

Under argon, potassium carbonate (13.8 g, 100 mmol) is initially charged in dimethyl sulphoxide. Trimethylsulphoxonium iodide (23.5 g, 250 mmol) is added a little at a time, and the mixture is then allowed to react at room temperature for 1.5 h. A solution of (2E)-3-(4-bromo-2-fluorophenyl)-1-(2,6-difluorophenyl)-2-propen-1-one (34 g, 100 mmol) in dimethyl sulphoxide is then added dropwise, and the mixture is stirred for 16 h. The reaction mixture is poured into about 500 ml of ice water and extracted with ethyl acetate/methyl tert-butyl ether. The organic phase is separated off, dried over sodium sulphate, filtered and concentrated. The residue is made into a paste using a little isopropanol and filtered off with suction, and the solid is dried.

This gives 31 g (84.1% of theory) of [2-(4-bromo-2-fluorophenyl)cyclopropyl](2,6-difluorophenyl)methanone of log P (pH 2.3)=4.31.

Step 3

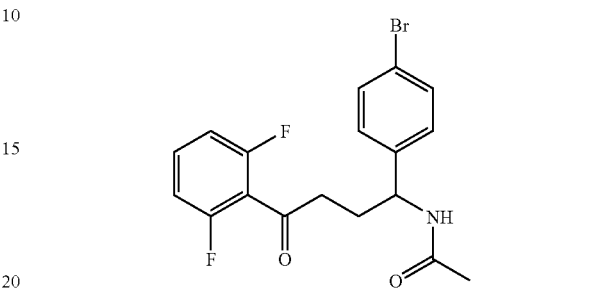

At 0° C., 100 ml of acetonitrile are added dropwise to 39 g of sulphuric acid, and the mixture is stirred for 1 h. The mixture is then cooled to −10° C., a solution of [2-(4-bromo-2-fluorophenyl)cyclopropyl](2,6-difluorophenyl)methanone (31 g, 87.3 mmol) in 380 ml of acetonitrile is added dropwise and the mixture is stirred at room temperature for 16 h. The reaction mixture is stirred into ammonia/ice water, and the solid is filtered off with suction. The filtrate is extracted with methyl tert-butyl ether. The organic phase is separated off, dried over sodium sulphate, filtered and concentrated.

This gives 6.4 g (16.6% of theory) of N-[1-(4-bromo-2-fluorophenyl)-4-(2,6-difluorophenyl)-4-oxobutyl]acetamide of log P (pH 2.3)=2.74.

Step 4

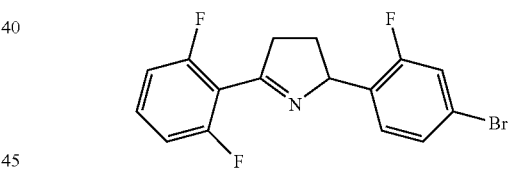

N-[1-(4-Bromo-2-fluorophenyl)-4-(2,6-difluorophenyl)-4-oxobutyl]acetamide (36 g, 86.9 mmol) is stirred in 6 N hydrochloric acid and ethanol at 100° C. for 24 h. After cooling, the mixture is poured into ice/aqueous sodium hydroxide solution and extracted with ethyl acetate. The organic phase is separated off, dried over sodium sulphate, filtered and concentrated. Crystallized solid is filtered off with suction and washed with ethyl acetate/cyclohexane 1:10.

Concentration of the filtrate gives 10.0 g (30.5% of theory) of 2-(4-bromo-2-fluorophenyl)-5-(2,6-difluorophenyl)-3,4-dihydro-2H-pyrrole.

$^1$H-NMR (400 MHz, CD$_3$CN): δ=7.45 (m, 1 H), 7.35 (m, 2 H), 7.30 (m, 1 H), 7.10 (t, 2 H), 5.45 (t, 1 H), 3.10 (dd, 2 H), 2.70 (m, 1 H), 1.80 (m, 1 H) ppm. LC-MS: 355.9 [M+H]$^+$ Step 5

200 ml of dioxane are added to a mixture of 2-(4-bromo-2-fluorophenyl)-5-(2,6-difluorophenyl)-3,4-dihydro-2H-pyrrole (20 g, 56.5 mmol), 4,4,4',4',5,5,5',5'-octamethyl-2, 2'-bis-1,3,2-dioxaborolane (15.8 g, 62.1 mmol), potassium acetate (16.6 g, 169.4 mmol), 1,1'-bis(diphenylphosphino)ferrocenepalladium(II) chloride (1.24 g, 1.69 mmol) and 1,1'-bis(diphenylphosphino)ferrocene (0.94 g, 1.69 mmol), and the mixture is allowed to react at 100° C. for 16 h. For work-up, 400 ml of water are added to the reaction mixture, which is then extracted twice with in each case 300 ml of ethyl acetate. The organic phase is separated off, dried over sodium sulphate, filtered and concentrated. The residue is dissolved in 100 ml of dichloromethane and purified by silica gel flash chromatography (gradient methylene chloride/ethyl acetate 10:0→9:1).

This gives 21.2 g (89.5% of theory) of 5-(2,6-difluorophenyl)-2-[2-fluoro-4-(4,4,5,5-tetramethyl-1,3,2-dioxaborolan-2-yl)phenyl]-3,4-dihydro-2H-pyrrole of log P (pH 2.3)=4.88.

The log P values given in the preparation examples and tables above are determined in accordance with EEC Directive 79/831 Annex V.A8 by HPLC (High Performance Liquid Chromatography) on a reversed-phase column (C 18). Temperature: 43° C.

In the acidic range, determination is carried out at pH 2.3 using the mobile phases 0.1% aqueous phosphoric acid and acetonitrile; linear gradient from 10% acetonitrile to 90% acetonitrile (in the tables marked with a)).

In the neutral range, determination is carried out at pH 7.5 using the mobile phases 0.01 molar aqueous phosphate buffer solution and acetonitrile; linear gradient from 10% acetonitrile to 90% acetonitrile (in the tables marked with b)).

Calibration is carried out using unbranched alkan-2-ones (of 3 to 16 carbon atoms) with known lopP values (determination of the log P values by the retention times using linear interpolation between two successive alkanones).

The lambda max values were determined in the maxima of the chromatographic signals using the UV spectra from 200 nm to 400 nm.

Use Examples

Example A

*Heliothis armigera* Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Soybean shoots (*Glycine max*) are treated by being dipped into the preparation of active compound of the desired concentration and are populated with caterpillars of the cotton bollworm (*Heliothis armigera*) while the leaves are still moist.

After the desired period of time, the kill in % is determined. 100% means that all caterpillars have been killed; 0% means that none of the caterpillars have been killed.

In this test, for example, the following compounds of the preparation examples show good activity:

TABLE A

Plant-damaging insects
*Heliothis armigera* test

| No. | Active compounds | Concentration of active compound in ppm | Kill rate in % after 7$^d$ |
|---|---|---|---|
| 1 | [structure] | 100 | 100 |
| 2 | [structure] | 100 | 100 |
| 3 | [structure] | 100 | 100 |
| 4 | [structure] | 100 | 100 |

TABLE A-continued

Plant-damaging insects
*Heliothis armigera* test

| No. | Active compounds | Concentration of active compound in ppm | Kill rate in % after 7$^d$ |
|---|---|---|---|
| 5 | | 100 | 100 |
| 6 | | 100 | 100 |
| 7 | | 100 | 100 |
| 8 | | 100 | 100 |
| 9 | | 100 | 100 |
| 10 | | 100 | 100 |
| 11 | | 100 | 100 |

TABLE A-continued

Plant-damaging insects
*Heliothis armigera* test

| No. | Active compounds | Concentration of active compound in ppm | Kill rate in % after 7$^d$ |
|---|---|---|---|
| 12 | 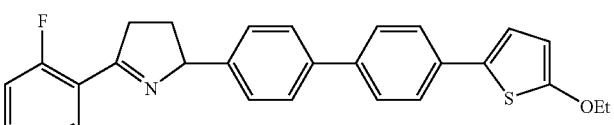 | 100 | 100 |
| 22 | 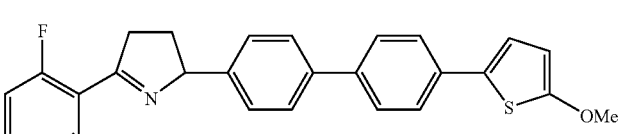 | 100 | 100 |

Example B

*Phaedon* Larvae Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the preparation examples show good activity:

TABLE B

Plant-damaging insects
*Phaedon larvae* test

| No. | Active compounds | Concentration of active compound in ppm | Kill rate in % after 7$^d$ |
|---|---|---|---|
| 1 | 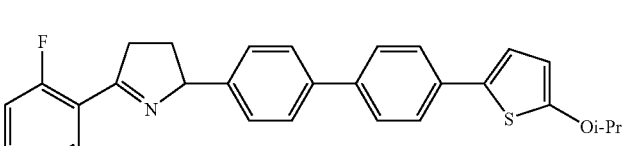 | 100 | 100 |
| 2 | | 100 | 100 |
| 3 | | 100 | 100 |

TABLE B-continued

Plant-damaging insects
*Phaedon larvae* test

| No. | Active compounds | Concentration of active compound in ppm | Kill rate in % after 7$^d$ |
|-----|------------------|------------------------------------------|-----------------------------|
| 4   | (structure)      | 100                                      | 100                         |
| 5   | (structure)      | 100                                      | 100                         |
| 6   | (structure)      | 100                                      | 100                         |
| 7   | (structure)      | 100                                      | 100                         |
| 8   | (structure, rac.)| 100                                      | 100                         |
| 9   | (structure, rac.)| 100                                      | 100                         |
| 10  | (structure, rac.)| 100                                      | 100                         |

TABLE B-continued

Plant-damaging insects
*Phaedon larvae* test

| No. | Active compounds | Concentration of active compound in ppm | Kill rate in % after 7$^d$ |
|---|---|---|---|
| 11 | [structure: 2-methylphenyl-pyrroline-biphenyl-oxadiazole with t-Bu] | 100 | 100 |
| 12 | [structure: 2-methylphenyl-pyrroline-biphenyl-oxadiazole isomer with t-Bu] | 100 | 100 |
| 18 | [structure: 2,6-difluorophenyl-pyrroline-biphenyl-pyrazole with CN] | 100 | 100 |

Example C

*Plutella* Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moth (*Plutella xylostella*) while the leaves are still moist.

After the desired period of time, the kill in % is determined. 100% means that all caterpillars have been killed; 0% means that none of the caterpillars have been killed.

In this test, for example, the following compounds of the preparation examples show good activity:

TABLE C

Plant-damaing insects
*Plutella* test

| No. | Active compounds | Concentration of active compound in ppm | Kill rate in % after 7$^d$ |
|---|---|---|---|
| 1 | [structure: 2,6-difluorophenyl-pyrroline-biphenyl-thiophene-OEt] | 100 | 100 |
| 5 | [structure: 2,6-difluorophenyl-pyrroline-fluorophenyl-phenyl-oxadiazole-t-Bu] | 100 | 100 |

TABLE C-continued

Plant-damaging insects
*Plutella* test

| No. | Active compounds | Concentration of active compound in ppm | Kill rate in % after 7$^d$ |
|---|---|---|---|
| 6 | 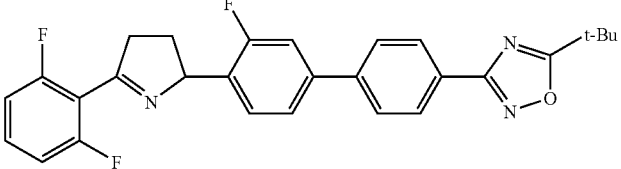 | 100 | 100 |
| 7 | 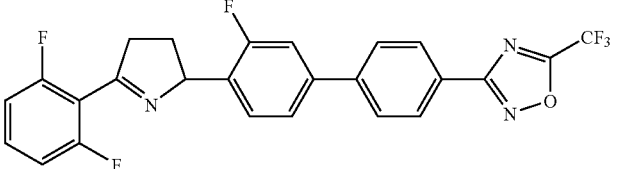 | 100 | 100 |
| 22 | 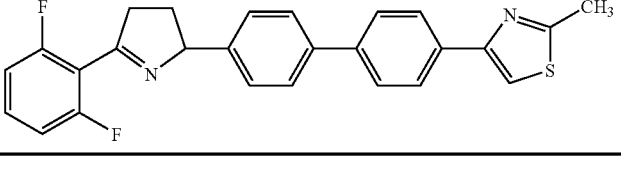 | 100 | 100 |

Example D

*Spodoptera exigua* Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera exigua*) while the leaves are still moist.

After the desired period of time, the kill in % is determined. 100% means that all caterpillars have been killed; 0% means that none of the caterpillars have been killed.

In this test, for example, the following compounds of the preparation examples show good activity:

TABLE D

Plant-damaging insects
*Spodoptera exigua* test

| No. | Active compounds | Concentration of active compound in ppm | Kill rate in after 7$^d$ |
|---|---|---|---|
| 5 | 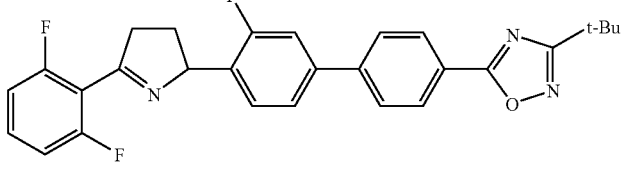 | 100 | 100 |

TABLE D-continued

Plant-damaging insects
*Spodoptera exigua* test

| No. | Active compounds | Concentration of active compound in ppm | Kill rate in after 7$^d$ |
|---|---|---|---|
| 6 | 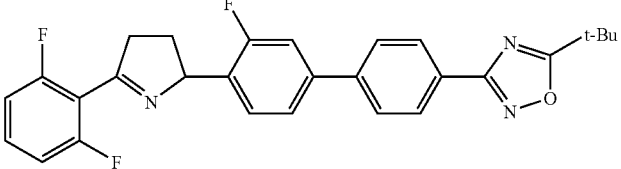 | 100 | 100 |
| 7 | 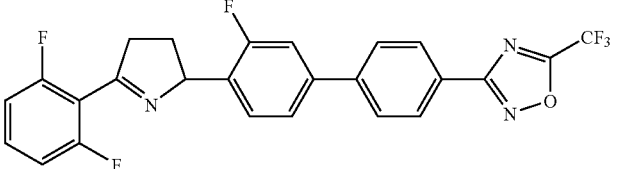 | 100 | 100 |

Example E

*Spodoptera frugiperda* Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the preparation examples show good activity:

TABLE E

Plant-damaging insects
*Spodoptera frugiperda* test

| No. | Active compounds | Concentration of active compound in ppm | Kill rate in % after 7$^d$ |
|---|---|---|---|
| 1 | 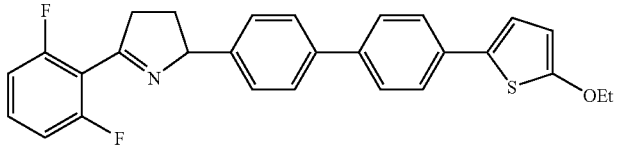 | 100 | 100 |
| 2 | 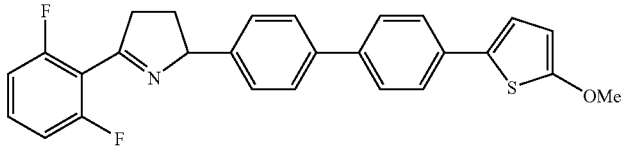 | 100 | 100 |
| 3 | 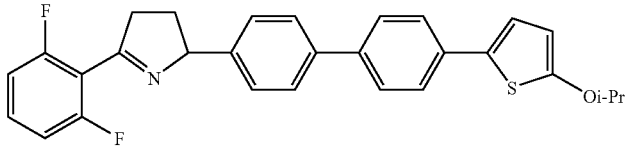 | 100 | 100 |

TABLE E-continued

Plant-damaging insects
*Spodoptera frugiperda* test

| No. | Active compounds | Concentration of active compound in ppm | Kill rate in % after 7$^d$ |
|---|---|---|---|
| 4 | | 100 | 100 |
| 5 | | 100 | 100 |
| 6 | | 100 | 100 |
| 7 | | 100 | 100 |
| 8 | | 100 | 100 |
| 9 | | 100 | 100 |
| 10 | | 100 | 100 |

TABLE E-continued

Plant-damaging insects
*Spodoptera frugiperda* test

| No. | Active compounds | Concentration of active compound in ppm | Kill rate in % after 7$^d$ |
|---|---|---|---|
| 11 | 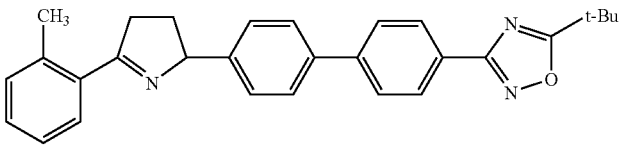 | 100 | 100 |
| 12 | 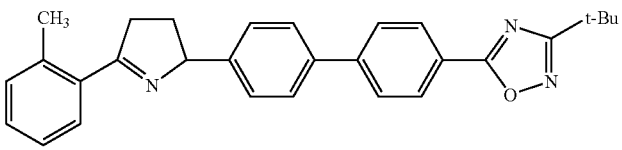 | 100 | 100 |
| 18 | 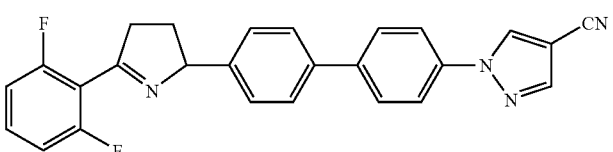 | 100 | 100 |
| 22 | 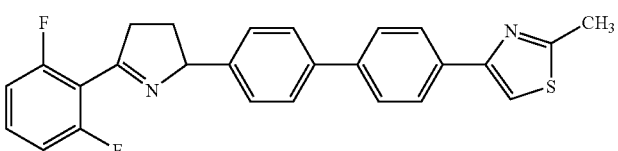 | 100 | 100 |

Example F

*Tetranychus* Test (OP-Resistant/Dip Treatment)
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are treated by being dipped into a preparation of active compound of the desired concentration.

After the desired period of time, the activity in % is determined. 100% means that all spider mites have been killed; 0% means that none of the spider mites have been killed.

In this test, for example, the following compounds of the preparation examples show good efficacy:

TABLE F

Plant-damaging mites
*Tetranychus* test (OP-resistant/dip treatment)

| No. | Active compounds | Concentration of active compound in ppm | Kill rate in % after 7$^d$ |
|---|---|---|---|
| 1 |  | 100 | 95 |

TABLE F-continued
Plant-damaging mites
*Tetranychus* test (OP-resistant/dip treatment)
| No. | Active compounds | Concentration of active compound in ppm | Kill rate in % after 7$^d$ |
|---|---|---|---|
| 4 | 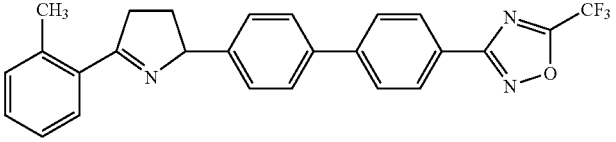 | 100 | 95 |
| 5 | 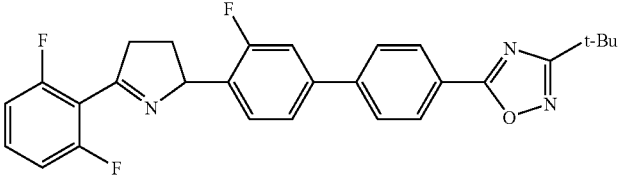 | 100 | 98 |
| 6 | 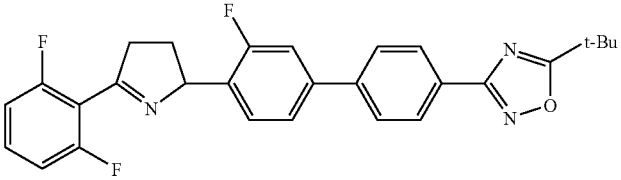 | 100 | 98 |
| 7 | 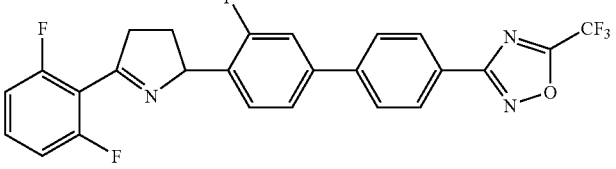 | 100 | 98 |
| 8 | 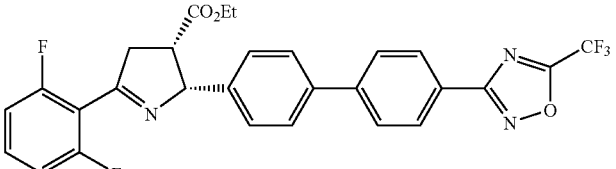 rac. | 100 | 95 |
| 11 | 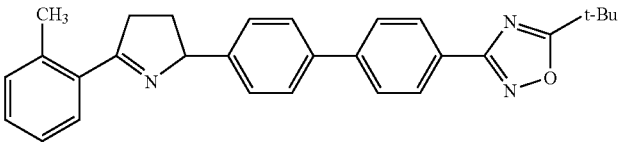 | 100 | 98 |
| 12 | 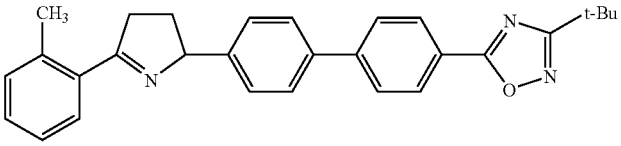 | 100 | 98 |
| 13 | 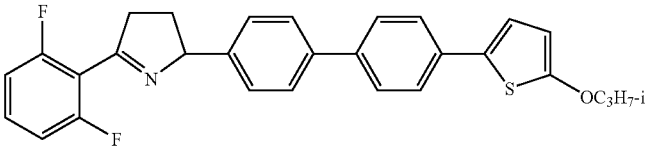 | 100 | 98 |

TABLE F-continued

Plant-damaging mites
*Tetranychus* test (OP-resistant/dip treatment)

| No. | Active compounds | Concentration of active compound in ppm | Kill rate in % after 7$^d$ |
|---|---|---|---|
| 18 | | 100 | 90 |
| 22 | | 100 | 90 |

Example G

*Diabrotica balteata* Test (Larvae in Soil)

Critical Concentration Test/Soil Insects—Treatment of Transgenic Plants
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually irrelevant, only the amount by weight of active compound per volume unit of soil, which is stated in ppm (mg/l), matters. The soil is filled into 0.25 l pots and these are allowed to stand at 20° C.

Immediately after preparation, 5 pre-germinated maize corns of the cultivar YIELD GUARD (trade mark of Monsanto Comp., USA) are placed into each pot. After 2 days, the test insects in question are placed into the treated soil. After a further 7 days, the efficacy of the active compound is determined by counting the maize plants that have emerged (1 plant=20% efficacy).

Example H

*Heliothis virescens* Test (Treatment of Transgenic Plants)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trade mark of Monsanto Comp. USA) are treated by being dipped into the preparation of active compound of the desired concentration and are populated with the tobacco bollworm *Heliothis virescens* while the leaves are still moist.

After the desired period of time, the kill in % is determined. 100% means that all caterpillars have been killed; 0% means that none of the caterpillars have been killed.

What is claimed is:
1. A pyrroline of formula (I)

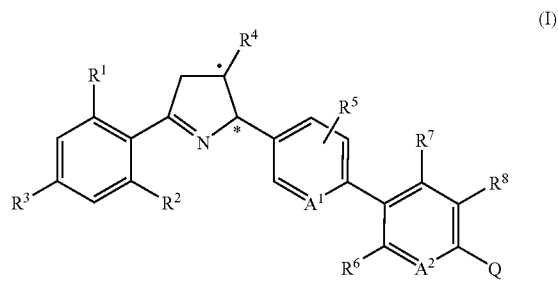

in which
R$^1$ represents halogen, C$_1$-C$_4$-alkyl, or C$_1$-C$_4$-haloalkyl,
R$^2$ represents hydrogen, halogen, C$_1$-C$_4$-alkyl, or C$_1$-C$_4$-haloalkyl,
R$^3$ represents hydrogen, halogen, or methyl,
R$^4$ represents hydrogen, C$_1$-C$_6$-alkyl, (C$_1$-C$_6$-alkoxy)carbonyl, (C$_3$-C$_6$-cycloalkyl)oxycarbonyl, or (C$_1$-C$_6$-haloalkoxy)carbonyl; or represents aryl that is optionally mono- or polysubstituted by identical or different substituents selected from the group consisting of halogen, cyano, nitro, C$_1$-C$_4$-alkyl, C$_1$-C$_4$-alkoxy, C$_1$-C$_4$-alkylthio, C$_1$-C$_4$-haloalkyl, C$_1$-C$_4$-haloalkoxy, and C$_1$-C$_4$-haloalkylthio,
A$^1$ represents N or CH,
A$^2$ represents CR$^9$,
R$^5$ represents hydrogen, halogen, C$_1$-C$_6$-alkyl, C$_1$-C$_6$-alkoxy, C$_1$-C$_6$-alkylthio, C$_1$-C$_6$-alkylsulphinyl, C$_1$-C$_6$-alkylsulphonyl, C$_1$-C$_6$-haloalkoxy, C$_1$-C$_6$-haloalkylthio, C$_1$-C$_6$-haloalkylsulphinyl, or C$_1$-C$_6$-haloalkylsulphonyl,
R$^6$, R$^7$, R$^8$, and R$^9$ independently of one another represent hydrogen, halogen, cyano, formyl, nitro, tri(C$_1$-C$_6$-alkyl)silyl, C$_1$-C$_6$-alkyl, C$_1$-C$_6$-alkoxy, C$_1$-C$_6$-alkylthio, C$_1$-C$_6$-alkylsulphinyl, C$_1$-C$_6$-alkylsulphonyl, $C_2$-$C_6$-alkenyl, $C_2$-$C_6$-alkenyloxy, ($C_1$-$C_6$-alkyl)carbonyl, ($C_1$-$C_6$-alkoxy)carbonyl, $C_1$-$C_6$-haloalkyl, $C_1$-$C_6$-haloalkoxy, $C_1$-$C_6$-haloalkylthio, $C_1$-$C_6$-haloalkylsulphinyl, $C_1$-$C_6$-haloalkylsulphonyl, $C_2$-$C_6$-haloalkenyl, $C_2$-$C_6$-haloalkenyloxy, ($C_1$-$C_6$-haloalkyl)carbonyl, ($C_1$-$C_6$-haloalkoxy)carbonyl, pentafluorothio, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$ or —OSO$_2$N$R^{12}R^{13}$, $R^{10}$ represents hydrogen, $C_1$-$C_6$-alkyl, $C_2$-$C_6$-alkenyl, $C_1$-$C_6$-haloalkyl, $C_2$-$C_6$-haloalkenyl, or $C_3$-$C_6$-cycloalkyl, $R^{11}$ represents hydrogen, $C_1$-$C_6$-alkyl, $C_2$-$C_6$-alkenyl, $C_1$-$C_6$-haloalkyl, $C_2$-$C_6$-haloalkenyl, or $C_3$-$C_6$-cycloalkyl-$C_1$-$C_4$-alkyl; or represents aryl-$C_1$-$C_4$-alkyl that is optionally mono- or polysubstituted by identical or different radicals $R^5$, $R^{12}$ and $R^{13}$ independently of one another represent hydrogen, $C_1$-$C_6$-alkyl, or $C_1$-$C_6$-haloalkyl; represent $C_3$-$C_6$-cycloalkyl which is optionally mono- or polysubstituted by identical or different substituents selected from the group consisting of halogen and $C_1$-$C_6$-alkyl; represents $C_3$-$C_6$-cycloalkyl-$C_1$-$C_4$-alkyl; or represents aryl-$C_1$-$C_4$-alkyl that is optionally mono- or polysubstituted by identical or different radicals $R^5$, or $R^{12}$ and $R^{13}$ together represent $C_2$-$C_6$-alkylene, ($C_1$-$C_3$-alkoxy)-$C_1$-$C_3$-alkylene, or ($C_1$-$C_3$-alkylthio)-$C_1$-$C_3$-alkylene, each of which is optionally mono- or polysubstituted by identical or different substituents selected from the group consisting of halogen and $C_1$-$C_6$-alkyl, p represents 0, 1, or 2, Q represents a completely unsaturated 5-membered heterocycle that has 1 to 3 identical or different heteroatoms selected from the group consisting of nitrogen, oxygen, and sulphur and that is mono- or polysubstituted by identical or different radicals selected from $W^1$, $W^1$ represents halogen, cyano, $C_1$-$C_{16}$-alkyl, $C_1$-$C_{16}$-alkoxy, $C_1$-$C_{16}$-alkylthio, $C_1$-$C_{16}$-alkylsulphinyl, $C_1$-$C_{16}$-alkylsulphonyl, $C_1$-$C_{16}$-haloalkyl, $C_1$-$C_{16}$-haloalkoxy, $C_1$-$C_{16}$-haloalkylthio, $C_1$-$C_{16}$-haloalkylsulphinyl, $C_1$-$C_{16}$-haloalkylsulphonyl, or $C_3$-$C_{12}$-cycloalkyl; or represents aryl or aryl-$C_1$-$C_4$-alkyl, each of which is optionally mono- or polysubstituted by identical or different substituents selected from the group consisting of halogen, cyano, formyl, nitro, tri($C_1$-$C_6$-alkyl)silyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_2$-$C_6$-alkenyl, $C_2$-$C_6$-alkenyloxy, ($C_1$-$C_6$-alkyl)carbonyl, ($C_1$-$C_6$-alkoxy)carbonyl, $C_1$-$C_6$-haloalkyl, $C_1$-$C_6$-haloalkoxy, $C_1$-$C_6$-haloalkylthio, $C_1$-$C_6$-haloalkylsulphinyl, $C_1$-$C_6$-haloalkylsulphonyl, $C_2$-$C_6$-haloalkenyl, $C_2$-$C_6$-haloalkenyloxy, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, the symbol * denotes a stereogenic center and the symbol • denotes a further stereogenic center when $R^4$ does not represent hydrogen, wherein the substituents at the two stereogenic centers are located at cis- or trans-positions relative to each other.

2. A pyrroline of formula (I) according to claim 1 in which $R^1$ represents fluorine, chlorine, bromine, $C_1$-$C_4$-alkyl, or $C_1$-$C_4$-haloalkyl having 1 to 9 fluorine, chlorine, and/or bromine atoms, $R^2$ represents hydrogen, fluorine, chlorine, bromine, $C_1$-$C_4$-alkyl, or $C_1$-$C_4$-haloalkyl having 1 to 9 fluorine, chlorine, and/or bromine atoms, $R^3$ represents hydrogen, fluorine, chlorine, bromine, or methyl, $R^4$ represents hydrogen, $C_1$-$C_4$-alkyl, ($C_1$-$C_4$-alkoxy)carbonyl, ($C_3$-$C_6$-cycloalkyl)oxycarbonyl, or ($C_1$-$C_4$-haloalkoxy)carbonyl having 1 to 9 fluorine and/or chlorine atoms; or represents phenyl that is optionally mono- to tetrasubstituted by identical or different substituents selected from the group consisting of fluorine, chlorine, bromine, iodine, cyano, nitro, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, and $C_1$-$C_4$-haloalkylthio having in each case 1 to 9 fluorine, chlorine, and/or bromine atoms, $A^1$ represents N or CH, $A^2$ represents C$R^9$, $R^5$ represents hydrogen, fluorine, chlorine, bromine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl; $C_1$-$C_4$-haloalkoxy, $C_1$-$C_4$-haloalkylthio, $C_1$-$C_4$-haloalkylsulphinyl, or $C_1$-$C_4$-haloalkylsulphonyl having in each case 1 to 9 fluorine, chlorine, and/or bromine atoms, $R^6$, $R^7$, $R^8$, and $R^9$ independently of one another represent hydrogen, fluorine, chlorine, bromine, cyano, formyl, nitro, tri($C_1$-$C_4$-alkyl)silyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl; $C_1$-$C_4$-haloalkyl, $C_1$-$C_4$-haloalkoxy, $C_1$-$C_4$-haloalkylthio, $C_1$-$C_4$-haloalkylsulphinyl, or $C_1$-$C_4$-haloalkylsulphonyl having in each case 1 to 9 fluorine, chlorine, and/or bromine atoms; represent $C_2$-$C_4$-haloalkenyl or $C_2$-$C_4$-haloalkenyloxy having in each case 1 to 7 fluorine, chlorine, and/or bromine atoms; represent ($C_1$-$C_4$-haloalkyl)carbonyl or ($C_1$-$C_4$-haloalkoxy)carbonyl, having in each case 1 to 9 fluorine, chlorine, and/or bromine atoms; or represent pentafluorothio, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, or —OSO$_2$N$R^{12}R^{13}$, $R^{10}$ represents hydrogen, $C_1$-$C_4$-alkyl, $C_2$-$C_4$-alkenyl, $C_1$-$C_4$-haloalkyl having 1 to 9 fluorine, chlorine, and/or bromine atoms, $C_2$-$C_4$-haloalkenyl having 1 to 7 fluorine, chlorine, and/or bromine atoms, cyclopropyl, cyclopentyl, or cyclohexyl, $R^{11}$ represents hydrogen, $C_1$-$C_4$-alkyl, $C_2$-$C_4$-alkenyl, $C_1$-$C_4$-haloalkyl having 1 to 9 fluorine, chlorine, and/or bromine atoms, $C_2$-$C_4$-haloalkenyl having 1 to 7 fluorine, chlorine, and/or bromine atoms, or $C_3$-$C_6$-cycloalkyl-$C_1$-$C_2$-alkyl; or represents benzyl or phenylethyl, each of which is optionally mono- to tetrasubstituted by identical or different radicals $R^5$, $R^{12}$ and $R^{13}$ independently of one another represent hydrogen, $C_1$-$C_4$-alkyl, $C_1$-$C_4$-haloalkyl having 1 to 9 fluorine, chlorine, and/or bromine atoms, $C_3$-$C_6$-cycloalkyl, or $C_3$-$C_6$-cycloalkyl-$C_1$-$C_2$-alkyl; or represents benzyl or phenylethyl, each of which is optionally mono- to tetrasubstituted by identical or different radicals $R^5$, or $R^{12}$ and $R^{13}$ together represent $C_3$-$C_5$-alkylene, —(CH$_2$)$_2$—O—(CH$_2$)$_2$—, or —(CH$_2$)$_2$—S—(CH$_2$)$_2$—, p represents 0 or 1, Q represents a completely unsaturated 5-membered heterocycle that has 1 to 3 identical or different heteroatoms selected from the group consisting of nitrogen, oxygen, and sulphur and that is mono- or polysubstituted by identical or different radicals selected from $W^1$, and $W^1$ represents fluorine, chlorine, bromine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, $C_1$-$C_{12}$-haloalkoxy, $C_1$-$C_{12}$-haloalkylthio, $C_1$-$C_{12}$-haloalkylsulphinyl, $C_1$-$C_{12}$-haloalkylsulphonyl, or $C_3$-$C_{12}$-cycloalkyl; or represents phenyl or aryl-$C_1$-$C_2$-alkyl, each of which is optionally mono- or polysubstituted by identical or different substituents selected from the group consisting of fluorine, chlorine, bromine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$.

3. A pyrroline of formula (I) according to claim 1 in which Q represents a completely unsaturated 5-membered heterocycle selected from the group consisting of

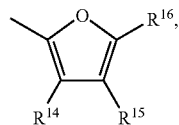 Q1

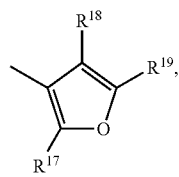 Q2

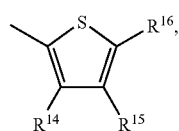 Q3

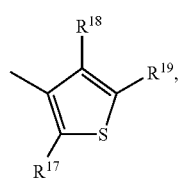 Q4

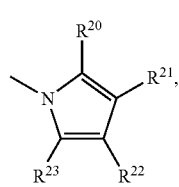 Q5

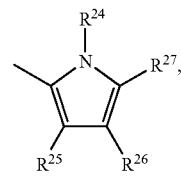 Q6

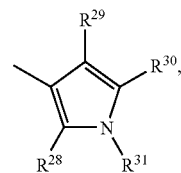 Q7

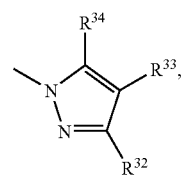 Q8

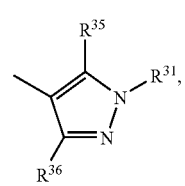 Q9

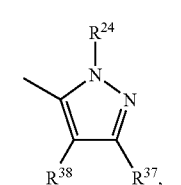 Q10

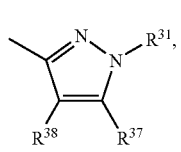 Q11

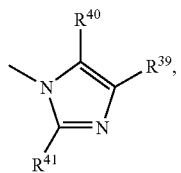 Q12

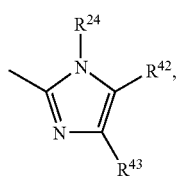 Q13

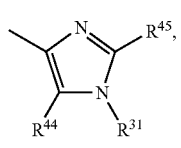 Q14

-continued
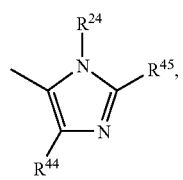 Q15
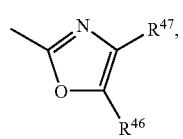 Q16
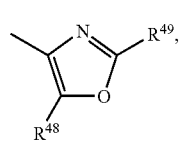 Q17
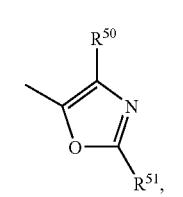 Q18
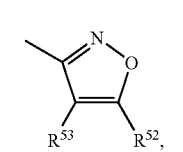 Q19
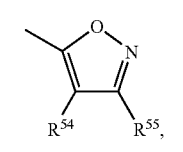 Q20
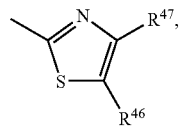 Q21
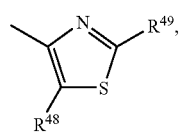 Q22
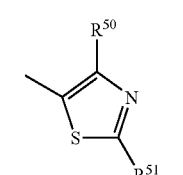 Q23
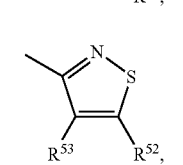 Q24
-continued
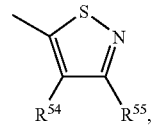 Q25
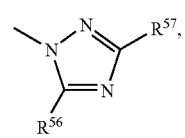 Q26
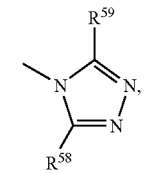 Q27
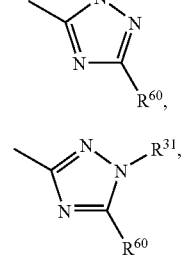 Q28
Q29
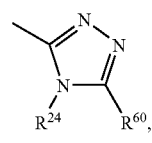 Q30
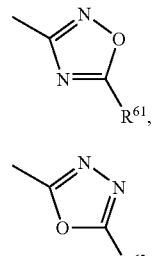 Q31
Q32
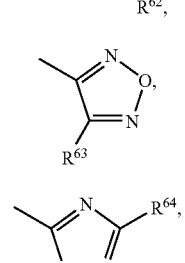 Q33
Q34
Q35

-continued

Q36

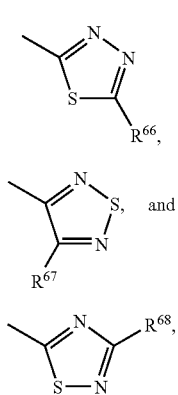

Q37

Q38 in which
R$^{14}$ and R$^{15}$ independently of one another represent hydrogen, chlorine, cyano, C$_1$-C$_{12}$-alkyl, C$_1$-C$_{12}$-alkoxy, C$_1$-C$_{12}$-alkylthio, C$_1$-C$_{12}$-alkylsulphinyl, C$_1$-C$_{12}$-alkylsulphonyl, C$_1$-C$_{12}$-haloalkyl, or C$_3$-C$_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, C$_2$-C$_4$-alkenyl, C$_2$-C$_4$-alkenyloxy, (C$_1$-C$_4$-alkyl)carbonyl, (C$_1$-C$_4$-alkoxy)carbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkylsulphonyl having in each case 1 to 9 fluorine, chlorine, and/or bromine atoms, C$_2$-C$_4$-haloalkenyl, C$_2$-C$_4$-haloalkenyloxy having in each case 1 to 7 fluorine, chlorine, and/or bromine atoms, —C(R$^{10}$)=N—OR$^{11}$, —SO$_2$NR$^{12}$R$^{13}$, —(CH$_2$)$_p$NR$^{12}$R$^{13}$, —(CH$_2$)$_p$N(R$^{12}$)COR$^{13}$, —(CH$_2$)$_p$N(R$^{12}$)SO$_2$R$^{13}$, —OSO$_2$R$^{12}$, and —OSO$_2$NR$^{12}$R$^{13}$, where R$^{10}$ to R$^{13}$ are as defined in claim 1, R$^{16}$ represents hydrogen, cyano, C$_1$-C$_{12}$-alkyl, C$_1$-C$_{12}$-alkoxy, C$_1$-C$_{12}$-alkylthio, C$_1$-C$_{12}$-alkylsulphinyl, C$_1$-C$_{12}$-alkylsulphonyl, C$_1$-C$_{12}$-haloalkyl, or C$_3$-C$_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, C$_2$-C$_4$-alkenyl, C$_2$-C$_4$-alkenyloxy, (C$_1$-C$_4$-alkyl)carbonyl, (C$_1$-C$_4$-alkoxy)carbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkylsulphonyl having in each case 1 to 9 fluorine, chlorine, and/or bromine atoms, C$_2$-C$_4$-haloalkenyl, C$_2$-C$_4$-haloalkenyloxy having in each case 1 to 7 fluorine, chlorine, and/or bromine atoms, —C(R$^{10}$)=N—OR$^{11}$, —SO$_2$NR$^{12}$R$^{13}$, —(CH$_2$)$_p$NR$^{12}$R$^{13}$, —(CH$_2$)$_p$N(R$^{12}$)COR$^{13}$, —(CH$_2$)$_p$N(R$^{12}$)SO$_2$R$^{13}$, —OSO$_2$R$^{12}$, and —OSO$_2$NR$^{12}$R$^{13}$, where R$^{10}$ to R$^{13}$ are as defined in claim 1, with the proviso that R$^{14}$, R$^{15}$, and R$^{16}$ do not simultaneously represent hydrogen, R$^{17}$ and R$^{19}$ independently of one another represent hydrogen, cyano, C$_1$-C$_{12}$-alkyl, C$_1$-C$_{12}$-alkoxy, C$_1$-C$_{12}$-alkylthio, C$_1$-C$_{12}$-alkylsulphinyl, C$_1$-C$_{12}$-alkylsulphonyl, C$_1$-C$_{12}$-haloalkyl, or C$_3$-C$_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, C$_2$-C$_4$-alkenyl, C$_2$-C$_4$-alkenyloxy, (C$_1$-C$_4$-alkyl)carbonyl, (C$_1$-C$_4$-alkoxy)carbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkylsulphonyl having in each case 1 to 9 fluorine, chlorine, and/or bromine atoms, C$_2$-C$_4$-haloalkenyl, C$_2$-C$_4$-haloalkenyloxy having in each case 1 to 7 fluorine, chlorine, and/or bromine atoms, —C(R$^{10}$)=N—OR$^{11}$, —SO$_2$NR$^{12}$R$^{13}$, —(CH$_2$)$_p$NR$^{12}$R$^{13}$, —(CH$_2$)$_p$N(R$^{12}$)COR$^{13}$, —(CH$_2$)$_p$N(R$^{12}$)SO$_2$R$^{13}$, —OSO$_2$R$^{12}$, and —OSO$_2$NR$^{12}$R$^{13}$, where R$^{10}$ to R$^{13}$ are as defined in claim 1, R$^{18}$ represents hydrogen, chlorine, cyano, C$_1$-C$_{12}$-alkyl, C$_1$-C$_{12}$-alkoxy, C$_1$-C$_{12}$-alkylthio, C$_1$-C$_{12}$-alkylsulphinyl, C$_1$-C$_{12}$-alkylsulphonyl, C$_1$-C$_{12}$-haloalkyl, or C$_3$-C$_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, C$_2$-C$_4$-alkenyl, C$_2$-C$_4$-alkenyloxy, (C$_1$-C$_4$-alkyl)carbonyl, (C$_1$-C$_4$-alkoxy)carbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkylsulphonyl having in each case 1 to 9 fluorine, chlorine, and/or bromine atoms, C$_2$-C$_4$-haloalkenyl, C$_2$-C$_4$-haloalkenyloxy having in each case 1 to 7 fluorine, chlorine, and/or bromine atoms, —C(R$^{10}$)=N—OR$^{11}$, —SO$_2$NR$^{12}$R$^{13}$, —(CH$_2$)$_p$NR$^{12}$R$^{13}$, —(CH$_2$)$_p$N(R$^{12}$)COR$^{13}$, —(CH$_2$)$_p$N(R$^{12}$)SO$_2$R$^{13}$, —OSO$_2$R$^{12}$, and —OSO$_2$NR$^{12}$R$^{13}$, where R$^{10}$ to R$^{13}$ are as defined in claim 1, with the proviso that R$^{17}$, R$^{18}$, and R$^{19}$ do not simultaneously represent hydrogen, R$^{20}$ and R$^{23}$ independently of one another represent hydrogen, C$_1$-C$_{12}$-alkyl, C$_1$-C$_{12}$-alkoxy, C$_1$-C$_{12}$-alkylthio, C$_1$-C$_{12}$-alkylsulphinyl, C$_1$-C$_{12}$-alkylsulphonyl, C$_1$-C$_{12}$-haloalkyl, or C$_3$-C$_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, C$_1$-C$_4$-alkyl, C$_1$-C$_4$-alkoxy, C$_1$-C$_4$-alkylthio, C$_1$-C$_4$-alkylsulphinyl, C$_1$-C$_4$-alkylsulphonyl, C$_2$-C$_4$-alkenyl, C$_2$-C$_4$-alkenyloxy, (C$_1$-C$_4$-alkyl)carbonyl, (C$_1$-C$_4$-alkoxy)carbonyl, C$_1$-C$_4$-haloalkyl, C$_1$-C$_4$-haloalkoxy, C$_1$-C$_4$-haloalkylthio, C$_1$-C$_4$-haloalkylsulphinyl, C$_1$-C$_4$-haloalkylsulphonyl having in each case 1 to 9 fluorine, chlorine, and/or bromine atoms, C$_2$-C$_4$-haloalkenyl, C$_2$-C$_4$-haloalkenyloxy having in each case 1 to 7 fluorine, chlorine, and/or bromine atoms, —C(R$^{10}$)=N—OR$^{11}$, —SO$_2$NR$^{12}$R$^{13}$, —(CH$_2$)$_p$NR$^{12}$R$^{13}$, —(CH$_2$)$_p$N(R$^{12}$)COR$^{13}$, —(CH$_2$)$_p$N(R$^{12}$)SO$_2$R$^{13}$, —OSO$_2$R$^{12}$, and —OSO$_2$NR$^{12}$R$^{13}$, where R$^{10}$ to R$^{13}$ are as defined in claim 1, R$^{21}$ and R$^{22}$ independently of one another represent hydrogen, chlorine, cyano, C$_1$-C$_{12}$-alkyl, C$_1$-C$_{12}$-alkoxy, C$_1$-C$_{12}$-alkylthio, C$_1$-C$_{12}$-alkylsulphinyl, C$_1$-C$_{12}$-alkylsulphonyl, C$_1$-C$_{12}$-haloalkyl, or C$_3$-C$_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_p NR^{12}R^{13}$, —$(CH_2)_p N(R^{12})COR^{13}$, —$(CH_2)_p N(R^{12})SO_2R^{13}$, —$OSO_2R^{12}$, and —$OSO_2NR^{12}R^{13}$, where $R^{10}$ to $R^{13}$ are as defined in claim 1, with the proviso that $R^{20}$, $R^{21}$, $R^{22}$, and $R^{23}$ do not simultaneously represent hydrogen, $R^{24}$ represents hydrogen, $C_1$-$C_6$-alkyl, or $C_3$-$C_6$-cycloalkyl, $R^{25}$ and $R^{26}$ independently of one another represent hydrogen, chlorine, cyano, $C_1$-$C_{12}$-alkyl, $C_1$-$C_{12}$-alkoxy, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_p NR^{12}R^{13}$, —$(CH_2)_p N(R^{12})COR^{13}$, —$(CH_2)_p N(R^{12})SO_2R^{13}$, —$OSO_2R^{12}$, and —$OSO_2NR^{12}R^{13}$, where $R^{10}$ to $R^{13}$ are as defined in claim 1, $R^{27}$ represents hydrogen, $C_1$-$C_{12}$-alkyl, $C_1$-$C_{12}$-alkoxy, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_p NR^{12}R^{13}$, —$(CH_2)_p N(R^2)COR^{13}$, —$(CH_2)_p N(R^{12})SO_2R^{13}$, —$OSO_2R^{12}$, and —$OSO_2NR^{12}R^{13}$, where $R^{10}$ to $R^{13}$ are as defined in claim 1, with the proviso that $R^{24}$, $R^{25}$, $R^{26}$, and $R^{27}$ do not simultaneously represent hydrogen, $R^{28}$ and $R^{30}$ independently of one another represent hydrogen, $C_1$-$C_{12}$-alkyl, $C_1$-$C_{12}$-alkoxy, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_p NR^{12}R^{13}$, —$(CH_{12})_p N(R^{12})COR^{13}$, —$(CH_2)_p N(R^2)SO_2R^{13}$, —$OSO_2R^{12}$, and —$OSO_2NR^{12}R^{13}$, where $R^{10}$ to $R^{13}$ are as defined in claim 1, $R^{29}$ represents hydrogen, chlorine, cyano, $C_1$-$C_{12}$-alkyl, $C_1$-$C_{12}$-alkoxy, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_p NR^{12}R^{13}$, —$(CH_2)_p N(R^{12})COR^{13}$, —$(CH_2)_p N(R^{12})SO_2R^{13}$, —$OSO_2R^{12}$, and —$OSO_2NR^{12}R^{13}$, where $R^{10}$ to $R^{13}$ are as defined in claim 1, $R^{31}$ represents hydrogen, $C_1$-$C_6$-alkyl, or $C_3$-$C_6$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_p NR^{12}R^{13}$, —$(CH_2)_p N(R^{12})COR^{13}$, —$(CH_2)_p N(R^{12})SO_2R^{13}$, —$OSO_2R^{12}$, and —$OSO_2NR^{12}R^{13}$, where $R^{10}$ to $R^{13}$ are as defined in claim 1, with the proviso that $R^{28}$, $R^{29}$, $R^{30}$, and $R^{31}$ do not simultaneously represent hydrogen, $R^{32}$ and $R^{34}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$, and —$OSO_2NR^{12}R^{13}$, where $R^{10}$ to $R^{13}$ are as defined in claim 1, $R^{33}$ represents hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$, and —$OSO_2NR^{12}R^{13}$, where $R^{10}$ to $R^{13}$ are as defined in claim 1, with the proviso that $R^{32}$, $R^{33}$, and $R^{34}$ do not simultaneously represent hydrogen, $R^{35}$ and $R^{36}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$, and —$OSO_2NR^{12}R^{13}$, where $R^{10}$ to $R^{13}$ are as defined in claim 1, with the proviso that $R^{31}$, $R^{35}$, and $R^{36}$ do not simultaneously represent hydrogen, $R^{37}$ represents hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$, and —$OSO_2NR^{12}R^{13}$, where $R^{10}$ to $R^{13}$ are as defined in claim 1, $R^{38}$ represents hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$ and —$OSO_2NR^{12}R^{13}$, where $R^{10}$ to $R^{13}$ are as defined in claim 1, with the proviso that $R^{24}$, $R^{37}$, and $R^{38}$ or $R^{31}$, $R^{37}$, and $R^{38}$ do not simultaneously represent hydrogen, $R^{39}$, $R^{40}$ and $R^{41}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—$OR^{11}$, —$SO_2NR^{12}R^{13}$, —$(CH_2)_pNR^{12}R^{13}$, —$(CH_2)_pN(R^{12})COR^{13}$, —$(CH_2)_pN(R^{12})SO_2R^{13}$, —$OSO_2R^{12}$, and —$OSO_2NR^{12}R^{13}$, where $R^{10}$ to $R^{13}$ are as defined in claim 1, with the proviso that $R^{39}$, $R^{40}$, and $R^{41}$ do not simultaneously represent hydrogen, $R^{42}$ and $R^{43}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, with the proviso that $R^{24}$, $R^{42}$, and $R^{43}$ do not simultaneously represent hydrogen, $R^{44}$ and $R^{45}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, with the proviso that $R^{24}$, $R^{44}$, and $R^{45}$ or $R^{31}$, $R^{44}$, and $R^{45}$ do not simultaneously represent hydrogen, $R^{46}$ and $R^{47}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, with the proviso that $R^{46}$ and $R^{47}$ do not simultaneously represent hydrogen, $R^{48}$ and $R^{49}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, with the proviso that $R^{48}$ and $R^{49}$ do not simultaneously represent hydrogen, $R^{50}$ and $R^{51}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, with the proviso that $R^{50}$ and $R^{51}$ do not simultaneously represent hydrogen, $R^{52}$ represents hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, $R^{53}$ represents hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, $(C_1$-$C_4$-alkyl)carbonyl, $(C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, where $R^{10}$ to $R^{13}$ are as defined in claim 1, with the proviso that $R^{52}$ and $R^{53}$ do not simultaneously represent hydrogen, $R^{54}$ represents hydrogen, chlorine, cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, where $R^{10}$ to $R^{13}$ are as defined in claim 1, $R^{55}$ represents hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, where $R^{10}$ to $R^{13}$ are as defined in claim 1, with the proviso that $R^{54}$ and $R^{55}$ do not simultaneously represent hydrogen, $R^{56}$ and $R^{57}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, where $R^{10}$ to $R^{13}$ are as defined in claim 1, with the proviso that $R^{56}$ and $R^{57}$ do not simultaneously represent hydrogen, $R^{58}$ and $R^{59}$ independently of one another represent hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represent phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, where $R^{10}$ to $R^{13}$ are as defined in claim 1, with the proviso that $R^{58}$ and $R^{59}$ do not simultaneously represent hydrogen, $R^{60}$ represents hydrogen, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, where $R^{10}$ to $R^{13}$ are as defined in claim 1, with the proviso that $R^{24}$ and $R^{60}$ or $R^{31}$ and $R^{60}$ do not simultaneously represent hydrogen, $R^{61}$ represents $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, $R^{62}$ represents cyano, $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, $R^{63}$ represents $C_1$-$C_{12}$-alkyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, $R^{64}$ represents $C_1$-$C_{12}$-alkyl, $C_1$-$C_{12}$-alkoxy, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, $R^{65}$ represents $C_1$-$C_{12}$-alkyl, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^3$, where $R^{10}$ to $R^{13}$ are as defined in claim 1, $R^{66}$ represents $C_1$-$C_{12}$-alkyl, $C_1$-$C_{12}$-alkylthio, $C_1$-$C_{12}$-alkylsulphinyl, $C_1$-$C_{12}$-alkylsulphonyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, $R^{67}$ represents $C_1$-$C_{12}$-alkyl, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})COR^{13}$, $-(CH_2)_pN(R^{12})SO_2R^{13}$, $-OSO_2R^{12}$, and $-OSO_2NR^{12}R^{13}$, where $R^{10}$ to $R^{13}$ are as defined in claim 1, and $R^{68}$ represents $C_1$-$C_{12}$-alkyl, $C_1$-$C_{12}$-alkoxy, $C_1$-$C_{12}$-haloalkyl, or $C_3$-$C_{12}$-cycloalkyl; or represents phenyl or benzyl, each of which is optionally mono- to tetrasubstituted by identical or different substituents selected from the group consisting of fluorine, chlorine, cyano, formyl, nitro, trimethylsilyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_2$-$C_4$-alkenyl, $C_2$-$C_4$-alkenyloxy, ($C_1$-$C_4$-alkyl)carbonyl, ($C_1$-$C_4$-alkoxy)carbonyl, $C_1$-$C_4$-haloalkyl, $C_1$-$C_4$-haloalkoxy, $C_1$-$C_4$-haloalkylthio, $C_1$-$C_4$-haloalkylsulphinyl, $C_1$-$C_4$-haloalkylsulphonyl having in each case 1 to 9 fluorine, chlorine, and/or bromine atoms, $C_2$-$C_4$-haloalkenyl, $C_2$-$C_4$-haloalkenyloxy having in each case 1 to 7 fluorine, chlorine, and/or bromine atoms, $-C(R^{10})=N-OR^{11}$, $-SO_2NR^{12}R^{13}$, $-(CH_2)_pNR^{12}R^{13}$, $-(CH_2)_pN(R^{12})$ COR¹³, —(CH₂)ₚN(R¹²)SO₂R¹³, —OSO₂R¹², and —OSO₂NR¹²R¹³, where R¹⁰ to R¹³ are as defined in claim 1.

4. A pyrroline of formula (I) according to claim 1 in which A¹ and A² each represent CH.

5. A pyrroline of formula (I-b) according to claim 1 in which

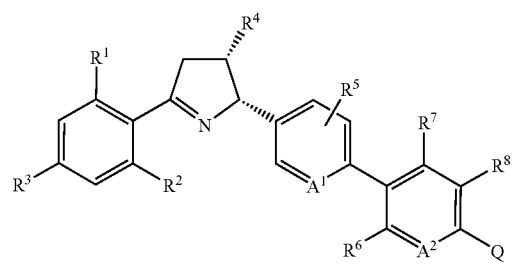
(I-b)

in which
A¹, A², R¹, R², R³, R⁵, R⁶, R⁷, R⁸, and Q are as defined for formula (I) in claim 1,
R⁴ is as defined for formula (I) in claim 1 but does not represent hydrogen, the carbon atom in the 2-position of the pyrrole ring has the R configuration, and the two substituents in the 2- and 3-positions of the pyrrole ring are located cis to each other.

6. A pyrroline of formula (I-a) according to claim 1 in which

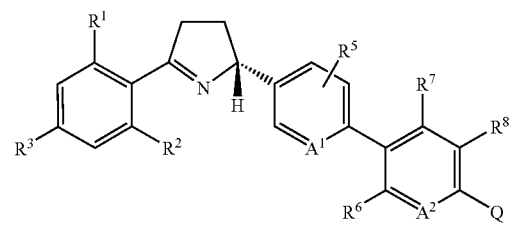
(I-a)

in which
A¹, A², R¹, R², R³, R⁵, R⁶, R⁷, R⁸, and Q are as defined for formula (I) in claim 1, and
the carbon atom in the 2-position of the pyrrole ring has the R configuration.

7. A pyrroline of formula (I-f) according to claim 1 in which

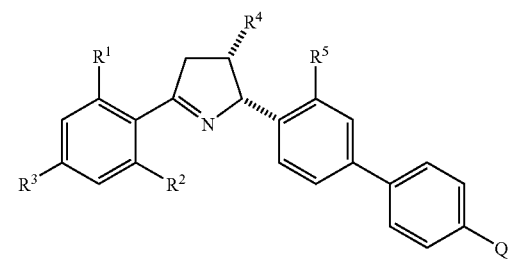
(I-f)

in which (1) R¹ is F, R² is F, R³ is H, R⁴ is H, R⁵ is H, and Q is

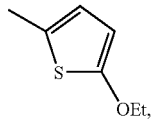

(2) R¹ is F, R² is F, R³ is H, R⁴ is H, R⁵ is H, and Q is

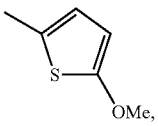

(3) R¹ is F, R² is F, R³ is H, R⁴ is H, R⁵ is H, and Q is

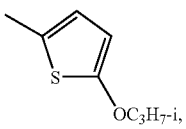

(4) R¹ is CH₃, R² is H, R³ is H, R⁴ is H, R⁵ is H, and Q is

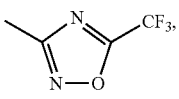

(5) R¹ is F, R² is F, R³ is H, R⁴ is H, R⁵ is F, and Q is

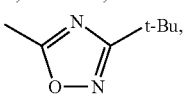

(6) R¹ is F, R² is F, R³ is H, R⁴ is H, R⁵ is H, and Q is

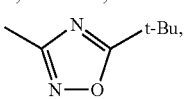

(7) R¹ is F, R² is F, R³ is H, R⁴ is H, R⁵ is F, and Q is

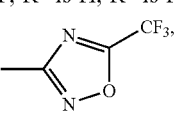

(8) R¹ is F, R² is F, R³ is H, R⁴ is CO₂Et, R⁵ is H, and Q is

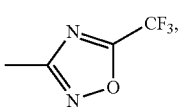

(9) R¹ is F, R² is F, R³ is H, R⁴ is CO₂Et, R⁵ is H, and Q is

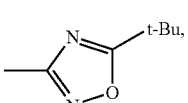

(10) $R^1$ is F, $R^2$ is F, $R^3$ is H, $R^4$ is $CO_2Et$, $R^5$ is H, and Q is

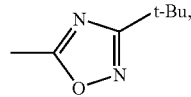

(11) $R^1$ is $CH_3$, $R^2$ is H, $R^3$ is H, $R^4$ is H, $R^5$ is H, and Q is

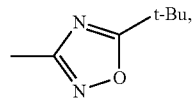

(12) $R^1$ is $CH_3$, $R^2$ is H, $R^3$ is H, $R^4$ is H, $R^5$ is H, and Q is

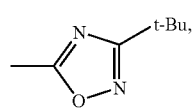

(13) $R^1$ is F, $R^2$ is F, $R^3$ is H, $R^4$ is $C_2H_5$, $R^5$ is H, and Q is

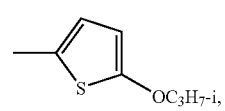

(14) $R^1$ is $CH_3$, $R^2$ is H, $R^3$ is H, $R^4$ is H, $R^5$ is F, and Q is

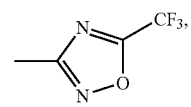

(15) $R^1$ is $CH_3$, $R^2$ is H, $R^3$ is H, $R^4$ is H, $R^5$ is F, and Q is

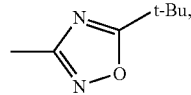

(16) $R^1$ is $CH_3$, $R^2$ is H, $R^3$ is H, $R^4$ is H, $R^5$ is F, and Q is

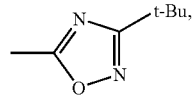

(17) $R^1$ is $CH_3$, $R^2$ is H, $R^3$ is H, $R^4$ is H, $R^5$ is F, and Q is

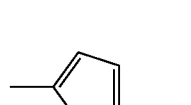

(18) $R^1$ is F, $R^2$ is F, $R^3$ is H, $R^4$ is H, $R^5$ is H, and Q is

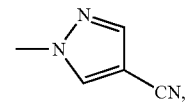

(19) $R^1$ is F, $R^2$ is F, $R^3$ is H, $R^4$ is H, $R^5$ is H, and Q is

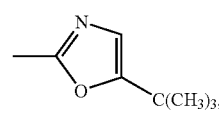

(20) $R^1$ is F, $R^2$ is F, $R^3$ is H, $R^4$ is H, $R^5$ is H, and Q is

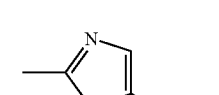

(21) $R^1$ is F, $R^2$ is F, $R^3$ is H, $R^4$ is H, $R^5$ is H, and Q is

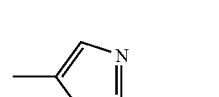

(22) $R^1$ is F, $R^2$ is F, $R^3$ is H, $R^4$ is H, $R^5$ is H, and Q is

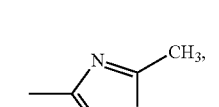

(23) $R^1$ is F, $R^2$ is F, $R^3$ is H, $R^4$ is H, $R^5$ is H, and Q is

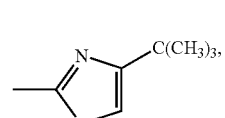

(24) $R^1$ is F, $R^2$ is F, $R^3$ is H, $R^4$ is H, $R^5$ is H, and Q is

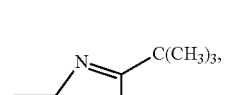

(25) $R^1$ is F, $R^2$ is F, $R^3$ is H, $R^4$ is H, $R^5$ is H, and Q is

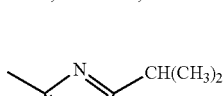

(26) $R^1$ is F, $R^2$ is F, $R^3$ is H, $R^4$ is H, $R^5$ is H, and Q is

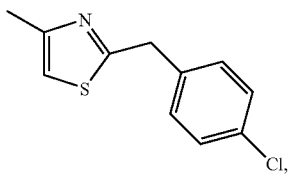

(27) $R^1$ is F, $R^2$ is F, $R^3$ is H, $R^4$ is H, $R^5$ is H, and Q is

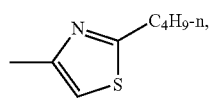

(28) $R^1$ is F, $R^2$ is F, $R^3$ is H, $R^4$ is H, $R^5$ is H, and Q is

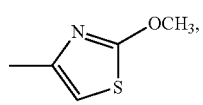

(29) $R^1$ is F, $R^2$ is F, $R^3$ is H, $R^4$ is H, $R^5$ is H, and Q is

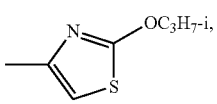

(30) $R^1$ is F, $R^2$ is F, $R^3$ is H, $R^4$ is H, $R^5$ is H, and Q is

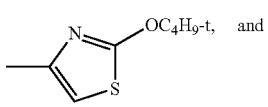

(31) $R^1$ is F, $R^2$ is F, $R^3$ is H, $R^4$ is H, $R^5$ is H, and Q is

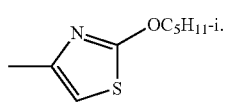

8. A process for preparing compounds of formula (I)

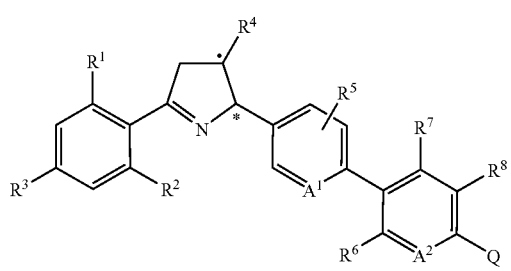
(I)

in which
$R^1$ represents halogen, $C_1$-$C_4$-alkyl, or $C_1$-$C_4$-haloalkyl,
$R^2$ represents hydrogen, halogen, $C_1$-$C_4$-alkyl, or $C_1$-$C_4$-haloalkyl,
$R^3$ represents hydrogen, halogen, or methyl,
$R^4$ represents hydrogen, $C_1$-$C_6$-alkyl, ($C_1$-$C_6$-alkoxy)carbonyl, ($C_3$-$C_6$-cycloalkyl)oxycarbonyl, or ($C_1$-$C_6$-haloalkoxy)carbonyl; or represents aryl that is optionally mono- or polysubstituted by identical or different substituents selected from the group consisting of halogen, cyano, nitro, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, and $C_1$-$C_4$-haloalkylthio,
$A^1$ represents N or CH,
$A^2$ represents $CR^9$,
$R^5$ represents hydrogen, halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkoxy, $C_1$-$C_6$-haloalkylthio, $C_1$-$C_6$-haloalkylsulphinyl, or $C_1$-$C_6$-haloalkylsulphonyl,
$R^6$, $R^7$, $R^8$, and $R^9$ independently of one another represent hydrogen, halogen, cyano, formyl, nitro, tri($C_1$-$C_6$-alkyl)silyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_2$-$C_6$-alkenyl, $C_2$-$C_6$-alkenyloxy, ($C_1$-$C_6$-alkyl)carbonyl, ($C_1$-$C_6$-alkoxy)carbonyl, $C_1$-$C_6$-haloalkyl, $C_1$-$C_6$-haloalkoxy, $C_1$-$C_6$-haloalkylthio, $C_1$-$C_6$-haloalkylsulphinyl, $C_1$-$C_6$-haloalkylsulphonyl, $C_2$-$C_6$-haloalkenyl, $C_2$-$C_6$-haloalkenyloxy, ($C_1$-$C_6$-haloalkyl)carbonyl, ($C_1$-$C_6$-haloalkoxy)carbonyl, pentafluorothio, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$ or —OSO$_2$N$R^{12}R^{13}$,
$R^{10}$ represents hydrogen, $C_1$-$C_6$-alkyl, $C_2$-$C_6$-alkenyl, $C_1$-$C_6$-haloalkyl, $C_2$-$C_6$-haloalkenyl, or $C_3$-$C_6$-cycloalkyl,
$R^{11}$ represents hydrogen, $C_1$-$C_6$-alkyl, $C_2$-$C_6$-alkenyl, $C_1$-$C_6$-haloalkyl, $C_2$-$C_6$-haloalkenyl, or $C_3$-$C_6$-cycloalkyl-$C_1$-$C_4$-alkyl; or represents aryl-$C_1$-$C_4$-alkyl that is optionally mono- or polysubstituted by identical or different radicals $R^5$,
$R^{12}$ and $R^{13}$ independently of one another represent hydrogen, $C_1$-$C_6$-alkyl, or $C_1$-$C_6$-haloalkyl; represent $C_3$-$C_6$-cycloalkyl which is optionally mono- or polysubstituted by identical or different substituents selected from the group consisting of halogen and $C_1$-$C_6$-alkyl; represents $C_3$-$C_6$-cycloalkyl-$C_1$-$C_4$-alkyl; or represents aryl-$C_1$-$C_4$-alkyl that is optionally mono- or polysubstituted by identical or different radicals $R^5$, or
$R^{12}$ and $R^{13}$ together represent $C_2$-$C_6$-alkylene, ($C_1$-$C_3$-alkoxy)-$C_1$-$C_3$-alkylene, or ($C_1$-$C_3$-alkylthio)-$C_1$-$C_3$-alkylene, each of which is optionally mono- or polysubstituted by identical or different substituents selected from the group consisting of halogen and $C_1$-$C_6$-alkyl,
p represents 0, 1, or 2,
Q represents a completely unsaturated 5-membered heterocycle that has 1 to 3 identical or different heteroatoms selected from the group consisting of nitrogen, oxygen, and sulphur and that is mono- or polysubstituted by identical or different radicals selected from $W^1$,
$W^1$ represents halogen, cyano, $C_1$-$C_{16}$-alkyl, $C_1$-$C_{16}$-alkoxy, $C_1$-$C_{16}$-alkylthio, $C_1$-$C_{16}$-alkylsulphinyl, $C_1$-$C_{16}$-alkylsulphonyl, $C_1$-$C_{16}$-haloalkyl, $C_1$-$C_{16}$-haloalkoxy, $C_1$-$C_{16}$-haloalkylthio, $C_1$-$C_{16}$-haloalkylsulphinyl, $C_1$-$C_{16}$-haloalkylsulphonyl, or $C_3$-$C_{12}$-cycloalkyl; or represents aryl or aryl-$C_1$-$C_4$-alkyl, each of which is optionally mono- or polysubstituted by identical or different substituents selected from the group consisting of halogen, cyano, formyl, nitro, tri($C_1$-$C_6$-alkyl)silyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_2$-$C_6$-alkenyl, $C_2$-$C_6$-alkenyloxy, ($C_1$-$C_6$-alkyl)carbonyl, ($C_1$-$C_6$-alkoxy)carbonyl, $C_1$-$C_6$-haloalkyl, $C_1$-$C_6$-haloalkoxy, $C_1$-$C_6$-haloalkylthio, $C_1$-$C_6$-haloalkylsulphinyl, $C_1$-$C_6$-haloalkylsulphonyl, $C_2$-$C_6$-haloalkenyl, $C_2$-$C_6$-haloalkenyloxy, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, the symbol * denotes a stereogenic center and the symbol • denotes a further stereogenic center when $R^4$ does not represent hydrogen, wherein the substituents at the two stereogenic centers are located at cis- or trans-positions relative to each other, comprising reacting $\Delta^1$-pyrrolines of the formula (II)

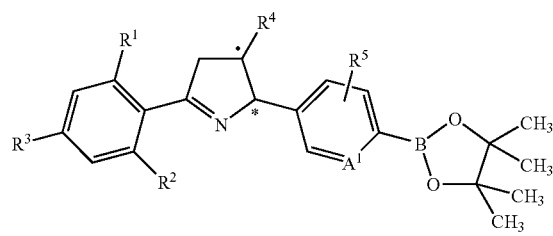

(II)

in which $R^1$, $R^2$, $R^3$, $R^4$, $A^1$, and $R^5$ are as defined above, with a benzene derivative of formula (III)

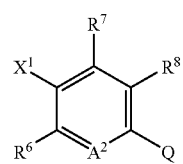

(III)

in which $A^2$, $R^6$, $R^7$, $R^8$, and Q are as defined above, and $X^1$ represents bromine, iodine, or —OSO$_2$CF$_3$, in the presence of a catalyst and in the presence of a diluent.

9. A pesticide comprising one or more compounds of formula (I) according to claim 1 and one or more extenders and/or surfactants.

10. A method for controlling pests comprising applying an effective amount of one or more compounds of formula (I) according to claim 1 to pests and/or their habitat.

11. A process for preparing pesticides comprising mixing one or more compounds of formula (I) according to claim 1 with one or more extenders and/or surfactants.

12. A method for controlling pests comprising applying to the pests and/or their habitat an effective amount of a pyrroline of formula (I-b) in which

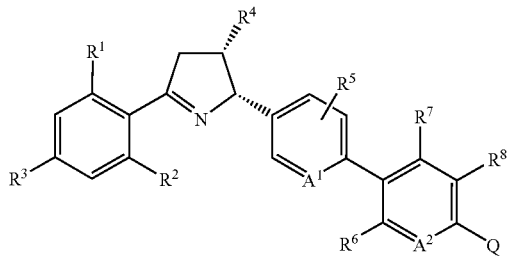

(I-b)

in which $A^1$ represents N or CH, $A^2$ represents C$R^9$, $R^1$ represents halogen, $C_1$-$C_4$-alkyl, or $C_1$-$C_4$-haloalkyl, $R^2$ represents hydrogen, halogen, $C_1$-$C_4$-alkyl, or $C_1$-$C_4$-haloalkyl, $R^3$ represents hydrogen, halogen, or methyl, $R^4$ represents $C_1$-$C_6$-alkyl, ($C_1$-$C_6$-alkoxy)carbonyl, ($C_3$-$C_6$-cycloalkyl)oxycarbonyl, or ($C_1$-$C_6$-haloalkoxy)carbonyl; or represents aryl that is optionally mono- or polysubstituted by identical or different substituents selected from the group consisting of halogen, cyano, nitro, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, and $C_1$-$C_4$-haloalkylthio, $R^5$ represents hydrogen, halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-haloalkoxy, $C_1$-$C_6$-haloalkylthio, $C_1$-$C_6$-haloalkylsulphinyl, or $C_1$-$C_6$-haloalkylsulphonyl, $R^6$, $R^7$, $R^8$, and $R^9$ independently of one another represent hydrogen, halogen, cyano, formyl, nitro, tri($C_1$-$C_6$-alkyl)silyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_2$-$C_6$-alkenyl, $C_2$-$C_6$-alkenyloxy, ($C_1$-$C_6$-alkyl)carbonyl, ($C_1$-$C_6$-alkoxy)carbonyl, $C_1$-$C_6$-haloalkyl, $C_1$-$C_6$-haloalkoxy, $C_1$-$C_6$-haloalkylthio, $C_1$-$C_6$-haloalkylsulphinyl, $C_1$-$C_6$-haloalkylsulphonyl, $C_2$-$C_6$-haloalkenyl, $C_2$-$C_6$-haloalkenyloxy, ($C_1$-$C_6$-haloalkyl)carbonyl, ($C_1$-$C_6$-haloalkoxy)carbonyl, pentafluorothio, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, or —OSO$_2$N$R^{12}R^{13}$, $R^{10}$ represents hydrogen, $C_1$-$C_6$-alkyl, $C_2$-$C_6$-alkenyl, $C_1$-$C_6$-haloalkyl, $C_2$-$C_6$-haloalkenyl or $C_3$-$C_6$-cycloalkyl, $R^{11}$ represents hydrogen, $C_1$-$C_6$-alkyl, $C_2$-$C_6$-alkenyl, $C_1$-$C_6$-haloalkyl, $C_2$-$C_6$-haloalkenyl or $C_3$-$C_6$-cycloalkyl-$C_1$-$C_4$-alkyl; or represents aryl-$C_1$-$C_4$-alkyl that is optionally mono- to polysubstituted by identical or different radicals $R^5$, $R^{12}$ and $R^{13}$ independently of one another represent hydrogen, $C_1$-$C_6$-alkyl, $C_1$-$C_6$-haloalkyl; represent $C_3$-$C_6$-cycloalkyl, which is optionally mono- to polysubstituted by identical or different substituents selected from the group consisting of halogen, and $C_1$-$C_6$-alkyl; represents $C_3$-$C_6$-cycloalkyl-$C_1$-$C_4$-alkyl; or represents aryl-$C_1$-$C_4$-alkyl that is optionally mono- to polysubstituted by identical or different radicals $R^5$, or $R^{12}$ and $R^{13}$ together represent $C_2$-$C_6$-alkylene, ($C_1$-$C_3$-alkoxy)-$C_1$-$C_3$-alkylene, or ($C_1$-$C_3$-alkylthio)-$C_1$-$C_3$- alkylene, each of which is optionally mono- or polysubstituted by identical or different substituents selected from the group consisting of halogen, and $C_1$-$C_6$-alkyl, p represents 0, 1, or 2, Q represents a completely unsaturated 5-membered heterocycle that has 1 to 3 identical or different heteroatoms selected from the group consisting of nitrogen, oxygen, and sulphur and that is mono- or polysubstituted by identical or different radicals selected from $W^1$, $W^1$ represents halogen, cyano, $C_1$-$C_{16}$-alkyl, $C_1$-$C_{16}$-alkoxy, $C_1$-$C_{16}$-alkylthio, $C_1$-$C_{16}$-alkylsulphinyl, $C_1$-$C_{16}$-alkylsulphonyl, $C_1$-$C_{16}$-haloalkyl, $C_1$-$C_{16}$-haloalkoxy, $C_1$-$C_{16}$-haloalkylthio, $C_1$-$C_{16}$-haloalkylsulphinyl, $C_1$-$C_{16}$-haloalkylsulphonyl, or $C_3$-$C_{12}$-cycloalkyl; or represents aryl or aryl-$C_1$-$C_4$-alkyl, each of which is optionally mono- or polysubstituted by identical or different substituents selected from the group consisting of halogen, cyano, formyl, nitro, tri($C_1$-$C_6$-alkyl)silyl, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_2$-$C_6$-alkenyl, $C_2$-$C_6$-alkenyloxy, ($C_1$-$C_6$-alkyl)carbonyl, ($C_1$-$C_6$-alkoxy)carbonyl, $C_1$-$C_6$-haloalkyl, $C_1$-$C_6$-haloalkoxy, $C_1$-$C_6$-haloalkylthio, $C_1$-$C_6$-haloalkylsulphinyl, $C_1$-$C_6$-haloalkylsulphonyl, $C_2$-$C_6$-haloalkenyl, $C_2$-$C_6$-haloalkenyloxy, —C($R^{10}$)=N—O$R^{11}$, —SO$_2$N$R^{12}R^{13}$, —(CH$_2$)$_p$N$R^{12}R^{13}$, —(CH$_2$)$_p$N($R^{12}$)CO$R^{13}$, —(CH$_2$)$_p$N($R^{12}$)SO$_2R^{13}$, —OSO$_2R^{12}$, and —OSO$_2$N$R^{12}R^{13}$, the carbon atom in the 2-position of the pyrrole ring has the R configuration, and the two substituents in the 2- and 3-positions of the pyrrole ring are located cis to each other.

* * * * *